(12) United States Patent
McDevitt et al.

(10) Patent No.: US 8,377,398 B2
(45) Date of Patent: Feb. 19, 2013

(54) METHODS AND COMPOSITIONS RELATED TO DETERMINATION AND USE OF WHITE BLOOD CELL COUNTS

(75) Inventors: John T. McDevitt, Austin, TX (US); Nicolaos J. Christodoulides, Austin, TX (US); Pierre N. Floriano, Austin, TX (US); Gary N. Douglas, Austin, TX (US); Patrick E. Rogers, Burlington, WI (US)

(73) Assignees: The Board of Regents of The University of Texas System, Austin, TX (US); LabNow, Inc., Austin, TX (US)

( * ) Notice: Subject to any disclaimer, the term of this patent is extended or adjusted under 35 U.S.C. 154(b) by 852 days.

(21) Appl. No.: 11/997,396

(22) PCT Filed: May 31, 2006

(86) PCT No.: PCT/US2006/021209
§ 371 (c)(1),
(2), (4) Date: Apr. 23, 2009

(87) PCT Pub. No.: WO2007/053186
PCT Pub. Date: May 10, 2007

(65) Prior Publication Data
US 2009/0215072 A1     Aug. 27, 2009

Related U.S. Application Data

(60) Provisional application No. 60/685,999, filed on May 31, 2005.

(51) Int. Cl.
*G01N 21/00* (2006.01)
*G01N 33/00* (2006.01)
*G01N 33/543* (2006.01)
*B01D 21/00* (2006.01)
*B01D 35/00* (2006.01)

(52) U.S. Cl. ........ 422/554; 422/400; 422/401; 422/403; 422/409; 422/425; 422/427; 422/430; 422/513; 422/534; 422/73; 422/82.05; 422/82.07; 435/7.24; 435/288.6; 436/518; 436/46; 436/63; 436/162; 436/175; 436/177; 436/178

(58) Field of Classification Search ................... 435/7.2, 435/7.24, 7.92, 287.9, 288.3, 297.1; 436/523, 436/524, 528, 10, 56, 172, 177, 178; 422/400, 422/422, 427, 73, 513, 534, 535
See application file for complete search history.

(56) References Cited

U.S. PATENT DOCUMENTS 2,923,669 A    2/1960  Poitras ............................ 435/34
3,587,040 A    6/1971  Fathauer ....................... 640/938
(Continued)

FOREIGN PATENT DOCUMENTS

CA    1330888    7/1994
CA    2515348    8/2004
(Continued)

OTHER PUBLICATIONS

U.S. Appl. No. 60/736,082, filed Nov. 10, 2005, McDevitt et al.
(Continued)

*Primary Examiner* — Gail R Gabel
(74) *Attorney, Agent, or Firm* — Plumsea Law Group, LLC

(57) ABSTRACT

Described herein is an analyte detection device and method related to a portable instrument suitable for point-of-care analyses. In some embodiments, a portable instrument may include a disposable cartridge, an optical detector, a sample collection device and/or sample reservoir, reagent delivery systems, fluid delivery systems, one or more channels, and/or waste reservoirs. Use of a portable instrument may reduce the hazard to an operator by reducing an operator's contact with a sample for analysis. The device is capable of obtaining diagnostic information using cellular- and/or particle-based analyses and may be used in conjunction with membrane- and/or particle-based analysis cartridges. Analytes, including proteins and cells and/or microbes may be detected using the membrane and/or particle based analysis system.

7 Claims, 39 Drawing Sheets

U.S. PATENT DOCUMENTS

| | | | |
|---|---|---|---|
| 3,696,932 A | 10/1972 | Rosenberg | 210/437 |
| 3,701,433 A | 10/1972 | Krakauer et al. | 210/436 |
| 3,709,868 A | 1/1973 | Spector | 530/363 |
| 3,775,742 A | 11/1973 | Koerner et al. | 340/938 |
| 3,827,804 A | 8/1974 | Miller et al. | 356/39 |
| 3,843,696 A | 10/1974 | Wagner et al. | 554/94 |
| 3,844,895 A | 10/1974 | Rose et al. | 435/297.2 |
| 3,856,469 A | 12/1974 | Schneider et al. | 436/536 |
| 3,876,504 A | 4/1975 | Koffler | 435/7.92 |
| 3,954,623 A | 5/1976 | Hammer et al. | 210/436 |
| 3,964,974 A | 6/1976 | Banauch et al. | 435/4 |
| 3,970,429 A | 7/1976 | Updike | 436/535 |
| 4,036,946 A | 7/1977 | Kleinerman | 436/531 |
| 4,038,151 A | 7/1977 | Fadler et al. | 435/288.5 |
| 4,050,898 A | 9/1977 | Goffe et al. | 422/57 |
| 4,069,017 A | 1/1978 | Wu et al. | 436/97 |
| 4,092,630 A | 5/1978 | Van Duuren et al. | 714/748 |
| 4,115,277 A | 9/1978 | Swank | 210/436 |
| 4,189,382 A | 2/1980 | Zine, Jr. | 210/714 |
| 4,200,613 A | 4/1980 | Alfrey et al. | 422/71 |
| 4,245,041 A | 1/1981 | Denney | 435/15 |
| 4,246,107 A | 1/1981 | Takenaka et al. | 210/806 |
| 4,294,817 A | 10/1981 | Burgett et al. | 435/5 |
| 4,317,726 A | 3/1982 | Shepel | 210/236 |
| 4,344,743 A | 8/1982 | Bessman et al. | 417/317 |
| 4,360,611 A | 11/1982 | Wakimoto et al. | 536/216 |
| 4,378,429 A | 3/1983 | Modrovich | 435/11 |
| 4,459,361 A | 7/1984 | Gefter | 436/523 |
| 4,477,575 A | 10/1984 | Vogel et al. | 436/170 |
| 4,493,815 A | 1/1985 | Fernwood et al. | 422/101 |
| 4,567,149 A | 1/1986 | Sell et al. | 436/513 |
| 4,588,665 A | 5/1986 | Drexler | 430/12 |
| 4,596,657 A | 6/1986 | Wisdom | 210/206 |
| 4,623,461 A | 11/1986 | Hossom et al. | 210/445 |
| 4,632,901 A | 12/1986 | Valkirs et al. | 435/5 |
| 4,661,445 A | 4/1987 | Saxinger et al. | 435/5 |
| 4,672,028 A | 6/1987 | Olson | 435/5 |
| 4,677,061 A | 6/1987 | Rose et al. | 435/7.24 |
| 4,681,742 A | 7/1987 | Johnson et al. | 422/102 |
| 4,683,195 A | 7/1987 | Mullis et al. | 435/6 |
| 4,683,202 A | 7/1987 | Mullis | 435/91.2 |
| 4,714,759 A | 12/1987 | Whitaker, Jr. | 424/179.1 |
| 4,734,372 A | 3/1988 | Rotman | 435/29 |
| 4,753,776 A | 6/1988 | Hillman et al. | 422/101 |
| 4,756,884 A | 7/1988 | Hillman et al. | 422/73 |
| 4,777,021 A | 10/1988 | Wertz et al. | 422/101 |
| 4,795,698 A | 1/1989 | Owen et al. | 435/4 |
| 4,810,378 A | 3/1989 | Carmen et al. | 210/206 |
| 4,812,293 A | 3/1989 | McLaurin et al. | 422/69 |
| 4,813,277 A | 3/1989 | Miller et al. | 73/49.2 |
| 4,828,386 A | 5/1989 | Matkovich et al. | 356/246 |
| 4,843,259 A | 6/1989 | Weisshaupt | 327/510 |
| 4,855,225 A | 8/1989 | Fung et al. | 435/6 |
| 4,868,104 A | 9/1989 | Kurn et al. | 435/6 |
| 4,874,499 A | 10/1989 | Smith et al. | 204/403.03 |
| 4,902,630 A | 2/1990 | Bennett et al. | 436/546 |
| 4,908,112 A | 3/1990 | Pace | 210/198.2 |
| 4,910,148 A | 3/1990 | Sorensen et al. | 435/317.1 |
| 4,922,591 A | 5/1990 | Campbell | |
| 4,925,800 A | 5/1990 | Kovacs et al. | 530/388.4 |
| 4,936,998 A | 6/1990 | Nishimura et al. | 210/638 |
| 4,938,742 A | 7/1990 | Smits | 604/67 |
| 4,965,188 A | 10/1990 | Mullis et al. | 435/6 |
| 4,988,618 A | 1/1991 | Li et al. | 435/6 |
| 4,997,577 A | 3/1991 | Stewart | 210/767 |
| 5,053,197 A | 10/1991 | Bowen | 422/58 |
| 5,071,076 A | 12/1991 | Chagnon et al. | 241/21 |
| 5,091,318 A | 2/1992 | Anawis et al. | 436/513 |
| 5,096,660 A | 3/1992 | Hembjer et al. | 376/438 |
| 5,096,669 A | 3/1992 | Lauks et al. | 204/403.02 |
| 5,096,807 A | 3/1992 | Leaback | 435/6 |
| 5,100,777 A | 3/1992 | Chang | 435/7.24 |
| 5,108,933 A | 4/1992 | Liberti et al. | 436/504 |
| 5,126,276 A | 6/1992 | Fish et al. | 436/531 |
| 5,130,238 A | 7/1992 | Malek et al. | 435/91.21 |
| 5,137,031 A | 8/1992 | Guirguis | 600/584 |
| 5,137,833 A | 8/1992 | Russell | 436/94 |
| 5,143,853 A | 9/1992 | Walt | 436/501 |
| 5,147,606 A | 9/1992 | Charlton et al. | 422/53 |
| 5,156,810 A | 10/1992 | Ribi | 422/82.01 |
| 5,156,972 A | 10/1992 | Issachar | 422/68.1 |
| 5,162,863 A | 11/1992 | Ito | 356/73 |
| 5,168,044 A | 12/1992 | Joyce et al. | 435/7.24 |
| 5,182,366 A | 1/1993 | Huebner et al. | 530/334 |
| 5,188,934 A | 2/1993 | Menchen et al. | 435/6 |
| 5,209,904 A | 5/1993 | Forney et al. | 422/73 |
| 5,211,850 A | 5/1993 | Shettigar et al. | 210/645 |
| 5,219,763 A | 6/1993 | Van Hoegaerden | 436/523 |
| 5,223,393 A | 6/1993 | Khanna et al. | 435/6 |
| 5,224,813 A | 7/1993 | Nakamura et al. | 414/352 |
| 5,228,214 A | 7/1993 | Biancalani et al. | 34/126 |
| 5,235,028 A | 8/1993 | Barany et al. | 528/335 |
| 5,236,826 A | 8/1993 | Marshall | 435/7.92 |
| 5,240,640 A | 8/1993 | Siiman et al. | 516/101 |
| 5,244,636 A | 9/1993 | Walt et al. | 422/82.07 |
| 5,244,813 A | 9/1993 | Walt et al. | 436/172 |
| 5,248,742 A | 9/1993 | McGarry et al. | 525/531 |
| 5,250,264 A | 10/1993 | Walt et al. | 422/82.07 |
| 5,252,294 A | 10/1993 | Kroy et al. | 422/102 |
| 5,252,494 A | 10/1993 | Walt | 436/528 |
| 5,262,127 A | 11/1993 | Wise et al. | 422/98 |
| 5,278,303 A | 1/1994 | Krepinsky et al. | 536/55.3 |
| 5,288,214 A | 2/1994 | Fukuda et al. | 417/395 |
| 5,296,375 A | 3/1994 | Kricka et al. | 435/2 |
| 5,307,144 A | 4/1994 | Hiroshi et al. | 356/244 |
| 5,321,454 A | 6/1994 | Mogamiya | 359/391 |
| 5,342,581 A | 8/1994 | Sanadi | 422/101 |
| 5,366,860 A | 11/1994 | Bergot et al. | 435/6 |
| 5,374,530 A | 12/1994 | Nuzzolo et al. | 435/7.22 |
| 5,382,512 A | 1/1995 | Smethers et al. | 435/6 |
| 5,385,709 A | 1/1995 | Wise et al. | 422/98 |
| 5,391,272 A | 2/1995 | O'Daly et al. | 205/777.5 |
| 5,403,720 A | 4/1995 | Sato et al. | 435/31 |
| 5,405,784 A | 4/1995 | Van Hoegaerden | 436/523 |
| 5,408,723 A | 4/1995 | Julien et al. | 16/30 |
| 5,472,672 A | 12/1995 | Brennan | 422/131 |
| 5,478,751 A | 12/1995 | Oosta et al. | 436/165 |
| 5,480,723 A | 1/1996 | Klainer et al. | 428/441 |
| 5,480,804 A | 1/1996 | Niwa et al. | 435/286.1 |
| 5,491,097 A | 2/1996 | Ribi et al. | 436/518 |
| 5,498,392 A | 3/1996 | Wilding et al. | 422/68.1 |
| 5,499,090 A | 3/1996 | Ito et al. | 399/359 |
| 5,499,909 A | 3/1996 | Yamada et al. | 417/384 |
| 5,501,949 A | 3/1996 | Marshall | 435/5 |
| 5,503,985 A | 4/1996 | Cathey et al. | 435/7.9 |
| 5,506,141 A | 4/1996 | Weinreb et al. | 435/309.1 |
| 5,512,490 A | 4/1996 | Walt et al. | 436/171 |
| 5,518,887 A | 5/1996 | Parsons et al. | 435/7.1 |
| 5,541,057 A | 7/1996 | Bogart et al. | 435/5 |
| 5,547,682 A | 8/1996 | Chagnon et al. | 424/497 |
| 5,548,661 A | 8/1996 | Price et al. | 382/133 |
| 5,550,373 A | 8/1996 | Cole et al. | 250/338.1 |
| 5,563,042 A | 10/1996 | Phillips et al. | 435/14 |
| 5,564,497 A | 10/1996 | Fukuoka et al. | 165/152 |
| 5,567,627 A | 10/1996 | Lehnen | 436/518 |
| 5,583,054 A | 12/1996 | Ito et al. | 436/523 |
| 5,587,128 A | 12/1996 | Wilding et al. | 422/50 |
| 5,593,838 A | 1/1997 | Zanzucchi et al. | 506/5 |
| 5,597,531 A | 1/1997 | Liberti et al. | 422/57 |
| 5,608,519 A | 3/1997 | Gourley et al. | 356/318 |
| 5,611,676 A | 3/1997 | Ooumi et al. | 417/322 |
| 5,616,698 A | 4/1997 | Krepinsky et al. | 536/18.6 |
| 5,616,790 A | 4/1997 | Arnold et al. | 562/444 |
| 5,631,130 A | 5/1997 | Leckie et al. | 435/6 |
| 5,632,876 A | 5/1997 | Zanzucchi et al. | 204/600 |
| 5,635,358 A | 6/1997 | Wilding et al. | 435/7.2 |
| 5,637,469 A | 6/1997 | Wilding et al. | 435/7.21 |
| 5,653,939 A | 8/1997 | Hollis et al. | 506/3 |
| 5,654,497 A | 8/1997 | Hoffheins et al. | 73/23.2 |
| 5,674,698 A | 10/1997 | Zarling et al. | 435/7.92 |
| 5,677,195 A | 10/1997 | Winkler et al. | 436/518 |
| 5,677,196 A | 10/1997 | Herron et al. | 436/518 |
| 5,681,484 A | 10/1997 | Zanzucchi et al. | 506/40 |
| 5,681,754 A | 10/1997 | Pope et al. | 436/518 |
| 5,690,763 A | 11/1997 | Ashmead et al. | 156/60 |
| 5,690,807 A | 11/1997 | Clark, Jr. et al. | 205/655 |
| 5,698,089 A | 12/1997 | Lewis et al. | 205/787 |

| Patent | Date | Inventor | Class |
|---|---|---|---|
| 5,698,271 A | 12/1997 | Liberti et al. | 427/550 |
| 5,700,897 A | 12/1997 | Klainer et al. | 528/15 |
| 5,705,018 A | 1/1998 | Hartley | 156/345.1 |
| 5,707,502 A | 1/1998 | McCaffrey et al. | 204/403.1 |
| 5,714,122 A | 2/1998 | Bretscher et al. | 422/82.07 |
| 5,747,265 A | 5/1998 | Parsons et al. | 435/7.2 |
| 5,747,349 A | 5/1998 | Van den Engh et al. | 436/172 |
| 5,748,091 A | 5/1998 | Kim | 340/583 |
| 5,755,942 A | 5/1998 | Zanzucchi et al. | 506/32 |
| 5,756,291 A | 5/1998 | Griffin et al. | 435/6 |
| 5,759,015 A | 6/1998 | Van Lintel et al. | 417/322 |
| 5,770,370 A | 6/1998 | Kumar | 435/6 |
| 5,770,416 A | 6/1998 | Lihme et al. | 435/176 |
| 5,773,307 A | 6/1998 | Colin et al. | 436/526 |
| 5,779,907 A | 7/1998 | Yu | 210/695 |
| 5,788,814 A | 8/1998 | Sun et al. | 279/128 |
| 5,797,898 A | 8/1998 | Santini, Jr. et al. | 604/890.1 |
| 5,804,451 A | 9/1998 | Wang et al. | 436/93 |
| 5,814,524 A | 9/1998 | Walt et al. | 436/518 |
| 5,827,748 A | 10/1998 | Golden | 436/527 |
| 5,827,749 A | 10/1998 | Akers, Jr. | 436/534 |
| 5,834,318 A | 11/1998 | Buettner | 436/518 |
| 5,837,199 A | 11/1998 | Dumschat | 422/68.1 |
| 5,837,552 A | 11/1998 | Cotton et al. | 436/525 |
| 5,837,832 A | 11/1998 | Chee et al. | 506/15 |
| 5,840,256 A | 11/1998 | Demers et al. | 422/102 |
| 5,843,655 A | 12/1998 | McGall | 506/16 |
| 5,843,767 A | 12/1998 | Beattie | 435/287.1 |
| 5,846,396 A | 12/1998 | Zanzucchi et al. | 506/33 |
| 5,846,708 A | 12/1998 | Hollis et al. | 506/12 |
| 5,849,823 A | 12/1998 | Kale et al. | 524/232 |
| 5,854,141 A | 12/1998 | Cronin et al. | 438/763 |
| 5,854,684 A | 12/1998 | Stabile et al. | 356/440 |
| 5,856,174 A | 1/1999 | Lipshutz et al. | 435/286.5 |
| 5,858,648 A | 1/1999 | Steel et al. | 435/5 |
| 5,858,804 A | 1/1999 | Zanzucchi et al. | 506/9 |
| 5,861,242 A | 1/1999 | Chee et al. | 506/3 |
| 5,863,957 A | 1/1999 | Li et al. | 521/61 |
| 5,866,099 A | 2/1999 | Owen et al. | 424/9.322 |
| 5,866,430 A | 2/1999 | Grow | 506/6 |
| 5,869,241 A | 2/1999 | Edwards et al. | 435/6 |
| 5,872,170 A | 2/1999 | Mine et al. | 524/440 |
| 5,872,623 A | 2/1999 | Stabile et al. | 356/73 |
| 5,876,605 A | 3/1999 | Kitajima et al. | 210/650 |
| 5,879,632 A | 3/1999 | Demers | 422/100 |
| 5,891,656 A | 4/1999 | Zarling et al. | 435/7.92 |
| 5,897,993 A | 4/1999 | Sato et al. | 435/29 |
| 5,905,038 A | 5/1999 | Parton | 435/287.6 |
| 5,914,042 A | 6/1999 | Ball et al. | 210/650 |
| 5,922,591 A | 7/1999 | Anderson et al. | 435/287.2 |
| 5,922,617 A | 7/1999 | Wang et al. | 436/518 |
| 5,942,443 A | 8/1999 | Parce et al. | 506/39 |
| 5,945,334 A | 8/1999 | Besemer et al. | 435/287.2 |
| 5,965,590 A | 10/1999 | Rossignol | 514/371 |
| 5,965,695 A | 10/1999 | Simon et al. | 530/324 |
| 5,972,721 A | 10/1999 | Bruno et al. | 436/526 |
| 5,976,813 A | 11/1999 | Beutel et al. | 506/7 |
| 5,980,704 A | 11/1999 | Cherukuri et al. | 506/33 |
| 5,981,297 A | 11/1999 | Baselt | 436/514 |
| 5,985,120 A | 11/1999 | Cholli et al. | 204/452 |
| 5,992,820 A | 11/1999 | Fare et al. | 251/129.01 |
| 6,008,031 A | 12/1999 | Modrich et al. | 435/200 |
| 6,010,463 A | 1/2000 | Lauks et al. | 600/576 |
| 6,013,440 A | 1/2000 | Lipshutz et al. | 506/7 |
| 6,015,662 A | 1/2000 | Hackett, Jr. et al. | 435/5 |
| 6,023,540 A | 2/2000 | Walt et al. | 385/12 |
| 6,027,695 A | 2/2000 | Oldenburg et al. | 506/39 |
| 6,037,137 A | 3/2000 | Komoriya et al. | 435/23 |
| 6,039,889 A | 3/2000 | Zhang et al. | 216/17 |
| 6,045,579 A | 4/2000 | Hochshuler et al. | 323/17.16 |
| 6,048,732 A | 4/2000 | Anslyn et al. | 436/129 |
| 6,063,581 A | 5/2000 | Sundrehagen | 435/7.1 |
| 6,074,616 A | 6/2000 | Buechler et al. | 422/104 |
| 6,083,761 A | 7/2000 | Kedar et al. | 506/30 |
| 6,083,763 A | 7/2000 | Balch | 506/9 |
| 6,103,479 A | 8/2000 | Taylor | 506/14 |
| 6,127,139 A | 10/2000 | Te Koppele et al. | 435/24 |
| 6,133,047 A | 10/2000 | Elaissari et al. | 436/526 |
| 6,133,048 A | 10/2000 | Penfold et al. | 436/533 |
| 6,140,044 A | 10/2000 | Besemer et al. | 435/6 |
| 6,151,973 A | 11/2000 | Geysen et al. | 73/865.8 |
| 6,168,948 B1 | 1/2001 | Anderson et al. | 435/287.2 |
| 6,171,489 B1 | 1/2001 | Ballard et al. | 210/222 |
| 6,171,780 B1 | 1/2001 | Pham et al. | 435/4 |
| 6,174,734 B1 | 1/2001 | Ito et al. | 436/518 |
| 6,184,029 B1 | 2/2001 | Wilding et al. | 435/287.1 |
| 6,197,503 B1 | 3/2001 | Vo-Dinh et al. | 435/6 |
| 6,207,369 B1 | 3/2001 | Wohlstadter et al. | 435/6 |
| 6,210,910 B1 | 4/2001 | Walt et al. | 435/7.32 |
| 6,217,636 B1 | 4/2001 | McFarland | 95/216 |
| 6,219,566 B1 | 4/2001 | Weersink et al. | 600/317 |
| 6,232,066 B1 | 5/2001 | Felder et al. | 435/6 |
| 6,243,486 B1 | 6/2001 | Weiss | 382/133 |
| 6,245,296 B1 | 6/2001 | Ligler et al. | 422/57 |
| 6,248,597 B1 | 6/2001 | Eda et al. | 436/518 |
| 6,254,830 B1 | 7/2001 | Pivarnik et al. | 422/82.07 |
| 6,258,229 B1 | 7/2001 | Winarta et al. | 204/403.04 |
| 6,268,222 B1 | 7/2001 | Chandler et al. | 436/523 |
| 6,288,220 B1 | 9/2001 | Kambara et al. | 536/24.31 |
| 6,296,020 B1 | 10/2001 | McNeely et al. | 137/806 |
| 6,297,060 B1 | 10/2001 | Nowakowski et al. | 436/518 |
| 6,309,889 B1 | 10/2001 | Cutler et al. | 436/165 |
| 6,327,410 B1 | 12/2001 | Walt et al. | 385/115 |
| 6,331,441 B1 | 12/2001 | Balch et al. | 506/15 |
| 6,344,326 B1 | 2/2002 | Nelson et al. | 435/6 |
| 6,350,613 B1 | 2/2002 | Wardlaw et al. | 436/10 |
| 6,350,620 B2 | 2/2002 | Chang et al. | 436/518 |
| 6,355,431 B1 | 3/2002 | Chee et al. | 435/6 |
| 6,355,491 B1 | 3/2002 | Zhou et al. | 436/518 |
| 6,379,929 B1 | 4/2002 | Burns et al. | 435/91.2 |
| 6,391,541 B1 | 5/2002 | Petersen et al. | 435/5 |
| 6,394,952 B1 | 5/2002 | Anderson et al. | 600/300 |
| 6,403,367 B1 | 6/2002 | Cheng et al. | 435/287.1 |
| 6,406,848 B1 | 6/2002 | Bridgham et al. | 435/6 |
| 6,406,920 B1 | 6/2002 | Davis et al. | 436/518 |
| 6,411,207 B2 | 6/2002 | Shaffer | 340/521 |
| 6,413,786 B1 | 7/2002 | Hansen et al. | 436/526 |
| 6,426,050 B1 | 7/2002 | Pham et al. | 422/104 |
| 6,428,666 B1 | 8/2002 | Singh et al. | 204/450 |
| 6,444,461 B1 | 9/2002 | Knapp et al. | 435/283.1 |
| 6,482,593 B2 | 11/2002 | Walt et al. | 435/6 |
| 6,485,690 B1 | 11/2002 | Pfost et al. | 422/102 |
| 6,488,872 B1 | 12/2002 | Beebe et al. | 264/31 |
| 6,488,897 B2 | 12/2002 | Dubrow et al. | 422/102 |
| 6,492,646 B1 | 12/2002 | Sendai et al. | 250/458.1 |
| 6,495,352 B1 | 12/2002 | Brinker et al. | 435/176 |
| 6,508,988 B1 | 1/2003 | Van Dam et al. | 422/102 |
| 6,514,402 B2 | 2/2003 | Iyer et al. | 205/793 |
| 6,514,415 B2 | 2/2003 | Hatch et al. | 210/695 |
| 6,517,736 B1 | 2/2003 | Flannery et al. | 216/33 |
| 6,529,271 B1 | 3/2003 | Engelhardt | 356/317 |
| 6,534,308 B1 | 3/2003 | Palsson et al. | 435/288.7 |
| 6,563,581 B1 | 5/2003 | Oldham et al. | 356/317 |
| 6,565,808 B2 | 5/2003 | Hudak et al. | 422/58 |
| 6,566,079 B2 | 5/2003 | Hefti | 506/9 |
| 6,576,461 B2 | 6/2003 | Heller et al. | 435/287.9 |
| 6,577,777 B1 | 6/2003 | Yoshino et al. | 382/284 |
| 6,589,779 B1 | 7/2003 | McDevitt et al. | 435/288.7 |
| 6,591,124 B2 | 7/2003 | Sherman et al. | 600/345 |
| 6,591,852 B1 | 7/2003 | McNeely et al. | 137/14 |
| 6,601,613 B2 | 8/2003 | McNeely et al. | 137/833 |
| 6,602,702 B1 | 8/2003 | Anslyn et al. | 435/288.7 |
| 6,611,634 B2 | 8/2003 | Herron et al. | 385/12 |
| 6,618,140 B2 | 9/2003 | Frost et al. | 356/317 |
| 6,630,307 B2 | 10/2003 | Bruchez et al. | 435/6 |
| 6,632,613 B1 | 10/2003 | Wei et al. | 435/7.1 |
| 6,638,621 B2 | 10/2003 | Anderson | 428/402.24 |
| 6,649,403 B1 | 11/2003 | McDevitt et al. | 435/288.5 |
| 6,654,505 B2 | 11/2003 | Bridgham et al. | 382/278 |
| 6,665,439 B1 | 12/2003 | Takahashi | 382/199 |
| 6,667,177 B1 | 12/2003 | Yabusaki | 436/10 |
| 6,680,206 B1 | 1/2004 | McDevitt et al. | 436/172 |
| 6,682,649 B1 | 1/2004 | Hansen et al. | 205/777.5 |
| 6,686,170 B1 | 2/2004 | Flanders et al. | 435/7.34 |
| 6,692,696 B1 | 2/2004 | Alberte | 422/50 |
| 6,709,868 B2 * | 3/2004 | Law et al. | 436/10 |
| 6,713,298 B2 | 3/2004 | McDevitt et al. | 435/287.8 |
| 6,716,629 B2 | 4/2004 | Hess et al. | 435/420 |

| | | |
|---|---|---|
| 6,727,058 B2 | 4/2004 | Bushman et al. ............. 435/5 |
| 6,743,640 B2 | 6/2004 | Whitten et al. ............. 436/518 |
| 6,766,817 B2 | 7/2004 | Da Silva ............. 137/1 |
| 6,770,489 B1 | 8/2004 | Enpuku ............. 436/526 |
| 6,773,928 B1 | 8/2004 | Yin et al. ............. 436/518 |
| 6,796,312 B2 | 9/2004 | Eichel ............. 131/334 |
| 6,806,079 B1 | 10/2004 | Pope et al. ............. 435/320.1 |
| 6,808,937 B2 | 10/2004 | Ligler et al. ............. 436/518 |
| 6,818,392 B2 | 11/2004 | Lou et al. ............. 435/5 |
| 6,828,158 B2 | 12/2004 | Eda et al. ............. 436/518 |
| 6,838,236 B1 | 1/2005 | Weiner et al. ............. 435/5 |
| 6,841,159 B2 | 1/2005 | Simonson ............. 424/248.1 |
| 6,844,028 B2 | 1/2005 | Mao et al. ............. 427/384 |
| 6,846,629 B2 | 1/2005 | Sigal et al. ............. 435/6 |
| 6,855,490 B2 | 2/2005 | Sompuram et al. ............. 435/4 |
| 6,861,251 B2 | 3/2005 | Green ............. 506/39 |
| 6,869,570 B2 | 3/2005 | Wardlaw ............. 422/82.05 |
| 6,890,742 B2 | 5/2005 | Ammann et al. ............. 435/91.2 |
| 6,893,879 B2 | 5/2005 | Petersen et al. ............. 436/178 |
| 6,905,885 B2 | 6/2005 | Colston et al. ............. 436/518 |
| 6,906,770 B2 | 6/2005 | Kim et al. ............. 349/141 |
| 6,908,737 B2 | 6/2005 | Ravkin et al. ............. 435/6 |
| 6,908,770 B1 | 6/2005 | McDevitt et al. ............. 436/518 |
| 6,918,404 B2 | 7/2005 | Dias da Silva ............. 137/132 |
| 6,929,030 B2 | 8/2005 | Unger et al. ............. 137/883 |
| 6,949,355 B2 | 9/2005 | Yamanishi et al. ............. 435/34 |
| 6,969,488 B2 | 11/2005 | Bridgham et al. ............. 422/61 |
| 7,008,542 B2 | 3/2006 | Belew et al. ............. 210/660 |
| 7,022,517 B1 | 4/2006 | McDevitt et al. ............. 210/660 |
| 7,066,586 B2 | 6/2006 | Da Silva ............. 347/85 |
| 7,101,963 B2 | 9/2006 | Griffais et al. ............. 536/23.1 |
| 7,119,117 B2 | 10/2006 | Beinlich et al. ............. 514/458 |
| 7,157,049 B2 | 1/2007 | Valencia et al. ............. 435/7.1 |
| 7,157,235 B2 | 1/2007 | Bait et al. ............. 435/7.1 |
| 7,211,443 B2 | 5/2007 | Woudenberg ............. 436/518 |
| 7,219,870 B2 | 5/2007 | Olsson et al. ............. 248/429 |
| 7,241,421 B2 | 7/2007 | Webster et al. ............. 436/180 |
| 7,285,255 B2 | 10/2007 | Kadlec et al. ............. 422/305 |
| 7,297,529 B2 | 11/2007 | Polito et al. ............. 435/285.2 |
| 7,311,671 B2 | 12/2007 | Jung et al. ............. 600/562 |
| 7,316,899 B2 | 1/2008 | McDevitt et al. ............. 435/6 |
| 7,319,017 B2 | 1/2008 | Wagner ............. 435/23 |
| 7,349,717 B2 | 3/2008 | Block et al. ............. 455/552.1 |
| 7,445,886 B2 | 11/2008 | Giroir et al. ............. 435/4 |
| 7,476,361 B2 | 1/2009 | Kellogg et al. ............. 435/287.2 |
| 7,491,552 B2 | 2/2009 | McDevitt et al. ............. 436/518 |
| 7,651,868 B2 | 1/2010 | McDevitt et al. ............. 435/7.1 |
| 2001/0002984 A1 | 6/2001 | Vetter ............. 422/102 |
| 2001/0021534 A1 | 9/2001 | Wohlstadter et al. ............. 436/518 |
| 2002/0019062 A1 | 2/2002 | Lea et al. ............. 436/518 |
| 2002/0055184 A1 | 5/2002 | Naylor et al. ............. 436/514 |
| 2002/0160363 A1 | 10/2002 | McDevitt et al. ............. 435/6 |
| 2002/0182600 A1 | 12/2002 | Smith ............. 435/6 |
| 2002/0183500 A1 | 12/2002 | Macina et al. ............. 536/23.1 |
| 2002/0197622 A1 | 12/2002 | McDevitt et al. ............. 435/6 |
| 2003/0008339 A1 | 1/2003 | Massey et al. ............. 435/14 |
| 2003/0064422 A1 | 4/2003 | McDevitt et al. ............. 435/7.32 |
| 2003/0100036 A1 | 5/2003 | Vojdani ............. 435/7.92 |
| 2003/0100486 A1 | 5/2003 | Ridker et al. ............. 514/3 |
| 2003/0104486 A1* | 6/2003 | Selvan ............. 435/7.2 |
| 2003/0119209 A1 | 6/2003 | Kaylor et al. ............. 436/548 |
| 2003/0129630 A1 | 7/2003 | O'Connor ............. 435/7.32 |
| 2003/0142291 A1 | 7/2003 | Padmanabhan et al. ............. 356/39 |
| 2003/0153011 A1 | 8/2003 | Bell ............. 435/7.9 |
| 2003/0170613 A1 | 9/2003 | Straus ............. 435/5 |
| 2003/0224523 A1 | 12/2003 | Thornberg et al. ............. 436/43 |
| 2003/0232328 A1 | 12/2003 | Houghton et al. ............. 435/5 |
| 2004/0018559 A1 | 1/2004 | Lau et al. ............. 435/7.1 |
| 2004/0029259 A1 | 2/2004 | McDevitt et al. ............. 436/518 |
| 2004/0038318 A1 | 2/2004 | Bell ............. 435/7.4 |
| 2004/0053322 A1 | 3/2004 | McDevitt et al. ............. 435/7.1 |
| 2004/0060867 A1 | 4/2004 | Kriksunov et al. ............. 210/650 |
| 2004/0096991 A1 | 5/2004 | Zhang ............. 436/518 |
| 2004/0137607 A1 | 7/2004 | Tanaami et al. ............. 435/287.2 |
| 2004/0156746 A1 | 8/2004 | Larsen ............. 422/58 |
| 2004/0163970 A1 | 8/2004 | Sin et al. ............. 205/792 |
| 2004/0235189 A1 | 11/2004 | Lu ............. 436/514 |
| 2005/0019222 A1 | 1/2005 | Medland ............. 422/100 |
| 2005/0079507 A1 | 4/2005 | Fang ............. 435/6 |
| 2005/0136548 A1 | 6/2005 | McDevitt et al. ............. 436/180 |
| 2005/0153271 A1 | 7/2005 | Wenrich ............. 435/1.1 |
| 2005/0164404 A1 | 7/2005 | Marlborough et al. ............. 436/514 |
| 2005/0191620 A1 | 9/2005 | McDevitt et al. ............. 435/5 |
| 2006/0073585 A1 | 4/2006 | McDevitt et al. ............. 435/287.1 |
| 2006/0079000 A1 | 4/2006 | Floriano et al. ............. 435/288.7 |
| 2006/0105419 A1 | 5/2006 | Blankenberg et al. ............. 435/25 |
| 2006/0106316 A1 | 5/2006 | Palti ............. 600/476 |
| 2006/0228256 A1 | 10/2006 | McDevitt et al. ............. 422/82.05 |
| 2006/0234209 A1* | 10/2006 | Walker et al. ............. 435/5 |
| 2006/0257854 A1 | 11/2006 | McDevitt et al. ............. 435/5 |
| 2006/0257991 A1 | 11/2006 | McDevitt et al. ............. 435/287.1 |
| 2006/0257992 A1 | 11/2006 | McDevitt et al. ............. 435/287.2 |
| 2006/0257993 A1 | 11/2006 | McDevitt et al. ............. 435/287.2 |
| 2006/0263825 A1 | 11/2006 | Denny et al. ............. 435/7.1 |
| 2007/0183978 A1 | 8/2007 | Preuss et al. ............. 424/9.81 |
| 2008/0219891 A1 | 9/2008 | McDevitt et al. ............. 422/82.05 |
| 2008/0300798 A1 | 12/2008 | McDevitt et al. ............. 436/518 |
| 2009/0215646 A1 | 8/2009 | Anslyn et al. ............. 506/12 |

FOREIGN PATENT DOCUMENTS

| | | |
|---|---|---|
| DE | 19736641 | 3/1999 |
| EP | 0109531 | 5/1984 |
| EP | 0246760 | 11/1987 |
| EP | 0339623 | 12/1993 |
| EP | 0641250 | 3/1996 |
| EP | 0439182 | 4/1996 |
| EP | 0518557 | 8/1996 |
| EP | 1363126 | 12/2005 |
| FR | 2 677 664 | 12/1992 |
| GB | 2300258 | 10/1996 |
| GB | 2315131 | 1/1998 |
| JP | 10-332593 | 12/1998 |
| KR | 1020030032809 | 4/2003 |
| KR | 1020030032811 | 4/2003 |
| KR | 1020030032812 | 4/2003 |
| KR | 1020030332810 | 4/2003 |
| KR | 1020030033134 | 5/2003 |
| KR | 1020030041458 | 5/2003 |
| KR | 1020030073779 | 9/2003 |
| KR | 1020030092680 | 12/2003 |
| KR | 1020040012008 | 2/2004 |
| KR | 1020040012009 | 2/2004 |
| KR | 1020040012010 | 2/2004 |
| KR | 1020040012431 | 2/2004 |
| KR | 1020030026853 | 3/2006 |
| NL | 1007489 | 10/2000 |
| WO | WO 90/01069 | 2/1990 |
| WO | WO 92/00880 | 1/1992 |
| WO | WO 93/23154 | 11/1993 |
| WO | WO 94/19690 | 9/1994 |
| WO | WO 97/25437 | 7/1997 |
| WO | WO 97/35181 | 9/1997 |
| WO | WO 97/35189 | 9/1997 |
| WO | WO 97/36681 | 10/1997 |
| WO | WO 98/17383 | 4/1998 |
| WO | WO 98/25701 | 6/1998 |
| WO | WO 98/40726 | 9/1998 |
| WO | WO 98/53300 | 11/1998 |
| WO | WO 99/17139 | 4/1999 |
| WO | WO 99/18434 | 4/1999 |
| WO | WO 99/19515 | 4/1999 |
| WO | WO 99/37814 | 7/1999 |
| WO | WO 99/67024 | 12/1999 |
| WO | WO 00/04372 | 1/2000 |
| WO | WO 00/20117 | 4/2000 |
| WO | WO 00/55635 | 9/2000 |
| WO | WO 01/06239 | 1/2001 |
| WO | WO 01/06244 | 1/2001 |
| WO | WO 01/06253 | 1/2001 |
| WO | WO 01/11338 | 2/2001 |
| WO | WO 01/28681 | 4/2001 |
| WO | WO 01/55701 | 8/2001 |
| WO | WO 01/55702 | 8/2001 |
| WO | WO 01/55703 | 8/2001 |
| WO | WO 01/55704 | 8/2001 |
| WO | WO 01/55952 | 8/2001 |
| WO | WO 01/66104 | 9/2001 |
| WO | WO 01/94528 | 12/2001 |

| | | |
|---|---|---|
| WO | WO 02/18658 | 3/2002 |
| WO | WO 02/061392 | 8/2002 |
| WO | WO 03/041862 | 5/2003 |
| WO | WO 03/090605 | 11/2003 |
| WO | WO 03/104770 | 12/2003 |
| WO | WO 03/104771 | 12/2003 |
| WO | WO 03/104772 | 12/2003 |
| WO | WO 2004/009840 | 1/2004 |
| WO | WO 2004/072097 | 8/2004 |
| WO | WO 2004/072613 | 8/2004 |
| WO | WO 2005/008225 | 1/2005 |
| WO | WO 2005/008226 | 1/2005 |
| WO | WO 2005/009270 | 2/2005 |
| WO | WO 2005/059551 | 6/2005 |
| WO | WO 2005/082407 | 9/2005 |
| WO | WO 2005/083423 | 9/2005 |
| WO | WO 2005/085796 | 9/2005 |
| WO | WO 2005/085854 | 9/2005 |
| WO | WO 2005/085855 | 9/2005 |
| WO | WO 2005/090983 | 9/2005 |
| WO | WO 2007/002480 | 1/2007 |
| WO | WO 2007/005666 | 1/2007 |
| WO | WO 2007/134189 | 11/2007 |
| WO | WO 2007/134191 | 11/2007 |

OTHER PUBLICATIONS

"1994 Revised Guidelines for the Performance of CD4+ T-Cell Determinations in Persons with Human Immunodeficiency Virus (HIV) Infections," *MWMR Recommendations and Reports*, 43(RR-3):1-25, 1994.
"Biosensors respond with colored light," *Science News*, 317, 1997.
"Examiner's first report on patent application No. 2003228711 by Board of Regents, The University of Texas System," issued in Australian patent application No. 203228711, dated Sep. 26, 2007.
"Q&A II: Basic facts about the AIDS epidemic and its impact," *UNAIDS Questions & Answers*, Nov. 2004.
"Q&A III: Selected issues: prevention and care," *UNAIDS Questions & Answers*, Nov. 2004.
"Sandia researchers develop portable devices that can detect heart and gum disease instantly," http://www.sandia.govinews-center/news-releases/2005/elect-semi-sensors/medical.html, Jan. 27, 2005.
Adler et al., "Efficacy of a novel metalloprotease inhibitor on botulinum neurotoxin B activity," *FEBS Lett.*, 429:234-238, 1998.
Aguirre et al., "Sialochemistry—A diagnostic-tool," *Critical Reviews of Oral Biology & Medicine*, 4(3-4):343-350, 1993.

American Heart Association, Heart Disease and Stroke Statistics—2004.

Anderson and Anderson, "The human plasma proteome: history, character, and diagnostic prospects," *Molecul. Cell. Proteomics*, 1(11):845-867, 2002.

Anderson, "Candidate-based proteomics in the search for biomarkers of cardiovascular disease," *J. Physiology-London*, 563:23-60, 2005.

Anderson, "The roles of multiple proteomic platforms in a pipeline for new diagnostics," *Molecul. Cell. Proteomics*, 4(10):1441-1444, 2005.

Anido et al., "ZD1839, a specific epidermal growth factor receptor (EGFR) tyrosine kinase inhibitor, induces the formation of inactive EGFR/HER2 and EGFR/HER3 heterodimers and prevents heregulin signaling in HER2-overexpressing breast cancer cells," *Clin. Cancer Res.*, 9:1274-83, 2003.

Asada et al., "CD4+ T-lymphocyte-induced Epstein-Barr virus reactivation in a patient with severe hypersensitivity to mosquito bites and Epstein-Barr virus-infected NK cell lymphocytosis," *Arch. Dermatol.*, 139:1601-1607, 2003.

Baorto et al., "Using logical observation identifier names and codes (LOINC) to exchange laboratory data among three academic hospitals," *Proc. AMIA Annu. Fall Symp*, 69-100, 1997.

Barany, "Genetic disease detection and DNA amplification using cloned thermostable ligase," *Proc. Natl. Acad. Sci. USA*, 88:189-193, 1991.

Barany, "The ligase chain reaction in a PCR world," *PCR Methods and Applications*, 1:5-16, 1991.

Barnett et al., "Standardization of lymphocyte antibody binding capacity—a multi-centre study," *Clin. Lab. Haematol.*, 22:89-96, 2000.

Baumann et al., "Interaction of cytokine- and glucocorticoid-response elements of acute-phase plasma protein genes. Importance of glucocorticoid receptor level and cell type for regulation of the elements from rat alpha 1-acid glycoprotein and beta-fibrinogen genes," *J. Biol. Chem.*, 265(36):22275-22281, 1990.

Blake et al., "Blood pressure, C-reactive protein and risk of future cardiovascular events: a prospective study among 15,215 women," *European Society of Cardiology Congress 2003*, Vienna, Austria, Abstract 652.

Blake et al., "Effect of pravastatin on LDL particle concentration as determined by NMR spectroscopy: a substudy of a randomized placebo controlled trial," *Europ. Heart J.*, 24:116-116, 2003.

Callan, "The immune response to Epstein-Barr virus," *Microbes and Infection*, 6:937-945, 2004.

Chiwakata at al., "High levels of inducible nitric oxide synthase mRNA are associated with increased monocyte counts in blood and have a beneficial role in *Plasmodium falciparum* malaria," *Infect. Immun.*, 68:394-399, 2000.

Cho et al., "An unnatural biopolymer," *Science*, 261:1303-1305, 1993.

Christodoulides et al., "A microchip-based multianalyte assay system for the assessment of cardiac risk," *Analytical Chem.*, 74(13):3030-3036, 2002.

Christodoulides et al., "Application of microchip assay system for the measurement of C-reactive protein in human saliva," *Lab. Chip*, 5(3):261-9, 2005.

Christodoulides et al., "Toward the development of a lab-on-a-chip dual-function leukocyte and C-reactive protein analysis method for the assessment of inflammation and cardiac risk.," *Clinical Chem.*, 51(12):2391-2395, 2005a.

Cohen et al., "Multiple Rare Alleles Contribute to Low Plasma Levels of HDL Cholesterol ," Science, 305:869-872, 2004.

Coller, "Leukocytosis and Ischemic Vascular Disease Morbidity and Mortality: Is It Time to Intervene? ," *Arterioscler Thromb Vasc. Biol.*, 25:658-670, 2005.

Communication pursuant to Article 96(2) Epc issued in European Patent Application No. 03 765 999.Feb. 1223, European Patent Office, Aug. 21, 2007.

Cowley et al., "Increased EGF receptors on human squamous carcinoma cell lines," *Br. J. Cancer*, 53:223-9, 1986.

Davis at al., "Determination of CD4 antigen density on cells: role of antibody valency, avidity, clones, and conjugation," *Cytometry*, 33:197-205, 1998.

de Lemos et al., "The prognostic value of B-type natriuretic peptide in patients with acute coronary syndromes," *NE J. Med.*, 345(14):1014-1021, 2001.

Deng at al., "Allosteric Interaction of Metal Ions with Saccharides in a Crowned Diboronic Acid," *J. Am. Chem. Soc.*, 116:4567-4572, 1994.

Denny, T.N. et al., "Quantitative determination of surface antibody binding capacities of immune subsets present in peripheral blood of healthy adult donors," *Cytometry Part A*, vol. 26, No. 4, Dec. 1996, pp. 265-274.

DeStefano et al., "Dental disease and risk of coronary heart disease and mortality," *Bmj*, 306(6879):688-91, 1993.

Desvarieux et al., "*Periodontal microbiota* and carotid intima-media thickness: the Oral Infections and Vascular Disease Epidemiology Study (INVEST)," *Circulation*, 111(5):576-82, 2005.

Dickinson et al., "Convergent, Self-Encoded Bead Sensor Arrays in the Design of an Artificial Nose," *Anal. Chem.*, 2192-2198, 1999.

Erwin et al., "Quantitative measurement of IgE antibodies to purified allergens using streptavidin linked to a high-capacity solid phase," *Journal of Allergy and Clinical Immunology*, 115(5):1029-1035, 2005.

European Patent Office, Communication pursuant to Article 94(3) EPC, issued in European Patent Application No. 05 755 340.6, dated Jun. 3, 2008.

European Patent Office, "Communication pursuant to Article 96(2) EPC,", issued in European Patent Application No. 00975164.5, dated Nov. 29, 2005.

European Search Report (Supplementary), issued in European Patent Application No. 03 76 5999, dated Jul. 14, 2006.
European Search Report, issued in European Patent Application No. 02713535.9, dated Feb. 18, 2004.
Examiner's Report, issued in Australian Application No. 13255/01, dated Sep. 3, 2003.
Examiner's Report, issued in Australian Application No. 53165/99, dated May 2, 2002.
Examiner's Report, issued in Australian Application No. 53165/99, dated May 5, 2003.
Extended European Search Report, issued in European Patent Application No. 08168266, dated Jun. 22, 2009.
Ferguson, "Current diagnostic uses of saliva," *Journal of Dental Research*, 66(2):420-424, 1987.
Forster, "Transfer Mechanisms of Electronic Excitation," 10$^{th}$ Spiers Memorial Lecture, *Discussions of the Faraday Soc.*, 27:7-17, 1959.
Ganter et al., "Dual control of C-reactive protein gene expression by interleukin-1 and interleukin-6," *Embo. J.*, 8(12):3773-3779, 1989.
Glencross et aL, "CD45-assisted PanLeucogating for accurate, cost-effective dual-platform CD4+ T-cell enumeration," *Cytometry*, 50:69-77, 2002.
Goldrick et al.,"Nicra™—A Rapid robust method for screening for unknown point mutations," *Biotechniques*, 21:106-112, 1996.
Graham et al., "Field Testing of a Portable Microchip Assay for CD4 Counts in Botswana," presented at 2$^{nd}$ International AIDS Society Conference on HIV Pathogenesis and Treatment in Paris, France, 2003.
Grate et al.," Hydrogen Bond Acidic Polymers for Surface Acoustic Wave Vapor Sensors and Arrays," *Analytical Chem.*, 71:1033-1040, 1999.
Guatelli et al., "Isothermal, in vitro amplification of nucleic acids by a multienzyme reaction modeled after retroviral replication," Proc. Natl. Acad. Sci. USA, 87:1874-1878, 1990.
Hamasaki et al., "Fluorescent sensors of molecular recognition. Modified cyclodextrins capable of exhibiting guest-responsive twisted intramolecular charge transfer fluorescence," *J. Am. Chem. Soc.*, 115:5035-5040, 1993.
Han et al., "Deflection behavior of Fabry-Perot pressure sensors having planar and corrugated diaphragms," *Microelectronics Research Center and Department of Electrical and Computer Engineering*, 5034-5040, 1997.
Han et al., "Fabrication and characterization of a Fabry-Perot based chemical sensor," *Microelectronics Research Center and Department of Electrical and Computer Engineering*, 1997 (12 pages).
Han, "Fabry-Perot cavity chemical sensors by silicon micromachining techniques," *Applied Physics Letters*, 74(3):445-447, 1999.
Harris et al., "Associations of elevated interleukin-6 and C-reactive protein levels with mortality in the elderly," *Amer. J. Med.*, 106(5):506-512, 1999.
Harrison, "A structural taxonomy of DNA-binding domains," *Nature (London)*, 353:715-719, 1991.
Healey et al., "Fast temporal response fiber-optic chemical sensors based on the photodeposition of micrometer-scale polymer arrays," *Analytical Chemistry*, 69(11):2213-2216, 1997.
Henriksson et al., "Antibodies to CD4 in primary Sjogren's syndrome," *Br. Soc. Rheum.*, 39:142-147, 2000.
Hermann, "New kits on the blot—can we microarray the future of atherosclerosis?" *Cardiovascular Research*, 60(2):220-222, 2003.
Hodinka et al., "Detection of human immunodeficiency virus antibodies in oral fluids," *Clinical and Diagnostic Laboratory Immunology*, 5(4):419-426, 1998.
Holtz et al., "Intelligent Polymerized Crystalline Colloidal Arrays: Novel Chemical Sensor Materials," *Analytical Chem.*, 70:780-791, 1998.
Horne et al., "Which white blood cell subtypes predict increased cardiovascular risk?," *Journal of the American College of Cardiology*, 45:1638-1643, 2005.
Hortin et al., "Proteomics: a new diagnostic frontier," *Clinical Chem.*, 52:1218-1222, 2006.
Horwich et al., "Cardiac troponin I is associated with impaired hemodynamics, progressive left ventricular dysfunction, and increased mortality rates in advanced heart failure," *Circulation*, 108(7):833-838, 2003.
Houwen, "The Differential Cell Count," *Lab. Hematology*, 7:89-100, 2001.
Hsu et al., "A far-red fluorescent contrast agent to image epidermal growth factor receptor expression," *Photochem. Photobiol.*, 79:272-9, 2004.
Hsu et al., "Detection of DNA point mutations with DNA mismatch repair enzymes," *Carcinogenesis*, 15:1657-1662, 1994.
Huang, "Enzyme abnormalities of patients with acquired immunodeficiency syndrome," *Clin. Chem.*, 34:2574-2576, 1988.
Ibegbu et al., "Subpopulations of T and B Cells in Perinatally HIV-Infected and Noninfected Age-Matched Children Compared with Those in Adults," *Clin. Immunol. Immunopathology*, 71:27-32, 1994.
Ilva et al., "Improved early risk stratification and diagnosis of myocardial infarction, using a novel troponin I assay concept," *European Journal of Clinical Investigation*, 35:112-116, 2005.
International Preliminary Examination Report, issued in Application No. PCT/US2001/03240, dated Jun. 6, 2002.
International Preliminary Examination Report, issued in Application No. PCT/US1999/16162, dated Oct. 12, 2000.
International Preliminary Examination Report, issued in Application No. PCT/US2000/19302, dated Oct. 12, 2001.
International Preliminary Examination Report, issued in Application No. PCT/US2000/19351, dated Aug. 14, 2001.
International Preliminary Examination Report, issued in Application No. PCT/US2000/19350, dated Aug. 14, 2001.
International Preliminary Examination Report, issued in International Application No. PCT/US2003/23131, dated May 18, 2004.
International Preliminary Report on Patentability, for International Application No. PCT/US2004/003610, dated Aug. 18, 2005.
International Preliminary Report on Patentability, for International Application No. PCT/US2005/006074, dated Sep. 8, 2006.
International Preliminary Report on Patentability, for International Application No. PCT/US2006/021209, dated Dec. 21, 2007.
International Search Report and Written Opinion, issued in International Application No. PCT/US2004/03751, dated Aug. 20, 2004.
International Search Report and Written Opinion, issued in International Application No. PCT/US2004/041633, dated Nov. 14, 2005.
International Search Report and Written Opinion, issued in International Application No. PCT/US2005/006593, dated Sep. 27, 2005.
International Search Report and Written Opinion, issued in International Application No. PCT/US2005/006074, dated Oct. 24, 2005.
International Search Report and Written Opinion, issued in International Application No. PCT/US2006/021209, dated Jun. 4, 2007.
International Search Report and Written Opinion, issued in International Application No. PCT/US2008/60532, dated Oct. 1, 2008.
International Search Report and Written Opinion, issued in International Application No. PCT/US2007/68704, dated Oct. 17, 2007.
International Search Report and Written Opinion, issued in International Application No. PCT/US2007/68701, dated Apr. 15, 2008.
International Search Report, issued in International Application No. PCT/US2006/24603, dated Nov. 24, 2008.
International Search Report, issued in International Application No. PCT/US2004/03610, dated Jan. 24, 2005.
International Search Report, issued in International Application No. PCT/US2000/19350, dated Feb. 22, 2001.
International Search Report, issued in International Application No. PCT/US2000/19351, dated Feb. 22, 2001.
International Search Report, issued in International Application No. PCT/US2000/19302, dated Feb. 22, 2001.
International Search Report, issued in International Application No. PCT/US2001/03316, dated May 7, 2001.
International Search Report, issued in International Application No. PCT/US2001/03139, dated May 7, 2001.
International Search Report, issued in International Application No. PCT/US2001/03240, dated May 7, 2001.
International Search Report, issued in International Application No. PCT/US2001/03241, dated May 7, 2001.
International Search Report, issued in International Application No. PCT/US2001/03141, dated Oct. 19, 2001.
International Search Report, issued in International Application No. PCT/US2002/03277, dated Feb. 13, 2003.
International Search Report, issued in International Application No. PCT/US2002/03275, dated May 7, 2003.

International Search Report, issued in International Application No. PCT/US2003/12951, dated Oct. 14, 2003.
International Search Report, issued in International Application No. PCT/US2003/23131, dated Dec. 12, 2003.
International Search Report, issued in International Application No. PCT/US1999/16162, dated Nov. 26, 1999.
International Search Report, issued in International Application No. PCT/US2004/03751, dated Aug. 20, 2004.
International Search Report, issued in International Application No. PCT/US2005/006077, dated Jul. 26, 2005.
International Search Report, issued in International Application No. WO 2007/134189, dated Apr. 15, 2008.
Invitation to Pay Additional Fees, issued in International Application No. PCT/US2004/041633, dated Jun. 17, 2005.
Invitation to Pay Additional Fees, issued in International Application No. PCT/US2005/006350, dated Aug. 3, 2005.
Invitation to Pay Additional Fess, issued in International Application No. PCT/US2005/006074, dated Aug. 3, 2005.
Irwin, "Low CD4+ T Lymphocyte Counts," www.virusmyth.net/aids/data/milowcd4.htm, Feb. 2001.
James et al., "A Glucose-Selective Molecular Fluorescence Sensor," *Angew. Chem.*, 33:2207-2209, 1994.
James at al., "Chiral discrimination of Monosaccharides through Gel Formation," *Chem. Lett. Jpn.*, 23:273-276, 1994.
James et al., "Chiral discrimination of monosaccharides using a fluorescent molecular sensor," *Nature*, 374:345-347, 1995.
James et al., "Determination of the Absolute Configuration of Monosaccharides by a Colour Change in a Chiral Cholestreric Liquid Crystal System," *J. Chem. Soc. Chem., Commun.*, 10:857-860, 1993.
James et al., "Novel Photoinduced Electron-transfer Sensor for Saccharides based on the Interaction of Boronic Acid and Aminer," *J. Chem. Soc., Chem Commun.*, 4:477-478, 1994.
James et al., "Novel Saccharide-Photoinduced Electron Transfer Sensors Based on the Interaction of Boronic Acid and Amine," *J. Am. Chem. Soc.*, 117:8982-8987, 1995.
Janossy et al., "Precise CD4 T-Cell Counting Using Red Diode Laser Excitation: For Richer, For Poorer," *Cytometry*, 50:78-85, 2002.
Jarvis et al., "Childern's exposure to passive smoking in England since the 1980s: Continine evidence from population surveys," *Bmj*, 321(7257):343-5, 2000.
Jennings et al., "A Phenotypic Study of CD8+ Lymphocyte Subsets in Infants Using Three-Color Flow Cytometry," *Clin. Immunol. Immunopathology*, 71:8-13, 1994.
Johnson et al., "Identification of Multiple Analytes Using an Optical Sensor Array and Pattern Recognition Neural Networks," *Analytical Chem.*, 69:4641-4648, 1997.
Joshipura et al., "Poor oral health and coronary heart disease," *J. Dent. Res.*, 75(9):1631-6, 1996.
Kaiser et al., "Color test for detection of free terminal amino groups in the solid-phase synthesis of peptides," *Anal. Biochem.*, 34:595-598, 1970.
Kaski et al., "Neutrophil count and complex lesions in patients with coronary artery disease," *Arterioscler Thromb Vasc Biol.*, 25:e112, 2005.
Kaufman et al., "The Diagnostic Applications of Saliva—A Review," *Crit. Rev. Oral. Biol. Med.*, 13(2):197-212, 2002.
Keavney, "Plasma C-reactive protein (CRP), a novel cardiovascular risk factor, shows high heritability but no association with the -174 G/C polymorphism of the interleukin-6 (IL-6) gene in human families," *Abstracts from the American Heart Association Scientific Sessions 2000*, 102:329, 2000.
Kelleher and Misbah, "What is Good's syndrome? Immunological abnormalities in patients with thymoma," *J. Clin. Pathol.*, 56:12-16, 2003.
Ketema et al., "Assessment of the Performance of a Rapid, Lateral Flow Assay for the Detection of Antibodies to HIV," *J. Acquir. Immune Defic. Syndr.*, 27:63-70, 2001.
Khanna et al.," 4', 5'—Dimethoxy1-6-carboxyfluorescein, A Novel Dipole-Dipole Coupled Fluorescence Energy Transfer Acceptor Useful for Fluorescence Immunoassays," *Anal. Biochem.*, 108:156-161, 1980.
Kimming et al., "Quantitative determination of the epidermal growth factor receptor in cervical cancer and normal cervical epithelium by 2-color flow cytometry: evidence for down-regulation in cervical cancer," *Int. J. Cancer*, 74:365-73, 1997.
Klug, "Co-chairman's remarks: protein designs for the specific recognition of DNA," *Gene*, 135:83-92, 1993.
Kondo et al., "Specific complexation of disaccharides with diphenyl-3,3'-diboronic acid that can be detected by circular dichroism," *Tetrahedron*, 48:8239-8252, 1992.
Kragelund et al., "N-terminal pro-B-type natriuretic peptide and long-term mortality in stable coronary heart disease," *NE J. Med.*, 352(7):666-675, 2005.
Kramer et al., "Relative frequency of malaria pigment-carrying monocytes of nonimmune and semi-immune patients from flow cytometric depolarized side scatter," *Cytometry*, 45:133-140, 2001.
Kwoh et al., "Transcription-based amplification system and detection of amplified human immunodeficiency virus type 1 with a bead-based sandwich hybridization format," *Proc. Natl. Acad. Sci. USA*, 86:1173-1177, 1989.
Ladhani et al., "Changes in white blood cells and platelets in children with falciparum malaria: relationship to disease outcome," *Br. J. Hematology*, 119:839-847, 2002.
Lalvani, Ajit, "Counting Antigen-Specific T Cells: A New Approach for Monitoring Response to Tuberculosis Treatment?" *Editorial Commentary in Clinical Infectious Diseases*, vol. 38, Mar. 2004, pp. 757-759.
Lange at al., "CT genotype of promotor polymorphism C159T in the CD14 gene is associated with lower prevalence of atopic dermatitis and lower IL-13 production," *Pediatr. Allergy Immunol.*, 16:456-457, 2005.
Lauritzen et al., "Peptide dot immunoassay and immunoblotting: electroblotting from aluminum thin-layer chromatography plates and isoelectric focusing gels to activated nitrocellulose," *Electrophoresis*, 14:852-859, 1993.
Lavigne et al., "Solution-based analysis of multiple analytes by a sensor array: Toward the development of an 'Electronic Tongue'," *J. Am. Chem. Soc.*, 120:6429-6430, 1998.
Ledergerber et al., "Human Immunodeficiency Virus Type I p24 Concentration Measured by Boosted ELISA of Heat-Denatured Plasma Correlates with Decline in CD4 Cells, Progression to AIDS, and Survival: Comparison with Viral RNA Measurement," *J. Infect. Dis.*, 181:1280-1287, 2000.
Lepej et al., "Center for Disease Control (CDC) flow cytometry panel for human immunodeficiency virus infection allows recognition of infectious mononucleosis caused by Epstein-Barr virus or cytomegalovirus," *Croat. Med. J.*, 44:702-706, 2003.
Li et al., "RNA profiling of cell-free saliva using microarray technology," *J. Dent. Res.*, 83(3):199-203, 2004.
Li et al., "Salivary transcriptome diagnostics for oral cancer detection," *Clin. Cancer Res.*, 10(24):8442-50, 2004.
Libby et al.," Inflammation and atherosclerosis," *Circulation*, 105(9):1135-1143, 2002.
Liebeschuetz, S. et al., "Diagnosis of tuberculosis in South African children with a T-cell-based assay: a prospective cohort study," *Lancet*, vol. 364, Dec. 2004, pp. 2196-2203.
Liszewski, "Biomarker detection & measurement—Harnessing useful diagnostic and therapeutic information," *Genetic Engineering News*, 26(6):1-+, 2006.
Litwiller. CCD vs CMOS: Facts or Fictions, "Choosing a imager means considering no only the chip, but also its manufacturer and how you application will evolve," *Potonics Spectra*, 1-4, 2001.
Loveday and Hill, "Prediction of progression to AIDS with serum HIV-1 RNA and CD4 count," *Lancet*, 345:790-791, 1995.
Luc et al., "C-reactive protein, interleukin-6, and fibrinogen as predictors of coronary heart disease the PRIME study," *Arteriosclerosis Thrombosis and Vascular Biology*, 23(7):1255-1261, 2003.
Luczynski et al., "Monocytes in children with leukemias and lymphomas—down-regulation of HLA and costimulatory molecules," *Acta Biochimicia Polonica*, 51:1067-1073, 2004.
Ludwig et al., "Chiral discrimination of monosaccharides by monolayers of a steroidal boronic acid," *J. Chem. Soc. Perkin Trans*, 4:697-702, 1994.
Lyamuya et al., "Evaluation of the FACScount, TRAx CD4 and Dynabeads methods for CD4 lymphocyte determination," *J. Immunol. Methods*, 195:103-112, 1996.

Lyke et al., "Association of intraleukocytic *Plasmodium falciparum* malaria pigment with disease severity, clinical manifestations, and prognosis in severe malaria," *m. J. Trop. Med. Hyg.*, 69:253-259, 2003.

Maisel et al., "Rapid measurement of B-type natriuretic peptide in the emergency diagnosis of heart failure," *NE J. Med.*, 347(3):161-167, 2002.

Malamud, "Saliva as a diagnostic fluid," *British Medical Journal*, 305(6847):207-208, 1992.

Mandel, "A contemporary view of salivary research," *Critical Reviews in Oral Biology & Medicine*, 4(304):599-604, 1993.

Margolis et al., "Leukocyte Count as a Predictor of Cardiovascular Events and Mortality in Postmenopausal Women: The Women's Health Initiative Observational Study," *Archives of Internal Medicine*, 165:500-508, 2005.

Manila et al., "Association between dental health and acute myocardial infarction," *Bmj*, 298(6676):779-81, 1989.

Mayr et al., "Proteomics-based development of biomarkers in cardiovascular disease—Mechanistic, clinical, and therapeutic insights," *Molecular & Cellular Proteomics*, 5(10):1853-1867, 2006.

McCarley, R.L. et al., "Resist-Free Patterning of Surface Architectures in Polymer-Based Microanalytical Devices," *J.Am.Chem.Soc.*, vol. 127, published on the web Dec. 30, 2004, pp. 842-843.

McDevitt, "Electronic Taste Chip Research," presented in Bethesda, MD, Nov. 12, 2001.

McNeely et al., "Sample Processing with Hydrophobic Microfluidics," *J. Assoc. Lab. Automation*, 4:1-7, 1999.

Meathrel et al., "The effects of hydrophilic adhesives on sample flow," *IVD Technology*, 2001.

Meier-Ewert et al., "Absence of diurnal variation of C-reactive protein concentrations in healthy human subjects," *Clinical Chemistry*, 47:426-430, 2001.

Mellors et al., "Plasma Viral Load and CD4$^+$Lymphocytes as Prognostic Markers of HIV-1 Infection," *Ann. Intern Med.*, 126:946-954, 1997.

Mellors et al., "Prognosis in HIV-1 Infection Precited by the Quantity of Virus in Plasma," *Science*, 272:1167-1170, 1996.

Mellors et al., "Quantitation of HIV-1 RNA in Plasma Predicts outcome after Seroconversion," *Ann. Intern. Med.*, 122:573-579, 1995.

Michael et al., "Making sensors our of disarray: optical sensory Microarray," *SPIE*, 3270:34-41, 1998.

Morrison, "Time resolved detection of energy transfer: Theory and application to immunoassays," *Anal. Biochem.*, 174:101-120, 1998.

Morrow et al., "Ability of minor elevations of troponins I and T to predict benefit from an early invasive strategy in patients with unstable angina and non-ST elevation myocardial infarction: results from a randomized trial," *Jama-J. Amer. Med. Assoc.*, 286(19):2405-2412, 2001.

Morrow et al., "C-reactive protein is a potent predictor of mortality independently of and in combination with troponin T in acute coronary syndromes: a TIMI 11A substudy. Thrombolysis in Myocardial Infar," *Journal of the American College of Cardiology*, 31 : 1460-1465, 1998.

Mullis and Faloona, "Specific synthesis of DNA in vitro via a polymerase-catalyzed chain reaction," *Methods Enzymol.*, 155:335-350, 1987.

Mullis et al., "Specific enzymatic amplification of DNA in vitro: the polymerase chain reaction," *Cold Springs Harbor Symp. Quant. Biol.*, 51:263-273, 1986.

Murakami et al., "Sugar Sensing Utilizing Aggregation Properties of Boronic-acid-appended Porphyrins and Mettalloporphyrins," *J. Chem. Soc. Perkin Trans 2*, 975-981, 1994.

Murukami et al., "Sugar sensing utilizing aggregation properties of a boronic-acid-appended porphyrin," *Tetrahedron Lett.*, 34:6273-6276, 1993.

Nadal et al., "Prospective evaluation of amplification-boosted ELISA for heat-denatured p24 antigen for diagnosis and monitoring of pediatric human immunodeficiency virus type 1 infection," *J. Infect. Dis.*, 180:1089-1095, 1999.

Nagasaki et al., "Attempts to change the color of dye molecules by saccharides," *Tetrahedron Lett.*, 35(14):2201-2204, 1994.

Nahmias et al., "Thymic dysfunction and time of infection predict mortality in human immunodeficiency virus-infected infants. CDC Perinatal AIDS Collaborative Transmission Study Group," *J. Infect. Dis.*, 178:680-685, 1998.

Nairn et al., "Changes in leukocyte subsets: clinical implications for children with chronic renal failure," *Pediatr. Nephrol.*, 20:190-196, 2005.

Nakashima et al., "Sugar-Assisted Chirality Control of Tris(2,2'-bipyridine)-Metal Complexes," *Chem. Lett.*, 23(7):1267-1270, 1997.

Napoli et al., "Microarray analysis: a novel research tool for cardiovascular scientists and physicians," *Heart*, 89(6):597-604, 2003.

Nasir et al., "Relationship of monocyte count and peripheral arterial disease: results from the National Health and Nutrition Examination Survey 1999-2002," *Arterioscler Thromb Vasc*, 25:1966-1971, 2005.

Nicholson et al., "1997 Revised Guidelines for Performing CD4+ T-Cell Determinations in Persons Infected with Human Immunodeficiency Virus (HIV)," *Centers for Disease Control and Prevention Morbidity and Mortality Weekly Report*, 46:1-29, 1997.

Nicholson et al., "Use of CD45 fluorescence and side-scatter characteristics for gating lymphocytes when using the whole blood lysis procedure and flow cytometry," *Cytometry* (*Communications in Clinical Cytometry*), 26:16-21, 1996.

Niikura et al., "Chemosensor ensemble with selectivity for inositol-trisphosphate," *J. Am. Chem. Soc.*, 120:8533-8534, 1998.

Nogueira et al., "Characterization of salivary immunoglobulin A responses in children heavily exposed to the oral bacterium *Streptococcus mutans*: influence of specific antigen recognition in infection," *Infect. Immun.*, 73(9):5675-84, 2005.

O'Donnel, "Age-specific relationship between CD14 and atopy in a cohort assessed from age eight to twenty-five," published on Nov. 14, 2003, as doi:10.1164/rccm.200302-278OC.

O'Gorman et al., "Adoption of Single-Platform Technologies for Enumeration of Absolute T-Lymphocyte Subsets in Peripheral Blood," *Clin. Diag. Lab. Immunol.*, 7:333-335, 2000.

O'Gorman, "Evaluation of single-platform technologies for absolute CD4+ and CD8+ cells," *Conference on the Laboratory Science of HIV*, 97-111, 1998.

Office Communication, issued in European Application No. 00975164.5, dated Jun. 4, 2003.

Office Communication, issued in European Application No. 00975164.5, dated Feb. 11, 2005.

Office Communication, issued in European Application No. 01905306.5, dated Jan. 23, 2003.

Office Communication, issued in European Application No. 01905306.5, dated Feb. 16, 2004.

Office Communication, issued in European Application No. 02713535.9, dated Oct. 6, 2005.

Office Communication, issued in European Application No. 03726746.9, dated Jun. 19, 2008.

Office Communication, issued in European Application No. 05723785, dated Jun. 17, 2008.

Office Communication, issued in European Patent Application No. EP 05 723 785.1, dated Dec. 30, 2009.

Office Communication, issued in Japan Patent Application No. 2002-561913, dated Jan. 15, 2008.

Office Communication, issued in U.S. Appl. No. 09/775,343, dated Mar. 13, 2007.

Office Communication, issued in U.S. Appl. No. 09/775,343, dated Aug. 30, 2006.

Office Communication, issued in U.S. Appl. No. 09/775,343, dated Dec. 30, 2005.

Office Communication, issued in U.S. Appl. No. 09/775,343, dated Jun. 3, 2005.

Office Communication, issued in U.S. Appl. No. 09/775,343, dated Nov. 22, 2004.

Office Communication, issued in U.S. Appl. No. 09/775,343, dated May 10, 2004.

Office Communication, issued in U.S. Appl. No. 09/775,344, dated Apr. 5, 2005.

Office Communication, issued in U.S. Appl. No. 09/775,344, dated Sep. 10, 2004.

Office Communication, issued in U.S. Appl. No. 09/775,344, dated Apr. 16, 2004.

Office Communication, issued in U.S. Appl. No. 10/072,800, dated Dec. 29, 2005.
Office Communication, issued in U.S. Appl. No. 10/072,800, dated Jun. 28, 2005.
Office Communication, issued in U.S. Appl. No. 10/072,800, dated Mar. 28, 2005.
Office Communication, issued in U.S. Appl. No. 10/427,744, dated Jun. 22, 2009.
Office Communication, issued in U.S. Appl. No. 10/427,744, dated Nov. 7, 2008.
Office Communication, issued in U.S. Appl. No. 10/427,744, dated Apr. 30, 2008.
Office Communication, issued in U.S. Appl. No. 10/427,744, dated Aug. 8, 2007.
Office Communication, issued in U.S. Appl. No. 10/427,744, dated Nov. 3, 2006.
Office Communication, issued in U.S. Appl. No. 10/427,744, dated Apr. 26, 2006.
Office Communication, issued in U.S. Appl. No. 10/427,744, dated Jan. 12, 2006.
Office Communication, issued in U.S. Appl. No. 10/470,646, dated Sep. 15, 2009.
Office Communication, issued in U.S. Appl. No. 10/470,646, dated Dec. 24, 2008.
Office Communication, issued in U.S. Appl. No. 10/470,646, dated Jun. 13, 2008.
Office Communication, issued in U.S. Appl. No. 10/522,499, dated Aug. 7, 2009.
Office Communication, issued in U.S. Appl. No. 10/522,499, dated Jan. 22, 2009.
Office Communication, issued in U.S. Appl. No. 10/522,499, dated Jun. 20, 2008.
Office Communication, issued in U.S. Appl. No. 10/544,864, dated Nov. 24, 2009.
Office Communication, issued in U.S. Appl. No. 10/544,864, dated Mar. 19, 2009.
Office Communication, issued in U.S. Appl. No. 10/544,864, dated Sep. 30, 2008.
Office Communication, issued in U.S. Appl. No. 10/544,864, dated Aug. 18, 2008.
Office Communication, issued in U.S. Appl. No. 10/544,864, dated Jan. 25, 2008.
Office Communication, issued in U.S. Appl. No. 10/544,864, dated Sep. 27, 2007.
Zolg, "The proteomic search for diagnostic biomarkers: lost in translation?," *Molecul. Cell. Proteomics*, 5(10): 1720-1726, 2006.
Office Communication, issued in U.S. Appl. No. 10/544,954, dated Feb. 10, 2009.
Office Communication, issued in U.S. Appl. No. 10/544,954, dated Jul. 15, 2009.
Office Communication, issued in U.S. Appl. No. 10/924,285, dated Oct. 5, 209.
Office Communication, issued in U.S. Appl. No. 10/924,285, dated Nov. 25, 2008.
Office Communication, issued in U.S. Appl. No. 10/924,285, dated Oct. 6, 2008.
Office Communication, issued in U.S. Appl. No. 11/010,816, dated Aug. 14, 2009.
Office Communication, issued in U.S. Appl. No. 11/010,816, dated May 28, 2008.
Office Communication, issued in U.S. Appl. No. 11/010,816, dated Aug. 27, 2007.
Office Communication, issued in U.S. Appl. No. 11/010,816, dated Dec. 1, 2006.
Office Communication, issued in U.S. Appl. No. 11/010,816, dated May 4, 2006.
Office Communication, issued in U.S. Appl. No. 11/010,816, dated Nov. 17, 2005.
Office Communication, issued in U.S. Appl. No. 11/020,442, dated Jul. 21, 2009.
Office Communication, issued in U.S. Appl. No. 11/020,442, dated May 5, 2009.
Office Communication, issued in U.S. Appl. No. 11/020,442, dated Jun. 17, 2008.
Office Communication, issued in U.S. Appl. No. 11/020,442, dated Oct. 31, 2007.
Office Communication, issued in U.S. Appl. No. 11/020,442, dated Feb. 6, 2007.
Office Communication, issued in U.S. Appl. No. 11/020,442, dated May 11, 2006.
Office Communication, issued in U.S. Appl. No. 11/020,442, dated Nov. 22, 2005.
Office Communication, issued in U.S. Appl. No. 11/020,443, dated May 28, 2009.
Office Communication, issued in U.S. Appl. No. 11/020,443, dated Jul. 8, 2008.
Office Communication, issued in U.S. Appl. No. 11/020,443, dated Nov. 13, 2007.
Office Communication, issued in U.S. Appl. No. 11/020,443, dated Dec. 19, 2006.
Office Communication, issued in U.S. Appl. No. 11/020,443, dated Sep. 28, 2006.
Office Communication, issued in U.S. Appl. No. 11/020,443, dated Dec. 29, 2005.
Office Communication, issued in U.S. Appl. No. 11/020,443, dated Oct. 19, 2005.
Office Communication, issued in U.S. Appl. No. 11/021,123, dated Jan. 8, 2009.
Office Communication, issued in U.S. Appl. No. 11/021,123, dated Apr. 17, 2008.
Office Communication, issued in U.S. Appl. No. 11/021,123, dated Sep. 4, 2007.
Office Communication, issued in U.S. Appl. No. 11/021,123, dated Nov. 3, 2006.
Office Communication, issued in U.S. Appl. No. 11/021,123, dated Feb. 7, 2006.
Office Communication, issued in U.S. Appl. No. 11/022,176, dated May 20, 2009.
Office Communication, issued in U.S. Appl. No. 11/022,176, dated Jun. 16, 2008.
Office Communication, issued in U.S. Appl. No. 11/022,176, dated Nov. 30, 2007.
Office Communication, issued in U.S. Appl. No. 11/022,176, dated Mar. 16, 2007.
Office Communication, issued in U.S. Appl. No. 11/022,176, dated Jun. 13, 2006.
Office Communication, issued in U.S. Appl. No. 11/022,176, dated Dec. 20, 2005.
Office Communication, issued in U.S. Appl. No. 11/022,176, dated Sep. 7, 2005.
Office Communication, issued in U.S. Appl. No. 11/022,219, dated Jul. 22, 2009.
Office Communication, issued in U.S. Appl. No. 11/022,219, dated Dec. 5, 2008.
Office Communication, issued in U.S. Appl. No. 11/022,219, dated May 28, 2008.
Office Communication, issued in U.S. Appl. No. 11/022,219, dated Jul. 12, 2007.
Office Communication, issued in U.S. Appl. No. 11/022,219, dated Oct. 26, 2006.
Office Communication, issued in U.S. Appl. No. 11/022,219, dated Feb. 9, 2006.
Office Communication, issued in U.S. Appl. No. 11/022,365, dated May 27, 2009.
Office Communication, issued in U.S. Appl. No. 11/022,365, dated Oct. 28, 2008.
Office Communication, issued in U.S. Appl. No. 11/022,365, dated Apr. 21, 2008.
Office Communication, issued in U.S. Appl. No. 11/022,365, dated Aug. 24, 2007.
Office Communication, issued in U.S. Appl. No. 11/022,365, dated Mar. 15, 2007.
Office Communication, issued in U.S. Appl. No. 11/022,365, dated Aug. 9, 2006.

Office Communication, issued in U.S. Appl. No. 11/039,054, dated Feb. 25, 2008.
Office Communication, issued in U.S. Appl. No. 11/039,054, dated Jun. 21, 2007.
Office Communication, issued in U.S. Appl. No. 11/039,054, dated Oct. 11, 2006.
Office Communication, issued in U.S. Appl. No. 11/039,054, dated May 18, 2006.
Office Communication, issued in U.S. Appl. No. 11/039,054, dated Oct. 18, 2005.
Office Communication, issued in U.S. Appl. No. 11/746,941, dated Dec. 3, 2009.
Office Communication, issued in U.S. Appl. No. 11/746,941, dated Mar. 17, 2009.
Office Communication, issued in U.S. Appl. No. 11/746,941, dated Sep. 18, 2008.
Office Communication, issued in U.S. Appl. No. 11/746,965, dated Jun. 22, 2009.
Office Communication, issued in U.S. Appl. No. 11/746,956, dated Oct. 17, 2008.
Office Communication, issued in U.S. Appl. No. 09/616,731, dated Apr. 19, 2005.
Office Communication, issued in U.S. Appl. No. 09/616,731, dated Sep. 23, 2004.
Office Communication, issued in U.S. Appl. No. 09/616,731, dated Jun. 28, 2004.
Office Communication, issued in U.S. Appl. No. 11/970,985, dated Dec. 1, 2009.
Office Communication, issued in U.S. Appl. No. 09/287,248, dated Feb. 24, 2004.
Office Communication, issued in U.S. Appl. No. 09/287,248, dated Aug. 18, 2003.
Office Communication, issued in U.S. Appl. No. 09/287,248, dated Mar. 11, 2003.
Office Communication, issued in U.S. Appl. No. 09/287,248, dated Aug. 12, 2002.
Office Communication, issued in U.S. Appl. No. 09/287,248, dated May 2, 2002.
Office Communication, issued in U.S. Appl. No. 09/287,248, dated Jan. 2, 2002.
Office Communication, issued in U.S. Appl. No. 09/287,248, dated May 9, 2001.
Office Communication, issued in U.S. Appl. No. 09/354,882, dated Jan. 17, 2003.
Office Communication, issued in U.S. Appl. No. 09/354,882, dated May 8, 2002.
Office Communication, issued in U.S. Appl. No. 09/354,882, dated Oct. 3, 2001.
Office Communication, issued in U.S. Appl. No. 09/616,355, dated Aug. 13, 2002.
Office Communication, issued in U.S. Appl. No. 09/616,355, dated Mar. 15, 2002.
Office Communication, issued in U.S. Appl. No. 09/616,482, dated Oct. 3, 2001.
Office Communication, issued in U.S. Appl. No. 09/616,482, dated Mar. 27, 2002.
Office Communication, issued in U.S. Appl. No. 09/616,482, dated Aug. 1, 2002.
Office Communication, issued in U.S. Appl. No. 09/775,048, dated Feb. 5, 2003.
Office Communication, issued in U.S. Appl. No. 09/775,048, dated Sep. 17, 2002.
Office Communication, issued in U.S. Appl. No. 09/775,048, dated Feb. 6, 2002.
Office Communication, issued in U.S. Appl. No. 09/775,340, dated Apr. 22, 2003.
Office Communication, issued in U.S. Appl. No. 09/775,340, dated Oct. 25, 2002.
Office Communication, issued in U.S. Appl. No. 09/775,340, dated Jul. 29, 2002.
Office Communication, issued in U.S. Appl. No. 09/775,342, dated Aug. 13, 2003.
Office Communication, issued in U.S. Appl. No. 09/775,342, dated Feb. 14, 2003.
Office Communication, issued in U.S. Appl. No. 09/775,342, dated Oct. 2, 2002.
Office Communication, issued in U.S. Appl. No. 09/775,353, dated Oct. 2, 2002.
Office Communication, issued in U.S. Appl. No. 09/775,353, dated Feb. 5, 2002.
Office Communication, issued in U.S. Appl. No. 12/104,303, dated Sep. 23, 2009.
Or et al., "Capillarity," reproduced from Adamson AW, Physical Chemistry of Surfaces, $5^{th}$ ed., pp. 155-164, 1990.
Pabo et al., "Transcription factors: structural families and principles of DNA recognition.," Annu. Rev. Biochem., 61:1053-1095, 1992.
Palmerini et al., "Preprocedural levels of C-reactive protein and leukocyte counts predict 9-month mortality after coronary angioplasty for the treatment of unprotected left main coronary artery stenosis," Circulation, 112:2332-2338, 2005.
Poncelet et al., "Surface CD4 density remains constant on lymphocytes of HIV-infected patients in the progression of disease," Res. Immunol., 142:291-298, 1991.
Potyrailo et al., "Optical time-of-flight chemical detection: Absorption-modulated fluorescence for spatially resolved analyte mapping in a bidirectional distributed fiber-optic sensor," Analytical Chemistry, 70(16):3407-3412, 1998.
Quilici et al., "Circulating endothelial cell count as a diagnostic marker for non-ST-elevation acute coronary syndromes," Circulation, 110:1586-1591, 2004.
Reynes et al., "CD4+ T cell surface CCR5 density as a determining factor of virus load in persons infected with human immunodeficiency virus type 1," J. Infect. Dis., 181:927-932, 2000.
Ricco et al., "Surface acoustic wave chemical sensor arrays: New chemically sensitive interfaces combined with novel cluster analysis to detect volatile organic compounds and mixtures," Accounts of Chemical Research, 31(5):289-296,1998.
Rich et al., "Lymphocyte phenotyping in infants: maturation of lymphocyte subpopulations and the effects of HIV infection," Clin. Immunol. Immunopathol., 85:273-281, 1997.
Ridker et al., "Comparison of C-reactive protein and low-density lipoprotein cholesterol levels in the prediction of first cardiovascular events," New England Journal of Medicine, 347:1557-1565, 2002.
Ridker et al., "C-reactive protein and other markers of inflammation in the prediction of cardiovascular disease in women," The New England Journal of Medicine, 342(12):836-843, 2000.
Ridker et al., "C-reactive protein levels and outcomes after statin therapy," New England Journal of Medicine, 352:20-28, 2005.
Ridker et al., "Inflammation, pravastatin, and the risk of coronary events after myocardial infarction in patients with average cholesterol levels. Cholesterol and Recurrent Events (CARE) Investigators," Circulation, 98:839-844, 1998.
Robinson et al., "An analysis of the normal ranges of lymphocyte subpopulations in children aged 5-13 years," Eur. J Pediatr., 155:535-539, 1996.
Rodriguez et al., "A Microchip CD4 Counting Method for HIV Monitoring in Resource-Poor Settings,"Plos. Medicine, 2(7):663-672, 2005.
Rodriguez et al., "Development of Affordable and Portable HIV RNA and CD4 Diagnostics Tests Using Microchips," presented at AIDS 2002 Barcelona, XIV International AIDS Conference, 2002.
Rosano, "Increased C-reactive protein levels in women at increased cardiovascular risk predict one-year events only when associated with increased Interleukin-6 levels," Journal of the American College of Cardiology, Supplement A, 39:273A, 2002.
Sabatine et al., "Multimarker approach to risk stratification in non-ST elevation acute coronary syndromes: simultaneous assessment of troponin I, C-reactive protein, and B-type natriuretic peptide," Circulation, 105(15):1760-1763, 2002.
Saiki et al., "Enzymatic Amplification of .beta.-Globin Genomic Sequences and Restriction Site Analysis for Diagnosis of Sickle Cell Anemia," Science, 230:1350-1354, 1985.
Salvkin, "Toward molecularly based diagnostics for the oral cavity," Jounal of the American Dental Association, 129(8): 1138-1143, 1998.

Sanchez-Ramon et al., "Low Blood CD8+ T-Lymphocytes subpopulations in children aged 5-13 years," *Pediatrics*, 111:168-175, 2003.

Sandanayake et al., "Novel molecular sensors for saccharides based on the interaction of boronic acid and amines: saccharide sensing in neutral water," *J. Chem. Soc. Chem. Commun.*, 1083-1084, 1994.

Sandanayake et al., "Specific recognition of disaccharides by trans-3,3'-stilbenediboronic acid: rigidification and fluoresecence enhancement of the stilbene skeleton upon formation of a sugar—stilbene macrocycle," *J. Chem. Soc. Chem. Commun.*, 14:1621-1622, 1994.

Savoy et al., "Solution-Based Analysis of Multiple Analytes by a Sensor Array: Toward the Development of an Electronic Tongue," *SPIE Conference on Chemical Microsensors and Applications*, SPIE vol. 3539, Boston, MA, Nov. 4, 1998.

Schmidt et al., "Type a botulinum neurotoxin proteolytic activity: development of competitive inhibitors and implicatins for substrate specificity at the $S_1'$ binding subsite," *FEBS Lett.*, 435:61-64, 1998.

Schnizlein-Bick et al., "Evaluation of TruCount Absolute-Count Tubes for Determining CD4 and CD8 Cell Nos. In Human Immunodeficiency Virus-Positive Adults," *Clin. Diagnostic Lab. Immunol.*, 7:336-343, 2000.

Schutz et al., "Direct observation of ligand colocalization on individual receptor molecules," *Biophysical J.*, 74:2223-2226, 1998.

Shearer et al., "Lymphocyte subsets in healthy children from birth through 18 years of age: The Pediatric AIDS Clinical Trails Group P1009 study," *J. Allergy Clin. Immunol.*, 112:973-980, 2003.

Sherman et al., "CD4+ T cell enumeration in HIV infection with limited resources," *J. Immunol. Methods*, 222:209-217, 1999.

Shinkai et al., "Molecular recognition of mono- and di-saccharides by phenylboronic acids in solvent extraction and as a monolayer," *J. Chem Soc. Chem. Commun.*, 15:1039-1041, 1991.

Shiomi et al., "Specific complexation of glucose with a diphenylmethane-3,3-diboronic acid derivative: correlation between the absolute configuration of mono- and di-saccharides and the circular dichroic activity of the complex," *J. Chem. Soc. Perkin Trans I*, 2111-2117, 1993.

Shone et al., "Peptide substrate specificity and properties of the zincendopetidase activity of botulinum type B neurotoxin," *Eur. J. Biochem.*, 225:263-270, 1994.

Soleihac et al., "A sensitive and rapid fluorescence-based assay for determination of tetnus toxin peptidase activity," *Anal. Biochem.*, 241:120-127, 1996.

St. John et al., "Interleukin 6 and interleukin 8 as potential biomarkers for oral cavity and oropharyngeal squamous cell carcinoma," *Arch. Otolaryngol. Head Neck Surg.*, 130(8):929-35, 2004.

Stanley, "UT Scientists engineer a tiny arbiter of taste," *Austin-American Statesman*, Jul. 26, 1998.

Stimpson et al., "Real-time detection of DNA hybridization and melting on oligonucleotide arrays by using optical wave guides," *Proc. Natl. Acad. Sci USA.*, 92:6379-93, 1995.

Strahlendorf et al., "Peripheral blood monocyte count as an aid in optimizing progenitor collection in children," *Pediatr. Blood Cancer*, 43:610-611. 2004.

Supplementary European Search Report, issued in International Application No. EP 03 76 5999, dated Jul. 14, 2006.

Suzuki et al., "Quantitative detection of hepatitis C virus (HCV) RNA in saliva and gingival crevicular fluid of HCV-infected patients," *J. Clin. Microbiol.*, 43(9):4413-7, 2005.

Tatsumi, N. et al., "Practical Use of Automated White Cell Differential Analysis," *Horiba Technical Reports*, Jul. 31, 2002.

*The State of the World's Children 2005*, UICEF, 2004.

Tudos et al.," Trends in miniaturized total analysis systems for point-of-care testing in clinical chemistry," *Lab. Chip*, 1(2):83-95, 2001.

U.S. Appl. No. 10/522,926 entitled "Capture and Detection of Microbes by Membrane Methods," by McDevitt et al., filed Jan. 24, 2005.

U.S. Appl. No. 11/021,219 entitled "Pulsed Ion Source for Quadruple Mass Spectrometer and Method," by McCauley et al., filed Dec. 23, 2004.

U.S. Appl. No. 60/693,613 entitled "Analyte Detection Systems and Methods Including Self-Contained Cartridges with Detection Systems and Fluid Delivery Systems," by McDevitt et al., filed Jun. 24, 2005.

Vasan, "Biomarkers of cardiovascular disease: molecular basis and practical considerations," *Circulation*, 113(19):2335-2362, 2006.

Venugopal et al., "Macrophage conditioned medium induces the expression of C-reactive protein in human aortic endothelial cells: potential for paracrine/autocrine effect," *Amer. J. Pathol.*, 166(4):1265-1271, 2005.

Vickers et al., "Genotype at a promoter polymorphism of the interleukin-6 gene is associated with baseline levels of plasma C-reactive protein," *Cardiovascular Research*, 53:1029-1034, 2002.

Weigum et al., "Cell-based sensor for analysis of EGFR biomarker expression in oral cancer," *Lab on a Chip*, 7:995-1003, 2007.

White et al., "Rapid Analyte Recognition in a Device Based on Optical Sensors and the Olfactory System," *Anal. Chem.*, 68:2191-2202, 1996.

Written Opinion, issued in International Application No. PCT/US01/03240, dated Jan. 22, 2002.

Written Opinion, issued in International Application No. PCT/US03/23131, dated Feb. 24, 2004.

Written Opinion, issued in International Application No. PCT/USO4/03751, dated Aug. 20, 2004.

Written Opinion, issued in International Application No. PCT/US2005/006349, dated Aug. 30, 2005.

Written Opinion, issued in International Application No. PCT/US99/16162, dated May 2, 2000.

Wu et al., "Periodontal disease and risk of cerebrovascular disease: The first national health and nutrition examination survey and its follow-up study," *Arch. Intern. Med.*, 160(18):2749-2755, 2000.

Wu et al., "The Ligation Amplification Reaction (LAR)-Amplification of Specific DNA Sequences Using Sequential Round of Template-Dependent Ligation," *Genomics*, 4:560-569, 1989.

Yang et al., "Detection of picomolar levels of interleukin-8 in human saliva by SPR," *Lab Chip*, 5(10):1017-23, 2005.

Yip et al., "Levels and values of serum high-sensitivity C-reactive protein within 6 hours after the onset of acute myocardial infarction," *Chest*, 126:1417-1422, 2004.

Youil et al., "Detection of 81 of 81 known mouse beta-globin promoter mutations with T4 endonuclease-VII-The EMC Method," *Genomics*, 32:431-435, 1996.

Zhu et al., "ProCAT: a data analysis approach for protein microarrays," *Genome Biology*, 7(11):R11, 2006.

Canadian Office Action dated Oct. 5, 2012 in Canadian Patent Application 2,610,793.

Extended European Search Report dated Oct. 23, 2012 in European Patent Application No. 06 84 4118.

* cited by examiner

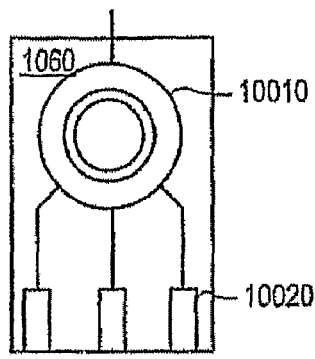 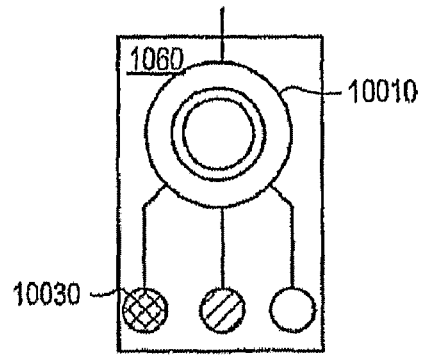
FIG. 22A  FIG. 22B
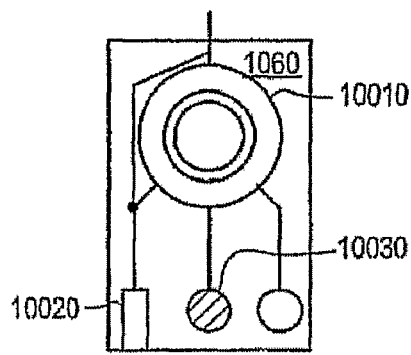 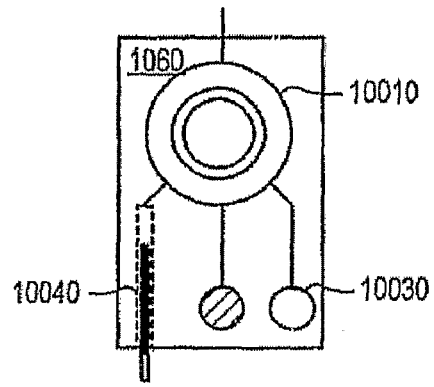
FIG. 22C  FIG. 22D
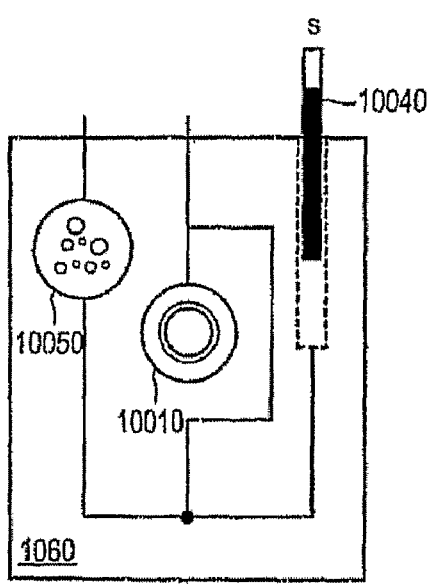 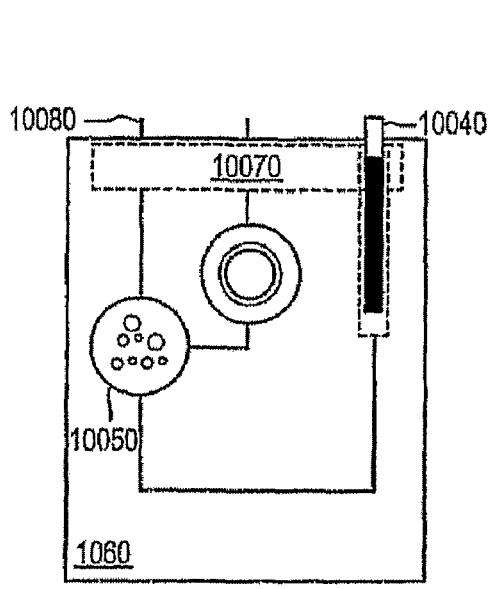
FIG. 23A  FIG. 23B

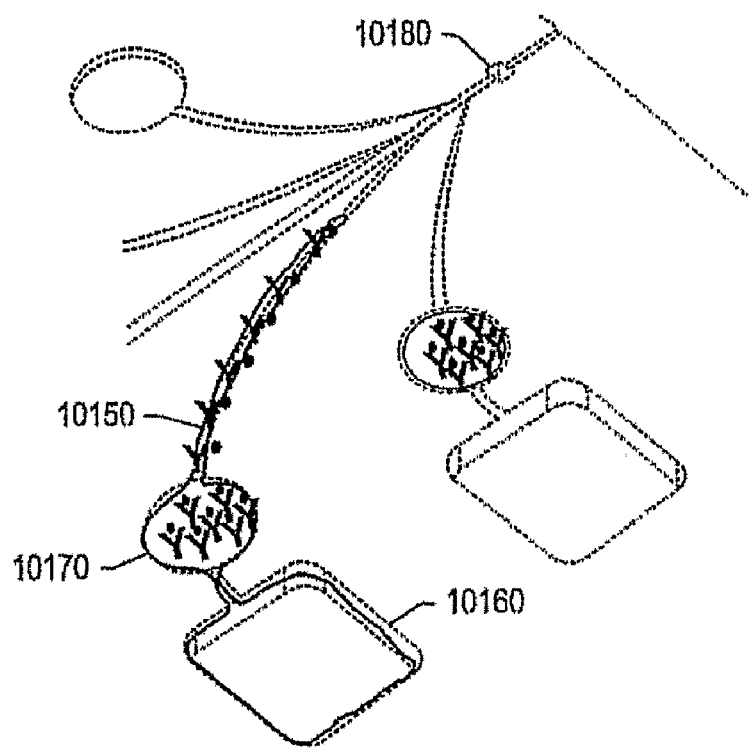
FIG. 27
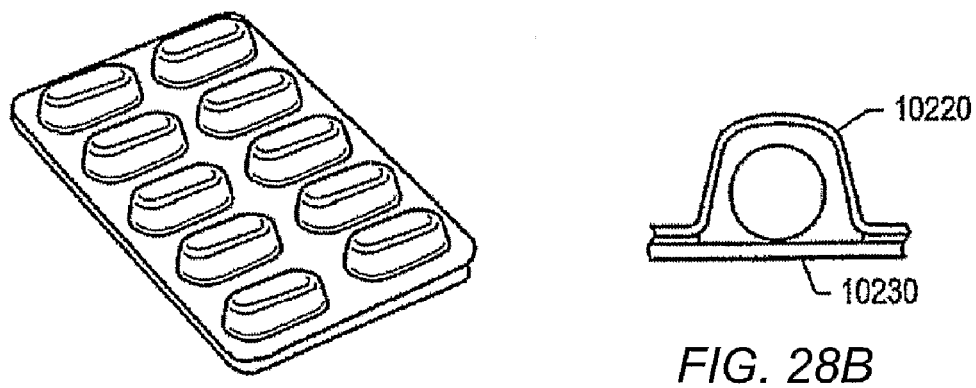
FIG. 28A
FIG. 28B

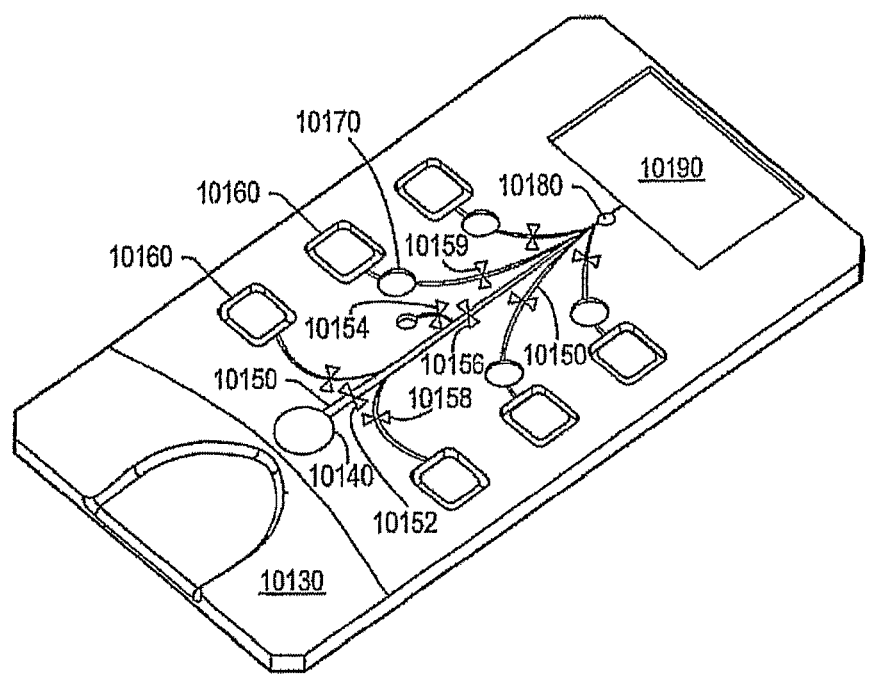
FIG. 29
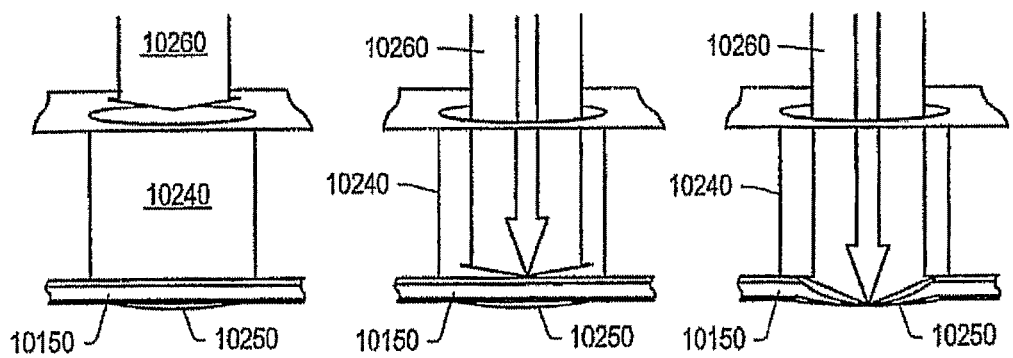
FIG. 30A  FIG. 30B  FIG. 30C

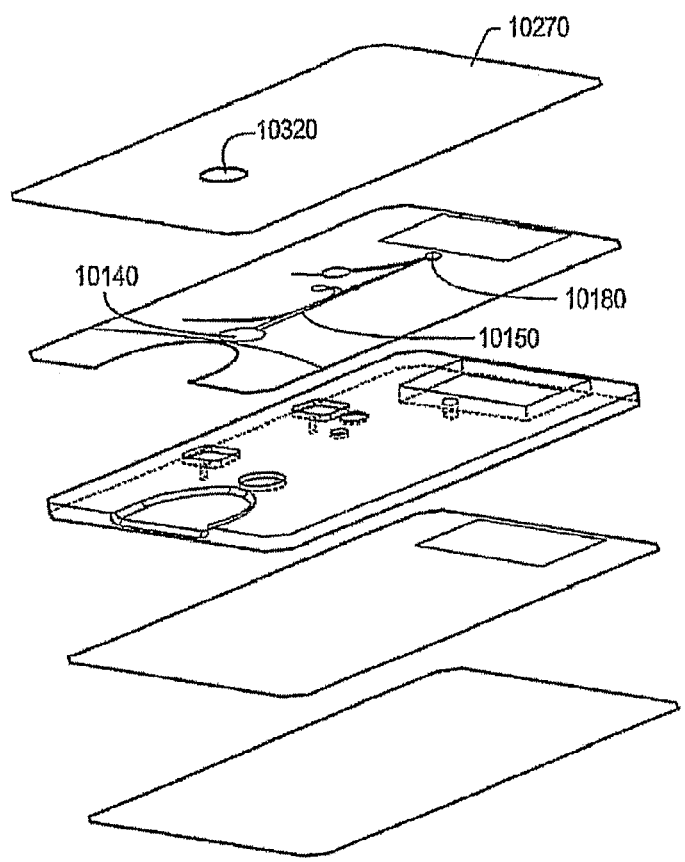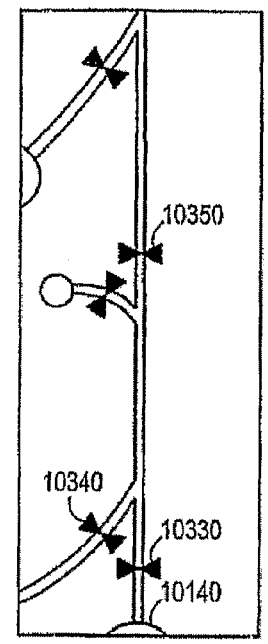
FIG. 35A
FIG. 35B

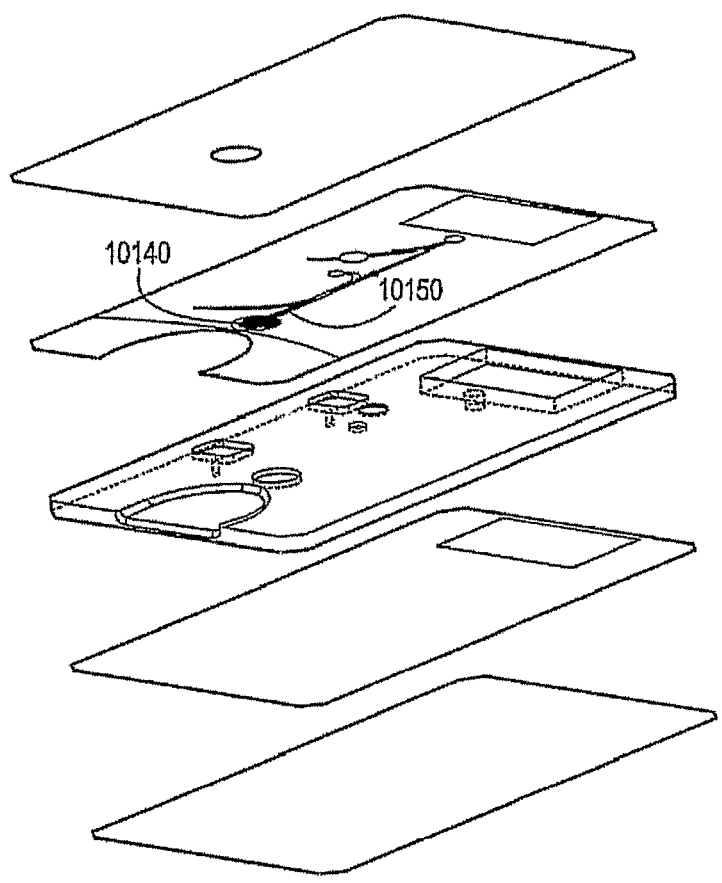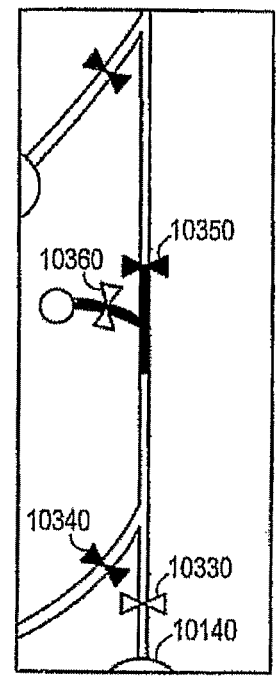
FIG. 36B
FIG. 36A

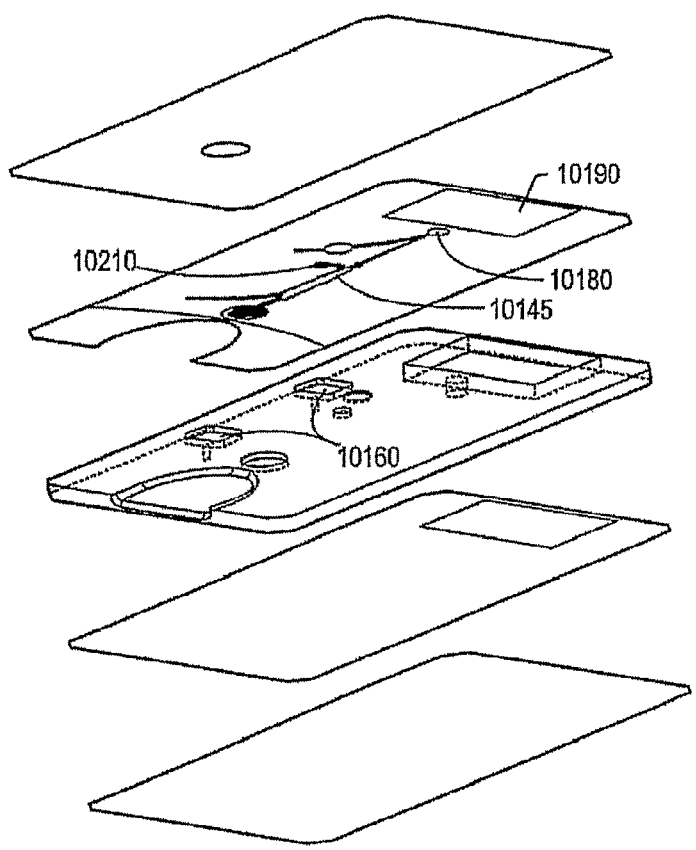
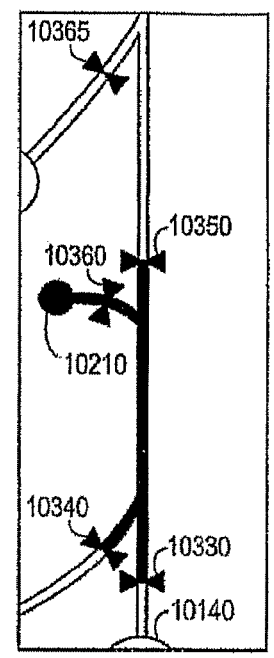
FIG. 37A
FIG. 37B

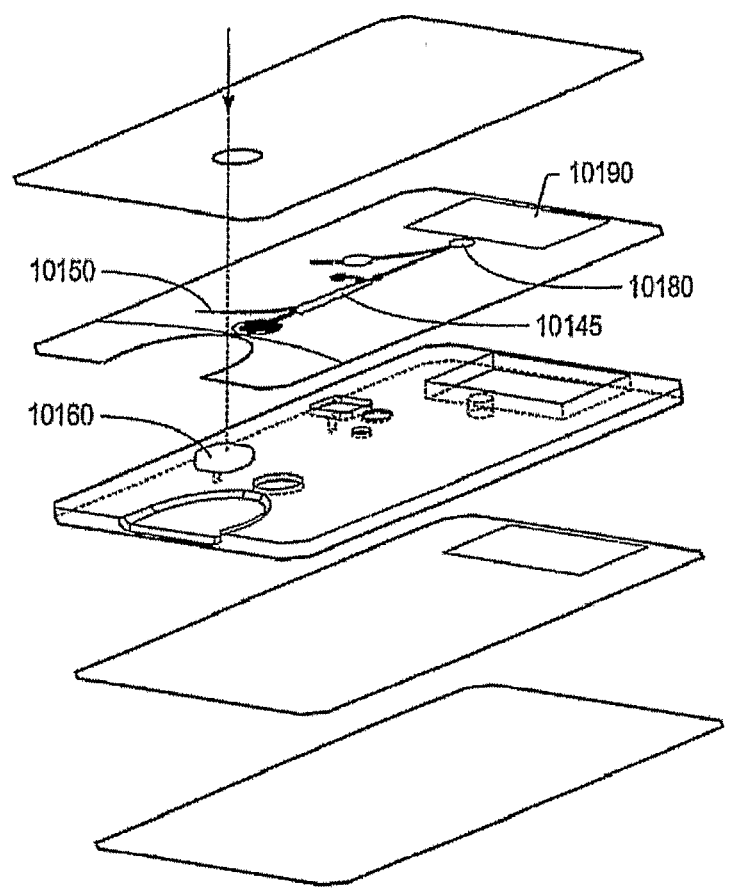
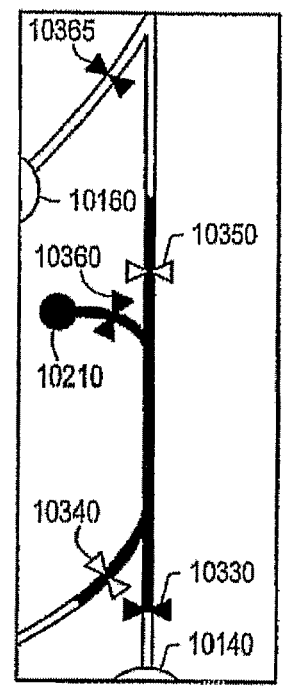
FIG. 38A
FIG. 38B

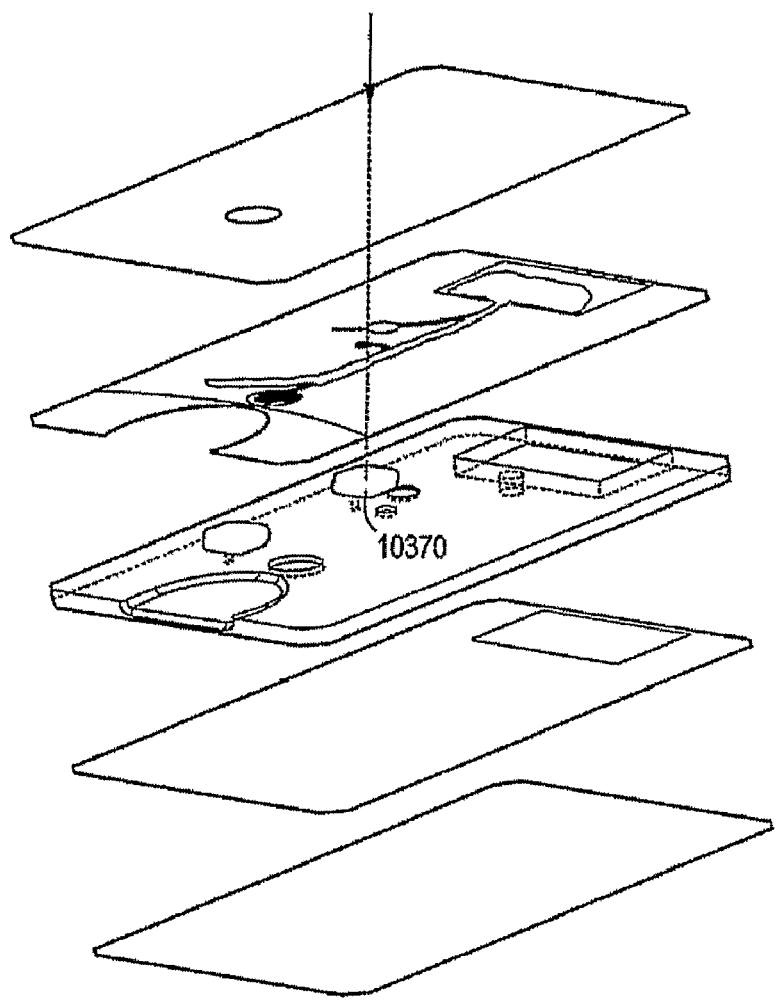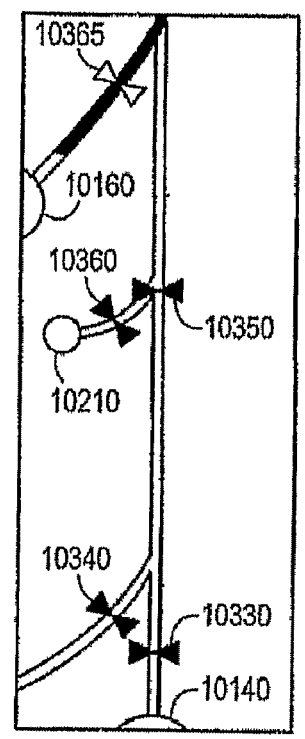
FIG. 41A
FIG. 41B

US 8,377,398 B2

METHODS AND COMPOSITIONS RELATED TO DETERMINATION AND USE OF WHITE BLOOD CELL COUNTS

PRIORITY CLAIM

This application is a national phase application under 35 U.S.C. §371 of International Application No. PCT/US2006/021209 filed May 31, 2006, which claims priority to U.S. Provisional Application No. 60/685,999 entitled "METHODS FOR MONITORING AND TRIGGERING HIV THERAPY," filed on May 31, 2005, both of which are incorporated herein by reference in their entirety.

BACKGROUND

1. Field of the Invention

The present invention generally relates to methods and compositions related to the determination and use of white blood cell counts.

2. Description of Related Art

White blood cell counts are routine medical tests used to diagnose a variety of disease processes, to follow the progression of a disease, or to monitor the effect of medical treatment. Low levels of white blood cells are associated, for example, with bone marrow failure, cytotoxicity, liver disease, and lupus, whereas high levels are associated, for example, with infectious diseases, inflammatory diseases, and leukemia, Differential white blood cell counts are also useful medical tests. Specific lymphocyte populations are elevated, for example, in HIV-infected subjects. The absolute count of CD4+ lymphocytes, for example, is used to determine when to commence antiretroviral therapy in subjects with HIV, and the percentage of CD4+ cells is widely used to determine pediatric care and treatment.

There are 2.2 billion children in the world, 1.9 billion of them living in developing countries, and about half of that number, living in poverty. (UNAIDS/WHO, 2005) In 2003, 10.6 million children, worldwide died before they were five (this number represents the entire population of children under five of France, Germany, Greece and Italy). Children under 15 get infected with HIV at the rate of one every minute. Ninety percent of the more than 5 million children who have been infected were born in Africa. Meanwhile, the number of cases is rising in other parts of the world. In the worst-affected countries, AIDS is now the biggest single cause of death among the under 5s, and is threatening to reverse years of hard-won progress in reducing child mortality. Thus, needed in the art are means of testing and evaluating white blood cell counts using simple, inexpensive devices.

Current methodology used to complete medical diagnostics, as well as environmental monitoring and detection of bioterrorism-related agents often require large and expensive instruments and highly specialized personnel found only in certain hospitals, laboratories or government agencies. Furthermore, these instruments are often restricted to a limited number of applications. For example, in the area of medical diagnostics, each instrument is very specialized and designed either to measure protein levels or to analyze cellular matter but, typically, may never do both. Additionally, each system is capable of analyzing only a few of the relevant markers of a disease, therefore adding another component to an already tedious and time consuming process that can vary from hours to days. Long delays can be generated between the time of the initial visit, diagnosis, and administration of treatment, potentially having detrimental effects on the prognosis of the disease.

SUMMARY

The present invention addresses a need in the art by providing a system for performing blood counts at the point of care, even in poor or underdeveloped regions. A system may include a sample collection device, an off-line sample processing unit, a fluid delivery system, a disposable cartridge, a cartridge self-positioning system, an optical platform, electronics, power supplies, computer processor(s), and/or software and firmware. In operation, a sample may be collected using the sample collection device. Sample collection devices may include needles, capillary tubes, pipettes, and/or vacutainers. A sample collection device may be configured to consume a portion of the sample collection device that contacts a sample. A sample collection device may include a sample pick-up pad configured to receive a sample and deliver the sample to the cartridge. A blood sample may be analyzed by introducing the blood sample into a disposable cartridge. Cell counts may be determined using at least a portion of the cells or cellular components as analytes. The analytes are collected and an amount and/or identity of cell surface markers or cell types that interact with binding agents and detectable labels are assessed.

The sample may be transported to a cartridge with the fluid delivery system. A sample may flow from the sample collection device to a sample reservoir in a cartridge. Reagents and/or buffers may be delivered to the sample reservoir. Reagents may be delivered by a reagent delivery system and/or contained in reagent reservoirs, reagent packs, and/or reagent pads. A sample reservoir may include a mixing chamber where a sample may react with reagents. An actuator coupled to the cartridge may drive fluid through the cartridge.

A cartridge may include a microsieve-based detection region. Light from an optical platform may pass onto a detection region and a detector in the optical platform may acquire images (e.g., visual or fluorescent) of the sample. The images may be processed and analyzed using software, algorithms, and/or neural networks.

The system optionally includes the use of defined populations of assay particles that are chemically sensitized to detect the presence of a specific analyte in a fluid by binding to the analyte. Chemically sensitizing a population of particles to detect an analyte may include coupling a binding agent for the analyte to the population of particles. Binding agents for analytes may include antibodies that bind to the analyte. The binding agents may be bound directly or indirectly with a detectable label. A plurality of detectable labels may be defined by different colors or optical spectra. Thus, the system may involve detecting a plurality of detectable labels in the same cell or in different cells or both.

Populations of cells may be mechanically captured on the surface of a microsieve in a cartridge. The cartridge may be configured to allow fluid flow through the microsieve. The cartridge may be coupled to an optical/digital acquisition system that may be configured to allow the visualization of cells captured thereon. Thus, the microsieve-equipped cartridge coupled to an optical/digital acquisition system may include a device that facilitates the digital/optical acquisition of fluorescent signals resulting from immunological reactions that take place in the cartridge.

In some embodiments, white blood cell populations in a sample can be detected by applying a sample to the cartridge with one or more microsieves and by applying one or more detectable labels from one or more detectable label locations in or on a cartridge to a least a portion of the white blood cells retained in or on the one or more microsieves.

In an embodiment, CD4+ lymphocytes in a sample can be assessed by applying a sample to a microsieve in or on a cartridge; applying a first detectable label to cells retained on a microsieve to label any CD4+ cells; applying one or more additional detectable labels to cells retained on the microsieve to label any T-cells, NK-cells, and B-cells retained on the microsieve (i.e., lymphocytes); providing a first image of the CD4+ cells; providing a second image of the lymphocytes; and assessing a number of CD4+ lymphocytes by assessing the number of cells labeled in the first image that are also labeled in the second image. In some embodiments, a percentage of CD4+ lymphocytes to total lymphocytes is assessed by comparing the number of cells labeled in both the first image and the second image to the number of cells labeled in the second image.

In an embodiment, detecting an analyte in a fluid may include forming a mixture of size- and color-coded particles (e.g., fluorescent microparticles) with the fluid. The particles may be coupled to a binding agent that interacts with the analyte. In an embodiment, the particle/fluid mixture may be passed across a microsieve in a cartridge. In an embodiment, the system may be configured to visualize the analyte captured on the microsieve. In an embodiment, detecting the analyte may include detecting spectroscopic signals from the particles captured on the microsieve.

BRIEF DESCRIPTION OF THE DRAWINGS

Features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 1A shows an image of all particles captured by a microsieve. FIG. 1B depicts the particles that would remain if a filter that allows only particles that are green to show is used. FIG. 1C depicts an image captured of only particles that exhibit color in the red portion of the spectrum. FIG. 1D shows the original image but with the particles that appear in the red portion of the spectrum subtracted from the image. FIG. 1E depicts an image of only the particles that exhibit color in the blue portion of the spectrum, using a binary mask to mask any pixels that include a blue component. FIG. 1F shows the original image but with the red binary mask and blue binary mask applied so that pixels including a red or blue component are excluded;

FIG. 5A depicts a representation of an image of cells obtained by exciting the green fluorophore detectable label with a light source, analyzing the signal generated by the excitation, and producing an image of the cells. FIG. 5B depicts a representation of an image of cells obtained by exciting the red fluorophore, analyzing the signal produced from excitation, and producing an image of these cells. FIG. 5C depicts a representation of an image that includes single labeled "green" cells, single labeled "red" cells, and double labeled cells, created by combining the images of FIGS. 5A and 5B.

FIG. 6A depicts an image of cells obtained by excitation of a green fluorophore bound to cells expressing CD4. FIG. 6B depicts an image of cells obtained by excitation of a red fluorophore attached to cells expressing CD3 or CD19. FIG. 6C depicts an image of red cells from which a total number of lymphocytes may be obtained. FIG. 6D depicts an image representing a filter that only allows green light to pass.

FIG. 8A depicts an embodiment of a disposable cartridge including reagent packs. FIG. 8B depicts an embodiment of a cartridge including reagent packs. FIG. 8C depicts embodiments of a combination of reagent reservoirs, reagent packs, and/or reagent pads positioned in a cartridge;

FIG. 18A is a schematic diagram that depicts lyophilized reagents disposed in a mixing chamber. FIG. 18B is a schematic diagram that depicts lyophilized reagents mixed with a sample upon introduction of the sample into the mixing chamber of the cartridge. FIG. 18C is a schematic diagram that depicts a mixture of a sample and reagents flowing out of the chamber to other parts of the cartridge based on the positioning of microfluidic valves in the cartridge;

FIG. 19A depicts a sample introduced through a sample introduction port. FIG. 19B depicts delivery of a sample to a microsieve, after switching of one or more microvalves. FIG. 19C depicts actuation of microvalve systems to allow passage of rinsing reagents through a microsieve;

FIG. 21A is a schematic diagram that depicts an embodiment of a cartridge accommodated with an inlet, outlet, and lateral flow outlet. FIG. 21B is a schematic diagram that depicts another embodiment of a cartridge with an inlet, outlet, and lateral flow outlet. FIG. 21C is a schematic diagram that depicts a cartridge made with a built-in waste reservoir;

FIGS. 22A-D depict different embodiments of channels for delivering fluids within a cartridge. FIG. 22A is a schematic diagram that depicts multiple channels created in a cartridge to allow the delivery to a detection system of a variety of reagents separately. FIG. 22B is a schematic diagram that depicts an embodiment of a cartridge in which a sample may be deposited or introduced to a chamber where it is drawn to a microsieve-based platform of a cartridge through capillary action, actuation, or pump action. FIG. 22C is a schematic diagram that depicts an embodiment of a cartridge that may include a combination of standard or customized connectors, and reagent chambers that may be actuated. FIG. 22D is a schematic diagram that depicts an embodiment of a cartridge with one or more connectors and/or chambers modified to receive a capillary collection tube that includes an analyte;

FIGS. 23A-B depicts different embodiments of cartridges that include a trap. FIG. 23A is a schematic diagram that depicts an embodiment of a cartridge that includes a trap, which is used to inhibit air from flowing to the detection system. FIG. 23B is a schematic diagram that depicts another embodiment of a cartridge that includes a trap, as well as a built-in removable waste reservoir and a lateral flow outlet directly coupled to the trap;

FIG. 24A is a schematic diagram that depicts an image of particles captured on a microsieve according to an embodiment, where polystyrene particles of the same size are distinguished on the basis of red fluorescence intensity. FIG. 24B depicts a line profile analysis of the particles in the boxed area of FIG. 24A;

FIG. 27 depicts an embodiment of a reagent reservoir and reagent pack in the cartridge depicted in FIG. 25;

FIG. 28A depicts an embodiment of a blister pack containing reagents;

FIG. 28B depicts a cross-sectional view of a blister of a blister pack;

FIG. 29 depicts an embodiment of valves positioned in the cartridge depicted in FIG. 25;

FIGS. 30A-30C depict views of the operation of a pinch valve. FIG. 30A is a schematic diagram that depicts an embodiment of a pinch valve that includes an opening in a cartridge. FIG. 30B is a schematic diagram that depicts an embodiment in which an actuator may be positioned in an opening of a cartridge above a channel after a cartridge is positioned in an instrument. FIG. 30C is a schematic diagram that depicts an embodiment in which an actuator may apply pressure on the channel such that fluid is inhibited from flowing through the channel;

FIG. 35A depicts an exploded view of an alternate embodiment of a cartridge that includes a sensor array;

FIG. 35B depicts an embodiment of an arrangement of valves in the cartridge of FIG. 35A;

FIG. 36A depicts an exploded view of an embodiment of the cartridge depicted in FIG. 35A as sample is introduced in the cartridge;

FIG. 36B depicts an embodiment of an arrangement of valves in a cartridge as sample is introduced in the cartridge;

FIG. 37A depicts an exploded view of an embodiment of the cartridge depicted in FIG. 35A after the sample is introduced into the channel;

FIG. 37B depicts an embodiment of an arrangement of valves in a cartridge after the sample is introduced into the channel;

FIG. 38A depicts an exploded view of an embodiment of the cartridge of FIG. 35A in which a reservoir is being actuated;

FIG. 38B depicts an embodiment of an arrangement of valves in a cartridge that allows a sample to be pushed towards a detection region using buffer released from a reservoir;

FIG. 41A depicts an exploded view of an embodiment of a cartridge; and

FIG. 41B depicts an embodiment of an arrangement of valves in a cartridge.

DETAILED DESCRIPTION

Figure 1A:
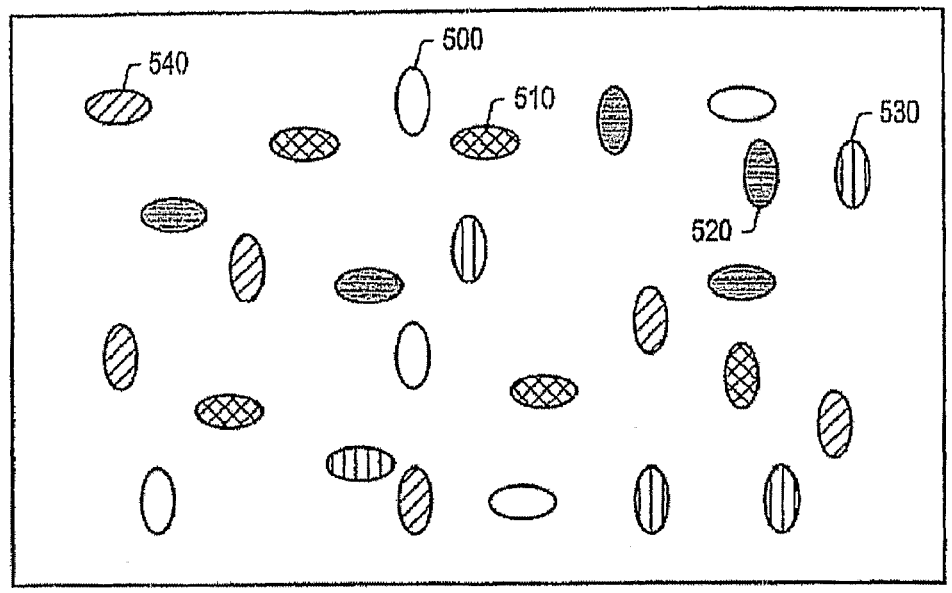
FIGS. 1A-1F depict a method of analysis of particles captured by a microsieve.

Herein we describe a system and method for differential assay of white blood cell counts. By "differential assay" is meant the analysis of one or more specific populations of white blood cells in a sample. The term "white blood cell" is used synonymously herein with leukocyte. Specific populations of white blood cells include, for example, all white blood cells, monocytes, neutrophils, lymphocytes, eosinophils, basophils, or any subgroup thereof or any combination thereof (e.g., a count of CD4 positive (CD4+) lymphocytes.

The system may generate patterns that are diagnostic for both individual analytes and mixtures of the analytes. As used herein, "analytes" refers to a population of white blood cells or surface receptors thereon. The system includes microsieves and binding agents. "Binding agents" are agents that specifically bind a target molecule or cell and include, for example, ligands or fragments thereof, antibodies or fragments thereof, aptamers (either DNA or RNA) or fragments thereof, phages (for example, from a phage display library) or fragments thereof, microspheres or beads. By specifically binding is meant that the binding agent recognizes and physically interacts with a selected target and does not significantly recognize and interact with other selected targets.

Provided herein is a cartridge for differential assay of white blood cell populations. The cartridge comprises a chamber; a microsieve (e.g., a membrane) positioned at least partially within the chamber, wherein pores of the microsieve are configured to retain white blood cells from a blood sample and to allow red blood cells to pass through the microsieve, and wherein an image can be obtained from the microsieve; three or more binding agents contained at least partially in or on the cartridge, wherein each binding agent differentially binds one or more populations of white blood cells; and two or more detectable labels contained at least partially in or on the cartridge, wherein at least one of the detectable labels binds at least one of the binding agents.

As used herein, the term "detectable label" is intended to mean any suitable agent, such as a chemical agent, that interacts with binding agents and allows the visualization of analyte/binding agent complexes. Detectable labels include, but are not limited to, enzymes, fluorophores, biotin, chromophores, radioisotopes, colored particles, electrochemical, chemical-modifying or chemiluminescent moieties. In some embodiments, a detectable label includes a fluorescent moiety. Common fluorescent moieties include fluorescein, cyanine dyes, coumarins, phycoerythrin, phycobiliproteins, dansyl chloride, TEXAS RED® and ALEXAFLUOR® dyes (Invitrogen-Molecular Probes, Inc., Eugene, Oreg.) and lanthanide complexes. Derivatives of these compounds also are included as common fluorescent moieties. The detection of the detectable label can be direct provided that the detectable label is conjugated to the binding agent of the system. Alternatively, the detection of the detectable label can be indirect. Thus, in some embodiments, a detectable label may bind indirectly to a binding agent by binding to a secondary agent that binds to the binding agent. Examples of secondary agents may include, but are not limited to DNA, RNA, proteins, enzymes, oligopeptides, oligonucleotides, antigens, and antibodies. In some embodiments, the secondary agent may be a polypeptide molecule that binds to a receptor or cell surface molecule. Alternatively, the secondary agent may include a secondary antibody directed against a receptor or cell surface molecule. In some embodiments, a method of detecting multiple analytes in a fluid may rely on immunological reactions that take place on the surface of the cells. In some cases tertiary or additional agents may be used. For example, a secondary or tertiary antibody may be coupled to the detectable label and the secondary or tertiary label would then be amplified as compared to a direct detection method.

"Detectable label is used interchangeably herein with "stain" or "label," and a "stained" or "labeled" cell refers to a cell that is bound directly or indirectly to a detectable label.

In some embodiments of the cartridge, at least one of the detectable labels is a fluorophore or a fluorescent microparticle (e.g., microsphere or bead). As used herein, the terms "fluorochrome" and "fluorphore" and the terms "microsphere' and "microparticle" are used interchangeably. Detectable labels include fluorescent microspheres or beads. Microspheres may be labeled with two or more fluorochromes mixed together in varying concentrations, such that each specific label has a specific concentration of each fluorochrome. It is the specific concentrations of the various fluorochromes together to provide a spectrum of labels that can be used to distinguish the various subsets of labeled microspheres. Thus, microspheres having detectably different labels may comprise the detectable labels used herein. See, e.g., WO 99/19515 and WO 99/37814, which are incorporated herein in their entirety for types of microspheres and methods of making and using same. For example, the microspheres can be polystyrene-divinylbenzene microspheres or latex microparticles (available, for example, from Invitrogen).

In some of the embodiments of the cartridge, a first binding agent binds CD2+ white blood cells, a second binding agent binds CD4+ white blood cells, and a third binding agent binds CD19+ white blood cells. Optionally, at least one of the binding agents is an antibody or a fragment thereof and, more particularly, the antibody optionally binds to a white blood cell surface receptor. Such surface receptors may be selected from the group including, but not limited to, CD2, CD3, CD4, CD8, CD16, CD19, CD45, and CD56.

In some embodiments the microsieve is a membrane. More particularly the microsieve may be a polycarbonate track-etched membrane.

Optionally, the cartridge further comprises a blood sample of a known volume. By "known volume" is meant a volume that is calculated or known prior to addition to the cartridge or a volume that can be calculated, measured, or metered once the sample is present in the cartridge.

In some embodiments, the cartridge further comprises a support structure positioned beneath the microsieve and at least partially within the chamber, wherein the support structure maintains the microsieve in a relatively planar orientation and allows filtered material to pass through the microsieve.

Further provided herein are methods of using the cartridge, For example, such a method comprises the steps of passing a blood sample from the subject through the cartridge under conditions that allow differential binding of the binding agents to populations of white blood cells in the sample and binding of the detectable labels to the binding agents to form white blood cell/binding agent/detectable label complexes; detecting the white blood cell/binding agent/detectable label complexes; optically imaging the populations of white blood cells to differentiate the white blood cell/binding agent/detectable label complexes; and assessing a percentage or absolute count of one or more populations of white blood cells based on the numbers or ratios of complexes that contain at least one of the detectable labels. Optionally the blood sample used in the methods taught herein is of a known volume.

In some embodiments of the methods taught herein, a first binding agent binds CD2+ white blood cells, a second binding agent binds CD4+ white blood cells, and a third binding agent binds CD19+ white blood cells. A first detectable label binds the first binding agent and the third binding agent, and a second detectable label binds the second binding agent. In these embodiments, a percentage of CD4+ lymphocytes and/or an absolute count of CD4+ lymphocytes may be assessed. For example, assessing the percentage of CD4+ lymphocytes includes assessing the number of complexes with the first detectable label (i.e., all cells labeled with the first detectable label) and the number of complexes with both the first detectable label and second detectable label (i.e., cells double labeled with the first and second detectable label). Assessing an absolute count of CD4+ lymphocytes comprises assessing the number of complexes with both the first detectable label and the second detectable label (i.e., detecting double labeled cells) in a blood sample of known volume.

In some embodiments of the methods taught herein, a first binding agent binds CD2+ white blood cells, a second binding agent binds CD4+ white blood cells, a third binding agent binds CD19+ white blood cells, and a fourth binding agent binds CD56+ white blood cells. A first detectable label binds the first binding agent, the third binding agent, and the fourth binding agent. A second detectable label binds the second binding agent. In this method, assessing a percentage of CD4+ lymphocytes comprises assessing the number of complexes with the first detectable label (i.e., all cells labeled with the first detectable label) and the number of complexes with both the first detectable label and second detectable label (i.e., double labeled cells). Assessing an absolute count of CD4+ lymphocytes comprises assessing the number of complexes with both the first detectable label and the second detectable label (i.e., double labeled cells) in blood sample of known volume.

In some embodiments of the method, a first binding agent binds CD3+ white blood cells, a second binding agent binds CD4+ white blood cells, a third binding agent binds CD19+ white blood cells, a fourth binding agent binds CD56+ white blood cells, and a fifth binding agent binds CD16+ white blood cells; wherein a first detectable label binds the first, third, fourth, and fifth binding agents, and a second detectable labels binds the second binding agents. Assessing a percentage of CD4+ lymphocytes using this method comprises assessing the number of complexes with the first detectable label and the number of complexes with both the first detectable label and second detectable label; whereas assessing an absolute count of CD4+ lymphocytes comprises assessing the number of complexes with both the first detectable label and the second detectable label in blood sample of known volume.

As used herein "conditions that allow differential binding of the binding agents to populations of white blood cells" means conditions in which at least some binding agents bind to one or more white blood cells. Such conditions do not require that all binding agents bind to white blood cells or that all white blood cells bind to a binding agent, rather that the conditions allow for specific binding interactions to occur. These conditions include, for example, pH, time, temperature, and buffer composition, which allow binding between the members of interest.

As used herein, when a binding agent is described to bind an analyte, A plurality of the binding agents having the same or similar binding specificity may bind the same analyte. The same analyte may be bound by only one type of binding agent (i.e., so as to be single labeled) or the same analyte may be bound by a second or third binding agent having a different binding specificity (i.e., so as to be double or triple labeled).

Details regarding analyte detection systems can be found in the following U.S. patents and patent applications, all of which are incorporated herein by reference in their entirety for the systems taught therein: U.S. Pat. No. 6,906,770 entitled "Fluid Based Analysis of Multiple Analytes by a Sensor Array"; U.S. Pat. No. 6,680,206 entitled "Sensor Arrays for the Measurement and Identification of Multiple Analytes in Solutions"; U.S. Pat. No. 6,602,702 entitled "Detection System Based on an Analyte Reactive Particle"; U.S. Pat. No. 6,589,779 entitled "General Signaling Protocols for Chemical Receptors in immobilized Matrices"; U.S. patent application Ser. No. 09/616,731 entitled "Method and Apparatus for the Delivery of Samples to a Chemical Sensor Array"; U.S. patent application Ser. No. 09/775,342 entitled "Magnetic-Based Placement and Retention of Sensor Elements in a Sensor Array" (Published as U.S. Publication No.: 2002-0160363-A1); U.S. patent application Ser. No. 09/775,340 entitled "Method and System for Collecting and Transmitting Chemical Information" (Published as U.S. Publication No.: 2002-0064422-A1); U.S. patent application Ser. No. 09/775,344 entitled "System and Method for the Analysis of Bodily Fluids" (Published as U.S. Publication No.: 2004-0053322); U.S. Pat. No. 6,649,403 entitled "Method of Preparing a Sensor Array"; U.S. patent application Ser. No. 09/775,048 entitled "System for Transferring Fluid Samples Through A Sensor Array" (Published as U.S. Publication No.: 2002-0045272-A1); U.S. patent application Ser. No. 09/775,343 entitled "Portable Sensor Array System" (Published as U.S. Publication No.: 2003-0186228-A1); U.S. patent application Ser. No. 10/072,800 entitled "Method and Apparatus for the Confinement of Materials in a Micromachined Chemical Sensor Array" (Published as U.S. Publication No.: 2002-0197622-A1); and U.S. patent application Ser. No. 10/427,744 entitled "Method and System for the Detection of Cardiac Risk Factors" (Published as U.S. Publication No.: 2004-0029259.

Further details regarding microsieve- or membrane-based detection systems can be found in the following U.S. Provisional Applications and PCT Applications, all of which are hereby incorporated herein by reference in their entirety for the systems taught therein: U.S. Provisional Application No. 60/736,082, entitled "Analyte Detection Systems and Methods Including Self-Contained Cartridges with Detection Systems and Fluid Delivery Systems," filed on Nov. 10, 2005; PCT Application No. PCT/US05/06074 (WO 05/085796) entitled "Integration of Fluids and Reagents into Self-Contained Cartridges Containing Sensor Elements," filed Feb. 28, 2005; PCT Application No. PCT/US05/06350 (WO 05/085855) entitled "Integration of Fluids and Reagents into Self-Contained Cartridges Containing Sensor Elements and Reagent Delivery Systems," filed Feb. 28, 2005; PCT Application No. PCT/US05/06349 (WO 05/083423) entitled "Integration of Fluids and Reagents into Self-Contained Cartridges Containing Particle Based Sensor Elements and Membrane-Based Sensor Elements," filed Feb. 28, 2005; PCT Application No. PCT/US05/06077 (WO 05/085854) entitled "Particle on Membrane Assay System," filed Feb. 28, 2005; and PCT Application No. PCT/US05/06593 (WO 05/090983) entitled "Membrane Assay System Including Preloaded Particles," filed Feb. 28, 2005.

The analysis may indicate that an analyte of interest is present in the sample. In an embodiment, user-defined threshold criteria may be established to indicate a probability that one or more specific cells are present on the microsieve. The criteria may be based on one or more of a variety of characteristics of the image. In some embodiments, the criteria may be based on pixel or color fingerprints established in advance for specific cells. The characteristics that may be used include, but are not limited to, the size, shape, or color of portions of matter on the image, the aggregate area represented by the matter, or the total fluorescent intensity of the matter. In an embodiment, the system may implement an automated counting procedure developed for one or more cells.

In an embodiment, the system may include a computer system. A computer system may include one or more software applications executable to process a digital map of the image generated using a detector. For example, a software application available on the computer system may be used to compare the test image to a pre-defined optical fingerprint. Alternatively, a software application available on computer system may be used to determine if a count exceeds a pre-defined threshold limit.

A detector may be used to acquire an image of the analytes and other particulate matter captured on a microsieve. Cells may collect on a microsieve along with dust and other particulate matter and be captured in an image produced from a detector. The image acquired by the detector may be analyzed based on pre-established criteria. A positive result may indicate the presence of a cell. The test criteria may be based on a variety of characteristics of the image, including, but not limited to, the size, shape, aspect ratio, or color of a portion or portions of the image. Applying test criteria may allow cells to be distinguished from dust and other particulate matter. During analysis, the flow of sample through from a fluid delivery system may be continued.

During analyte testing a sample may be introduced into an analyte detection device (e.g., a cartridge or lab-on-a-chip). A trigger parameter may be measured to determine when to introduce the binding agent/detectable label complex into the analyte detection device. Measurement of the trigger parameter may be continuous or may be initiated by a user. Alternatively, the detectable label may be introduced into the analyte detection device immediately after the sample is introduced.

In some embodiments, the trigger parameter may be the time elapsed since initiation of introducing the fluid into an analyte detection device at a controlled flow rate. For example, a binding agent/detectable label complex may be introduced 20 seconds after initiation of introducing the fluid sample into an analyte detection device at a flow rate of 1 milliliter per minute. In another embodiment, the trigger parameter may be the pressure drop across the microsieve. The pressure drop across the microsieve may be determined using a pressure transducer located on either side of the microsieve.

In some embodiments, the trigger parameter may be the autofluorescence of the analyte captured by the microsieve. A detector may be switched on until a pre-defined level of signal from the autofluorescence of the analyte has been reached. In still another embodiment, filtering software may be used to create a data map of the autofluorescence of the matter on the microsieve that excludes any pixels that contain color in a chosen spectral range. For example, the data map may be used to compute a value for particles that are autofluorescent only in the "pure green" portion of the visible spectrum.

Collecting a sample includes taking a sample of blood from a subject using methods such as withdrawing blood from a needle inserted into the subject's blood vessel, withdrawing blood from a port inserted in a blood vessel of the subject, or puncturing the subject's skin with a sharp needle, lancet, finger-stick or heel-stick and collecting the subject's blood.

In some embodiments, pixel analysis methods may be used in the analysis of an image of a fluid or captured matter. For example, pixel analysis may be used to discriminate microbes from dust and other particulate matter captured on a microsieve. Pixel analysis may include analyzing characteristics of an image to determine whether a cell is present in the imaged fluid.

Pixel analysis may be based on characteristics including, but not limited to, the size, shape, color, and intensity ratios of an image or portions of an image. As an example, the total area that emits light in an image may be used to conduct analysis. As another example, the green fluorescent intensity of an image may be used to conduct analysis. In an embodiment, an "optical fingerprint" for a type of cell may be established for use in pixel analysis. In some embodiments, pixel analysis may be based on ratios between values, such as an aspect ratio of an element of matter captured on an image. In other embodiments, pixel analysis may be based on threshold values.

During use, a detectable label may cause emission of different wavelengths of light depending on the nature of the label. When the detectable label is analyzed with a camera, a user may be able to determine if a particular analyte is present based on the color or presence of emission at a given wavelength. For example, a green label may indicate the presence of an analyte of interest. Any other colored labels may not be of interest to a user. While a person may be able to discern between colors, it is desirable for a computer system to also be able to discern different colors from a sample. Many detectors can only discern specific colors when analyzing an image. For example, many CCD detectors can only discern red, blue and green colors. Thus, a CCD detector may not be able to discern the difference between a particle that emits both blue and green light and a particle that just emits green light, although the color difference may be apparent to a person using the system. To overcome this problem a method of subtracting out particles having the "wrong" color may be used.

Detectable labels may be detected by the presence or absence of label at a certain wavelength. Thus, either a black and white or a color CCD detector is useful in the systems and methods taught herein. Whenever colors are referred to herein, the presence or absence of the label at the appropriate wavelength rather than the color reported may be assessed and/or visualized. Thus, for example, a "yellow," "green," "blue" or "red" cell or label referred to herein may appear white using a black and white CCD detector.

In some embodiments, pixels of an image that do not fall within a color range specified by a user may be discarded from the image. In one embodiment, a fluid may be stained to cause a microbe of interest to emit light in only the green portion of the visible spectrum. By contrast, dust and other debris contained in the fluid may emit light in combinations of green, blue, and red portions of the visible spectrum in the presence of the stain. To isolate the portion of the image that represents only the microbe of interest, binary masks may be created to eliminate light emissions caused by non-microbial matter from the image.

Such a method is depicted in FIGS. 1A-F. FIG. 1A shows an image of all particles captured by a microsieve. For purposes of this example, particles 500, having the no fill pattern, exhibit a green color; particles having a fill pattern identical to the fill pattern of particle 510 have a red color; particles having the a fill pattern identical to the fill pattern of particle 520 have both green and blue light absorption; particles having a fill pattern identical to the fill pattern of particle 530 have both red and blue light absorption; and particles having a fill pattern identical to the fill pattern of particle 540 have a blue color. It should be understood that these color assignments are for illustrative purposes only. In the current example, the goal of the analysis is to find all of the green particles.

Figure 1B:
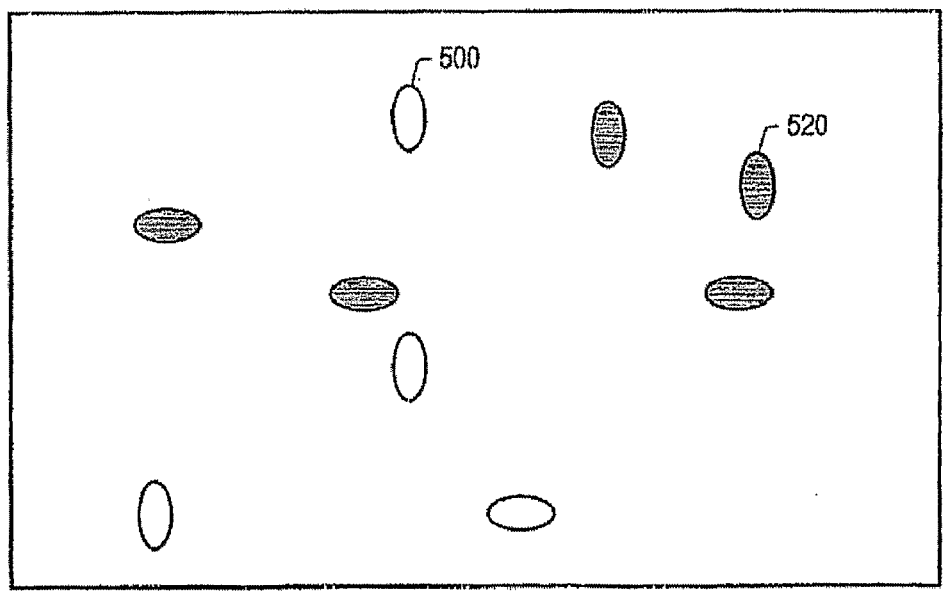
Figure 1C:
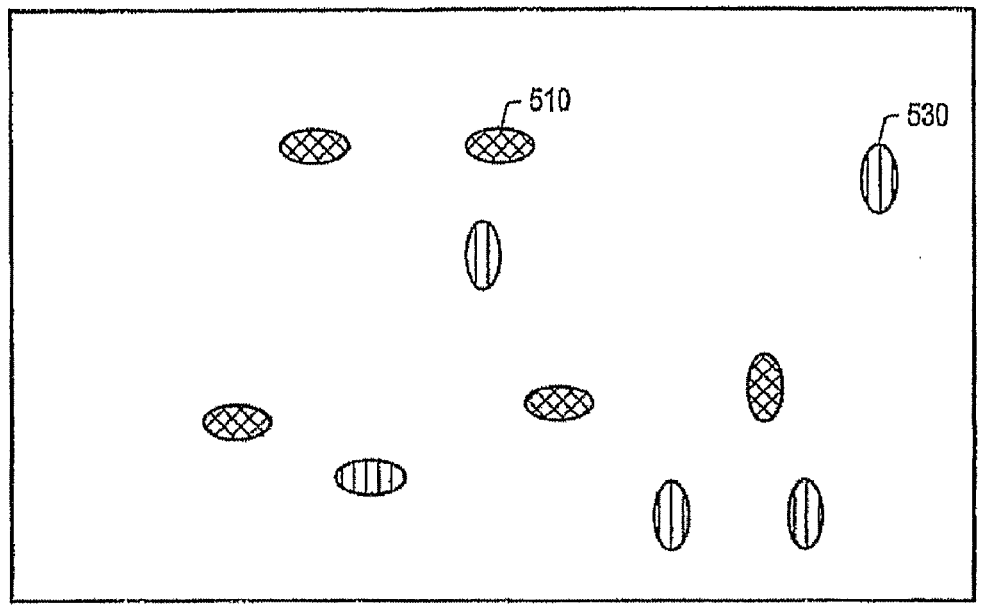

One method of finding the green particles or labeled analytes is to use a filter that will allow only particles that are green to show. FIG. 1B depict the particles that would remain if such a filter is used. All of the particles shown in FIG. 1B have a green light absorption; however, not all of the particles that are depicted in FIG. 1B would exhibit a green color only. Particles 520 absorb both green and blue light. Since the detector can't differentiate between the two types of particles, a false positive may result.

Figure 1D:
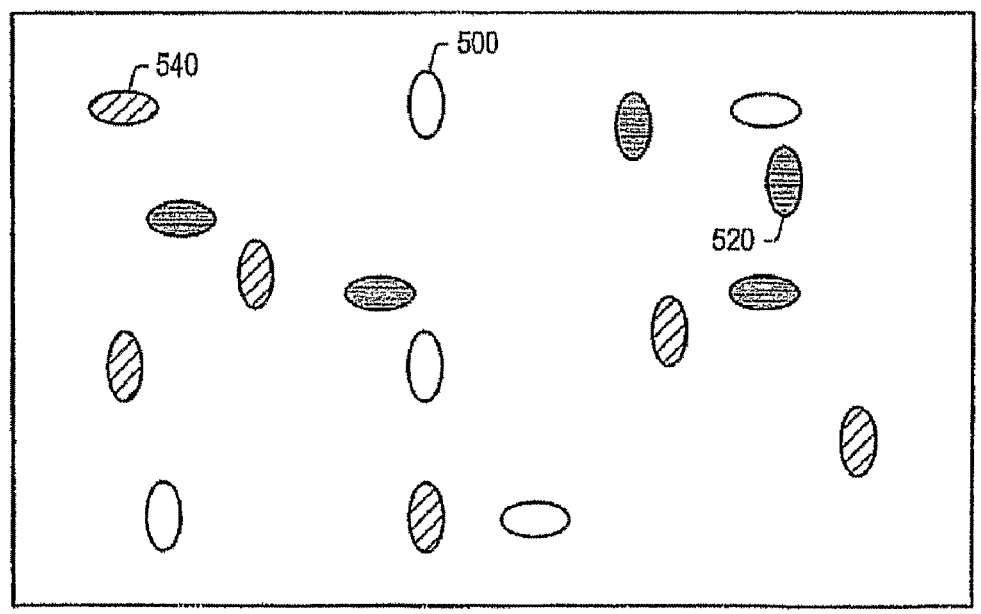

To compensate for this phenomenon, images of particles that absorb blue and red are also analyzed using appropriate filters. By creating masks of which particles exhibit blue and red absorption, a process of elimination may be used to determine how many green particles are present. In an embodiment, an image is then captured of only the particles that exhibit color in the red portion of the spectrum (See FIG. 1C). The image of "red" particles is used to create a mask that may be compared to the full spectrum view of the particles. Since the analytes of interest only exhibit color in the green portion of the spectrum, any particle with color in the red portion of the spectrum may be removed from the original image. FIG. 1D shows the original image but with the particles that appear in the red portion of the spectrum subtracted from the image. The remaining particles are potential particles that may be the analyte of interest.

Figure 1E:
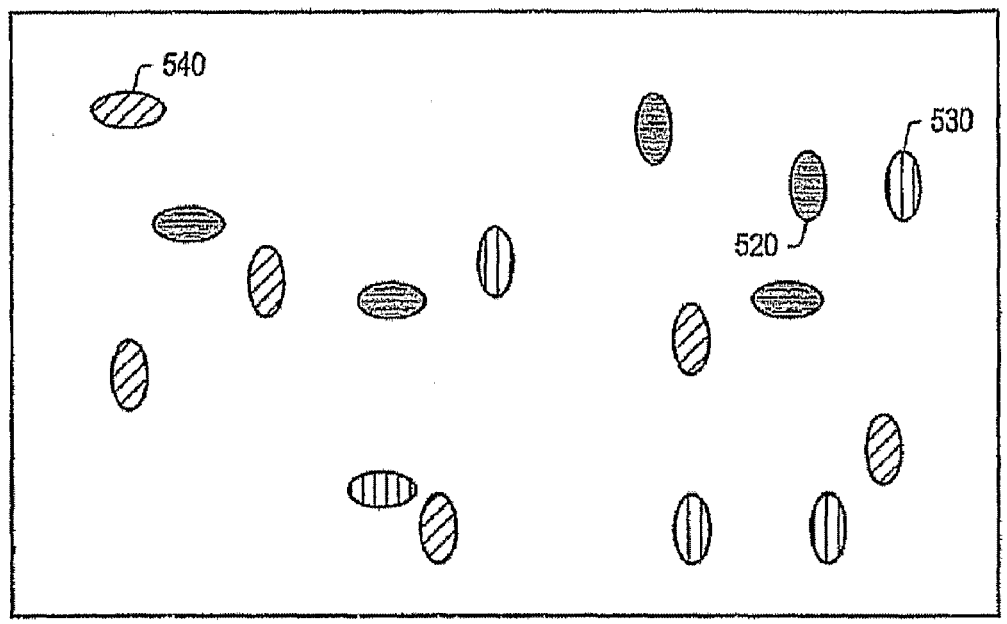
Figure 1F:
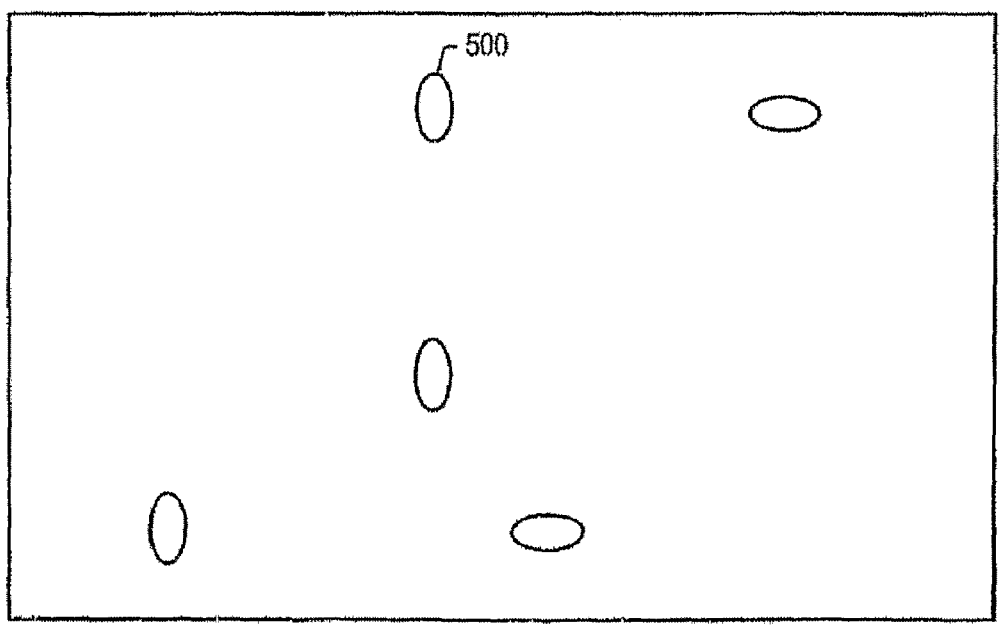

In a second iteration, FIG. 1E shows a binary mask that may be used to mask any pixels that include a blue component. An image is captured of only the particles that exhibit color in the blue portion of the spectrum (See FIG. 1E). The image of "blue" particles is used to create a mask that may be compared to the full spectrum view of the particles. Since the analytes of interest only exhibit color in the green portion of the spectrum, any particle with color in the blue portion of the spectrum may be removed from the original image. FIG. 1F shows the original image but with the red binary mask and blue binary mask applied so that pixels including a red or blue component are excluded. The particles that remain in the image are thus particles that only exhibit a green color. Thus, the method may be used to produce an image that includes only "pure green" pixels. Such an image may be analyzed to detect the presence of a microbe by eliminating particles that are not relevant. It should be understood that while the above recited example is directed to determining the presence of green particles it should be understood that the process can be modified to determine blue particles only, red particles only, or particles that exhibit combinations of colors (e.g., red and blue, red and green, blue and green, or red, blue and green).

Figure 2:
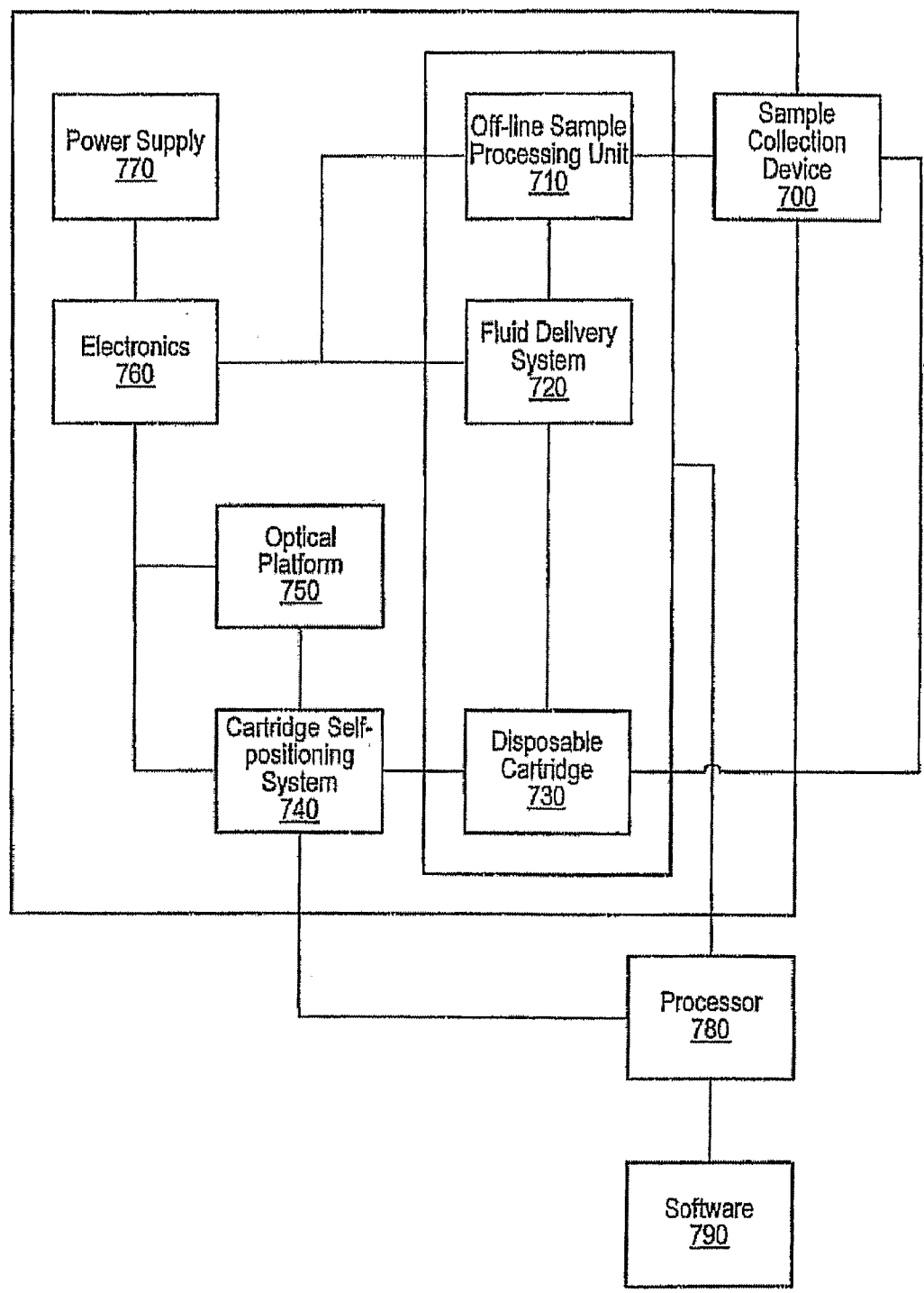
FIG. 2 depicts a schematic diagram of a device for microsieve-based analyte detection.

FIG. 2 depicts an embodiment of a microsieve-based detection system. The microsieve-based detection system may be coupled to, positioned in, or positioned on cartridge 100. The microsieve-based detection system may be integrated in the cartridge.

In some embodiments, a microsieve is selected depending on the analyte of interest. The microsieve may capture or retain matter in the sample (e.g., particles, cells, or other matter). Matter may be retained on a surface of the microsieve and/or in the microsieve. The microsieve may include a thin film or layer capable of separating one or more components from a liquid passing through the film or layer. The surface of a microsieve may be hydrophilic to promote cell proliferation across the surface of the microsieve. A microsieve may have a variety of shapes including, but not limited to, square, rectangular, circular, oval, and/or irregularly shaped. In some embodiments, a microsieve includes openings (e.g., pores) that inhibit an analyte of interest from passing through the microsieve. A microsieve designed to capture substantially all of an analyte of interest may be selected depending on the analyte of interest.

In some embodiments, a microsieve is a monolithic microchip with a plurality of high-density holes. The monolithic microchip microsieve may be formed from materials including, but not limited to, glass, silica/germanium oxide doped silica, inorganic polymers, organic polymers, titanium, silicon, silicon nitride, and/or mixtures thereof. Organic polymers include, but are not limited to, PMMA, polycarbonate (PC) (e.g., NUCLEOPORE® membrane, Whatman, Florham Park, N.J.), and resins (e.g., DELRIN®, Du Pont, Wilmington, Del.). A microsieve formed of polymeric material may include pores of a selected range of dimensions. In certain embodiments, a microsieve is an acrylic frit. In some embodiments, a microsieve is formed of multiple layers (e.g., at least 2 layers, at least 3 layers, at least 4 layers, or at least 5 layers) of etchable and/or non-etchable glass. In some embodiments, a microsieve is formed from an anti-reflective material and/or a material that does not reflect light in the ultraviolet-visible light range. In some embodiments, a microsieve includes one or more locking mechanisms to assist in securing placement of the microsieve in or on the cartridge or microsieve support.

Microsieves may have a thickness from about 0.001 mm to about 25 mm, from about 1 mm to about 20 mm, or from about 5 mm to 10 mm. In some embodiments, a thickness of the microsieve ranges from about 0.001 mm to about 2 mm. Microsieves may have a diameter from about 1 mm to 500 mm, from about 5 mm to about 100 mm, or from about 10 mm to about 50 mm.

Pores of a microsieve may have various dimensions (e.g., diameter and/or volume). In some embodiments, pores of the microsieve may have approximately the same dimensions. In some embodiments, microsieve pores have a pore diameter ranging from about 0.0001 mm to about 1 mm; from about 0.0002 mm to about 0.5 mm; from about 0.002 mm to about 0.1 mm. The microsieve pores have, in some embodiments, a pore diameter of at most 0.005 mm or at most 0.01 mm.

Pores of the microsieve may be randomly arranged or arranged in a pattern (e.g., a hexagonal close-packed arrangement). Pores of the microsieve may occupy at least 10 percent, at least 30 percent, at least 50 percent, or at least 90 percent of the surface area of a microsieve. The pores may assist in selectively retaining matter in a sample and/or a fluid; including, for example, selected cell types like white blood cells.

In some embodiments, a microsieve is positioned from about 0.3 mm to about 0.5 mm below a top surface of the cartridge. In some embodiments, the microsieve includes a support. In some embodiments, a microsieve is designed such that a microsieve support is not needed (e.g., utilizing a microsieve having a thickness of at least 5 mm). In some embodiments, one or more layers separate the microsieve and the microsieve support. The microsieve support may facilitate positioning of the microsieve in or on the cartridge.

In some embodiments, a microsieve is positioned from about 0.3 mm to about 0.5 mm below a top surface of the cartridge. In some embodiments, the microsieve includes a support. In some embodiments, a microsieve is designed such that a microsieve support is not needed (e.g., utilizing a microsieve having a thickness of at least 5 mm). In some embodiments, one or more layers separate the microsieve and the microsieve support. The microsieve support may facilitate positioning of the microsieve in or on the cartridge.

A support assembly may be coupled to the microsieve support to allow the microsieve and microsieve support to withstand backpressures of at least 10 psi. The microsieve support may be selected to produce a predetermined backpressure. When backpressure is controlled, cells may be more uniformly distributed across a surface of a microsieve. Uniform distribution of cells across a microsieve surface may facilitate imaging of a region containing cells and/or analyte detection.

In some embodiments, a microsieve support includes open areas (e.g., pores or holes). Open areas in the microsieve support may have any shape, such as substantially square and/or substantially circular. The shape of the open areas in the microsieve support may be different than the shape of pores in the microsieve. Open areas of the microsieve support may be equal to or greater than the diameter of the pores of the microsieve. In some embodiments, a microsieve support has open areas with diameters ranging from about 0.0001 mm to about 1 mm, from about 0.0002 mm to about 0.5 mm, or from about 0.002 mm to about 0.1 mm. The open areas have, in some embodiments, diameters of at most 0.005 mm or at most 0.01 mm.

In a microsieve-based detection system, a fluid and/or sample in the detection region of the cartridge may be treated with a light. Interaction of the light with the fluid and/or sample may allow the analyte to be detected. Light from one or more light sources may shine on or in at least the detection region of a cartridge, such as the portion of the microsieve where the fluid and/or sample is retained. The light may allow a signal from the retained fluid and/or sample to be detected. When light shines on a microsieve surface, some of the light may be reflected. Areas proximate the detection region may also reflect some of the light that shines on a sample. Light reflecting from the microsieve surface and/or microsieve support may interfere with obtaining an accurate reading from the detector and so it may be advantageous to optically couple an anti-reflective material to the microsieve and/or the microsieve support.

In some embodiments, an anti-reflective material is optically coupled to the microsieve and/or the microsieve support. Alternatively, an anti-reflective material may be a coating on a surface of the microsieve and/or microsieve support. For example a black coating on a surface of the microsieve and/or microsieve support may act as an anti-reflective coating.

In certain embodiments, a portion of the microsieve and/or microsieve support may be made of an anti-reflective material. The anti-reflective material may be positioned above or below a microsieve. An anti-reflective material may inhibit the reflection of light applied to analytes retained in or on the microsieve. The anti-reflective material may absorb one or more wavelengths of light that are emitted by an analyte of interest. The anti-reflective material may improve the contrast of an image of at least a portion of the analyte retained in or on the microsieve by inhibiting reflection of light.

In some embodiments, materials that form the components of the cartridge control flow of fluids through the cartridge. In some embodiments, hydrophilic material is coupled to the microsieve and/or microsieve support. Alternatively, hydrophilic material may be a coating on a surface of a microsieve and/or microsieve support. In certain embodiments, a portion of the microsieve and/or microsieve support is made from hydrophilic material. Hydrophilic material may enhance flow of a fluid through the microsieve. Hydrophilic material may reduce the formation of air bubbles across the microsieve and microsieve support and/or inhibit nonspecific binding of analytes. Hydrophilic material may attract or have an affinity for aqueous fluids flowing through the microsieve. Hydrophilic material may be positioned downstream of the microsieve.

In some embodiments, hydrophobic material is positioned in or on the cartridge. Hydrophobic material may repel aqueous fluid away from surfaces of the cartridge and cause the fluid to flow towards the microsieve. For example, positioning a top member above the microsieve forms a cavity between the top member and the microsieve. Hydrophobic material may be coupled to the top member. The hydrophobic material may be a coating on a surface of the top member, and/or the hydrophobic material may form a portion of the top member. As an aqueous sample or fluid enters the cavity, it is repelled away from the hydrophobic top member and flows towards the microsieve.

In some embodiments, the cellular components of a sample may be characterized by detecting the presence and/or expression levels of one more molecular groups (e.g., polypeptides, polynucleotides, carbohydrates, lipids) typically known to be associated or correlated with a specific trait for which the test is being performed. For example, a blood sample may be collected to measure the number of one or more specific cell types present in the sample (commonly referred to in the art as "cell counts"), and/or the ratio thereof with respect to one or more different cells types also present in the sample. Examples of the types of blood cells that may be detected in a blood sample include, but are not limited to, erythrocytes, lymphocytes (e.g., T cells and B cells), Natural Killer (NK)-cells, monocytes/macrophages, megakaryocytes, platelets, eosinophils, neutrophils, basophils or mast cells. In some embodiments, various sub-populations of specific cell types within a fluid sample are distinguished. For example, the T cells present in a blood sample may be further categorized into helper ($CD4^+$), cytotoxic ($CD8^+$), memory (CD4/CD8 and/or CD45RO) or suppressor/regulatory ($CD4^+$ $CD25^+FOXP3^+$) T cells. Alternatively, B cells present in a blood sample may be further categorized into populations of immature, mature, activated, memory, or plasma cells, based on the immunoglobulin isotype expressed on the cell surface, and presence or absence of various additional proteins.

Table I summarizes the surface expression profile of a selection of non-limiting protein markers that may be used to classify the stage of B cell differentiation, where filled circles denote expression, open circles denote lack of expression, and partially filled circles denote partial or limited expression of the indicated surface marker. The presently described systems and methods are not limited to detecting the cell types disclosed in Table I. It should be understood, that the presently disclosed systems and methods may be suitably adapted to analyze most cell types and/or macromolecules present in a biological sample without departing from the spirit and scope of the presently described embodiments.

TABLE I

| B cell stage | Surface Immunoglobulin isotype | | | Marker protein | | | | |
|---|---|---|---|---|---|---|---|---|
| | IgM | IgG or IgA | IgD | CD23 | PCA-1 | CD38 | CD25 | CD10 |
| Pre B | ○ | ○ | ○ | ○ | ○ | ● | ○ | ◐ |
| Immature | ● | ○ | ○ | ◐ | ○ | ○ | ◐ | ○ |
| Mature | ● | ○ | ● | ● | ○ | ○ | ● | ○ |
| Activated | ● | ● | ○ | ● | ○ | ○ | ● | ● |
| Memory | ○ | ● | ○ | ○ | ○ | ○ | ○ | ○ |
| Plasma cell | ○ | ○ | ○ | ○ | ● | ● | ○ | ○ |

Analysis of a cellular composition of a sample may include detecting the presence of one or more "surface markers" known to be expressed on the surface of the population of cells of interest. Certain surface markers useful in the differential identification of cells in a sample (e.g., in particular cells involved in immune responses) and/or diseases are commonly referred to as "cluster of differentiation (CD)" antigens or CD markers, of which over 250 have been characterized. Many of the CD antigens may also be referred to by one or more alternative art-recognized terms. Table II lists several examples of CD antigens, and the cells in which they are expressed, that may be referred to using one or more alternative terms. The system of CD marker nomenclature is widely recognized by ordinary practitioners of the art. General guidance in the system of CD marker nomenclature, and the CD expression profiles of various cells may be found in most general immunology reference textbooks such as, for example, in IMMUNOLOGY, $4^{th}$ Edition Ed. Roitt, Brostoff and Male chapter 28 and Appendix II (Mosby/Times Mirror International Publication 1998), or in IMMUNOBIOLOGY: THE IMMUNE SYSTEM ▫▫ HEALTH AND DISEASE, $5^{th}$ Edition, Eds. Janeway et al. Appendices I-IV (Garland Publishing, Inc. 2001).

TABLE II

| CD Antigen | Identity/function | Expression |
|---|---|---|
| CD2 | T cell adhesion molecule | T-cells, NK cells |
| CD3 | T cell receptor ($\gamma, \delta, \epsilon, \zeta, \eta$) | Thymocytes, T cells |
| CD4 | MHC class II receptor | Thymocyte subsets, T helper cells, monocytes, macrophages |
| CD8 | MHC class I receptor | Thymocytes subsets, cytotoxic T cells |
| CD10 | Neutral endopeptidase/CAALA | T and B-cell precursors, activated B cells, granulocytes |
| CD11a | Integrin $\alpha$ | Lymphocytes, granulocytes, monocytes and macrophages |
| CD11b | Integrin $\alpha$ | Myeloid and NK cells |
| CD13 | Aminopeptidase N | Monocytes, granulocytes |
| CD16 | Fc$\gamma$RIIIA/B | Neutrophils, NK cells, macrophages |
| CD19 | B cell function/activation | B-cells |
| CD20 | $Ca^{2+}$ ion channel | B-cells |
| CD21 | C3d and EBV receptor | Mature B cells |
| CD35 | Complement receptor 1 | Erythrocytes, B cells, monocytes, neutrophils, eosinophils |
| CD41 | $\alpha$IIb integrin | Platelets, megakaryocytes |
| CD45RO | Fibronectin type II | T-cell subsets, B-cell subsets, monocytes, macrophages |
| CD45RA | Fibronectin type II | B cells, T-cell subsets (naive T cells), monocytes |
| CD45RB | Fibronectin type II | T-cell subsets, B cells, monocytes, macrophages, granulocytes |
| CD56 | NKH-1 | NK cells |

In some embodiments, an analyte detection system may be used for prognostic tests for HIV seropositive patients. HIV infects CD4$^+$ cells (e.g., certain populations of T helper cells, monocytes and macrophages) by binding to a co-receptor CCR5. The expression level of certain CCR5 variants in CD4$^+$ cells has been shown to correlate with viral load and progression to AIDS. In certain embodiments, analyte detection systems and methods may be used to, for example, monitor CCR5 expression in CD4$^+$ cells in patient blood samples. This parameter may advantageously be measured simultaneously from a single sample with one or more measures of HIV viral load. In some embodiments, the tests described herein may further measure one or more blood parameters associated with other pathological situations in addition to, or alternatively to, HIV infection.

In some embodiments, an analyte detection system as described herein may be used to diagnose viral infections in addition to HIV. Blood samples from both Epstein-Barr virus (EBV) and cytomegalovirus (CMV) infected patients exhibit increases in percentages of total T-cells, suppressor T-cells and activated HLA-DR$^+$ T-cells when compared with healthy, uninfected people. Additionally, as seen in HIV infected patients, individuals infected with EBV and/or CMV typically display significantly decreased levels CD4$^+$ T-cells as well as a decrease in the ratio of CD4/CD8 T cells. Blood samples from individuals infected with EBV may also exhibit elevated levels of NK cells.

The analyte detection systems described herein may, in some embodiments, be adapted to readily, reproducibly, and cost effectively diagnose a variety of maladies endemic to geographic and/or economically disadvantaged regions. An example of such an application is point-of-care diagnosis of malaria in geographic areas such as, for example, Africa, Latin America, the Middle East, South and Southeast Asia, and China. Currently, reliable diagnosis of malaria is time consuming, labor intensive, and typically involves identifying erythrocytes harboring *Plasmodium* parasites. Identification of such cells is typically made by microscopic examination of uncoagulated Giemsa-stained blood samples, possibly in combination with one or more serological and/or molecular diagnostic tests (e.g., polymerase chain reaction), all of which require highly specialized equipment. In some embodiments, analyte detection systems described herein may be sued to detect one or more *Plasmodium*-specific antigens that include, but are not limited to, panmalarial antigen (PMA), histidine-rich protein 2 (HRP2) and parasite lactate dehydrogenase (pLDH) in a blood sample. In some embodiments, the analyte detection systems presently described may be used to monitor one or more physiological parameters associated with malaria. For example, a portion of the hemoglobin from *Plasmodium*-parasitized erythrocytes forms lipidized pigment granules generally referred to as "hemozoin." Phagocytosed hemozoin impairs monocyte/macrophage and hence immune function, at least in part, by reducing the surface expression of MCH class II, CD11c and CD54 in phagocytes. Additionally, low peripheral blood monocyte counts may be associated with patients with severe and complicated malaria. Analyte detection systems described herein may be used to detect and monitor the presence and/or quantities of these physiological parameters associated with malaria.

In some embodiments, analyte detection systems described herein may be used to diagnose Good's syndrome, an immunodeficiency disorder secondary to thymoma and characterized by deficiencies of cell-mediated immunity and T-cell lymphopenia.

A low peripheral monocyte count in individuals with high cholesterol is generally predictive of increase risk for developing atherosclerosis. The presently described analyte detection systems may be readily and advantageously adapted to measure monocyte counts (CD13$^+$CD14$^+$CD45RA) associated with cardiac risk factors. Monocyte counts are also an important physiological parameter in subjects with hypercholesterolemia. Analyte detection systems described herein may also be used to measure the amounts of other cardiac risk factors such as troponin I and/or TNF-$\alpha$.

A percentage of CD8$^+$ cells and a number of monocytes in blood have been associated with progressive encephalopathy (PE). PE is one of the most common complications of HIV infection in children. As antiretroviral drugs become more available, the number of children with PE has increased, thus it is desired to evaluate risk factors for PE. CD8 stained cells may be identified using an analyte detection system to monitor the progress of PE.

An analyte detection system for use in diagnostic and prognostic applications to specific pathologies, such as for example, those described above, may further allow a user of the system to readily identify characteristics in a sample that are associated with the malady. The analyte detection system may include, for example, various receptor molecules (such as specific antibodies) that bind to cell surface markers (e.g., CD markers or other disease-associated molecules) or any other analyte suspected to be present in a sample that allows rapid characterization of the sample. In some embodiments, one or more antibodies (e.g., monoclonal and/or polyclonal antibodies) that specifically recognize and bind to macromolecules expressed on the surface of cells (e.g., CD or other cell surface markers) may be used in an analyte detection system.

While certain specific examples of monoclonal or polyclonal antibodies are set forth above, it will be readily understood by ordinary practitioners of the art that the presently described analyte detection systems may be used, without limitation, in conjunction with any type of antibody that recognizes any antigen, including, but not limited to, commercially available antibodies or antibodies generated specifically for the purpose of performing the tests described herein. Monoclonal and polyclonal antibody design, production and characterization are well-developed arts, and the methods used therein are widely known to ordinary practitioners of the art (see, e.g., "Antibodies: A Laboratory Manual," E. Howell and D. Lane, Cold Spring Harbor Laboratory, 1988). For example, a polyclonal antibody is prepared by immunizing an animal with an immunologically active composition including at least a portion of the macromolecule to which the desired antibody will be raised and collecting antiserum from that immunized animal. A wide range of animal species may be used for the production of antiserum. Examples of animals used for production of polyclonal anti-sera are rabbits, mice, rats, hamsters, horses, chickens, or guinea pigs.

A monoclonal antibody specific for a particular macromolecule can be readily prepared through use of well-known techniques such as those exemplified in U.S. Pat. No. 4,196,265, to Koprowski et al., which is herein incorporated by reference. Typically, the technique involves first immunizing a suitable animal with a selected antigen (e.g., at least a portion of the macromolecule against which the desired antibody is to be raised) in a manner sufficient to provide an immune response. Rodents such as mice and rats are preferred species for the generation of monoclonal antibodies. An appropriate time after the animal is immunized, spleen cells from the animal are harvested and fused, in culture, with an immortalized myeloma cell line.

The fused spleen/myeloma cells (referred to as "hybridomas") are cultured in a selective culture medium that preferentially allows the survival of fused splenocytes. After the fused cells are separated from the mixture of non-fused parental cells, populations of B cell hybridomas are cultured by serial dilution into single-clones in microtiter plates, followed by testing the individual clonal supernatants for reactivity with the immunogen. The selected clones may then be propagated indefinitely to provide the monoclonal antibody of interest. In some embodiments, a microsieve-based detection system for use in performing WBC counts on a blood sample may use one or more polyclonal or monoclonal antibodies that specifically recognize various cell types that constitute WBCs to visualize specific blood cells. Antibodies suitable for this purpose include, but are not limited to: anti-CD3; anti-CD4; anti-CD8; anti-CD16; anti-CD56; and/or anti-CD19 antibodies to specifically recognize: T cells; T helper cells and monocytes/macrophages; cytotoxic T cells; neutrophils, NK cells and macrophages; NK cells; and B cells, respectively.

Also useful as a binding agent in the system taught herein are chimeric antibodies and hybrid antibodies, with dual or multiple antigen or epitope specificities, and fragments, such as F(ab')2, Fab', Fab, Fv and the like, including hybrid fragments. Such binding agents retain their ability to bind their specific antigens. For example, fragments of antibodies which maintain CD4-binding activity are included within the meaning of the term "CD4 antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also useful herein are conjugates of antibody fragments and antigen binding proteins (single chain antibodies) as described, for example, in U.S. Pat. No. 4,704,692, the contents of which are hereby incorporated by reference. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. These Fvs lack the constant regions (Fc) present in the heavy and light chains of the native antibody.

In some embodiments, a microsieve-based detection system is used to assess both CD4 lymphocyte count and CD4 lymphocytes as a percentage of total lymphocytes from a blood sample for diagnosis, staging, and/or monitoring of infections and/or diseases. In some embodiments, these counts may be used for monitoring the progression of HIV disease and associated disorders, for monitoring the effectiveness of HIV therapy, and for determining when HIV patients require therapy. For example, when blood samples having CD4 counts below 200 cells per microliter, the need for specific drug therapy intervention may be indicated. In certain embodiments, comparing CD4 cell counts to CD8, CD3, and/or CD19 cell counts may be used to assess the ratio CD4+ T helper cells with respect to cytotoxic T cells, total circulating T cells, B cells, or combinations thereof.

In some embodiments, CD4 percentage of lymphocyte cell counts from a blood sample are assessed using the microsieve-based detections system by comparing CD4 cell counts to the total lymphocyte population. In other embodiments, the comparison is done by comparing CD4 cell counts to the number of cells identified by, for example, CD2 and CD19. The percentage of CD4 can be determined by comparing CD4 with these other cell surface markers. The CD4 percentage can be used to determine when to start therapy for pediatric patients from infancy up to about 6 years of age. Some pediatricians suggest that if CD4 percentage count were routinely provided, then physicians treating adult patients might begin to routinely use the CD4 percentage in preference to absolute CD4 counts.

In some embodiments, the absolute CD4 cell count can be determined by counting all of the lymphocytes with the CD4 surface marker labeled. Then, the total CD4 cell count for a known volume of the sample applied to the microsieve is used to determine the absolute CD4 cell count. The absolute CD4 cell count can be used to determine when to start adult antiretroviral (ARV) therapy, for example when the CD4 cell count drops below 200 cells per microliter or millimeter cubed.

In some embodiments, detection of cell surface marker is accomplished by chemically conjugating fluorescent dyes, such as ALEXAFLUOR® dyes (available also in fluorescent microparticles) from Invitrogen-Molecular Probes, Inc. (Eugene, Oreg.), to binding partners, such as antibodies and monoclonal antibodies, which bind specific surface markers. Each antibody specifically recognizes and binds to a population of cells exhibiting a specific surface marker without cross reacting with other surface markers, allowing each group of cells exhibiting a specific marker to be selectively labeled. In other embodiments, the fluorescent dye can be indirectly bound to the binding partners by use of a secondary or tertiary antibody containing the fluorescent dye. In some embodiments the same dye can be used to label multiple cell surface markers to make it easier to determine the percentage of CD4 to other markers, for example ALEXAFLUOR®488 can be used with CD2 and CD19 and ALEXAFLUOR®647 can be used with CD4 (or vice versa). In other embodiments, substantially all of the CD cell markers can be labeled with the same label to determine the total lymphocyte count.

In some embodiments, a sample, such as blood or diluted blood, is applied and/or transported to a microsieve of a microsieve-based detection system. The microsieve may retain portions of the sample, while allowing other portions of the sample to pass through. For example, the microsieve may be adapted to retain lymphocytes, while allowing other portions of the sample, such as water or red blood cells, to pass through.

A combination of detectable labels may be applied and/or transported to the microsieve to allow a total number and/or different types of lymphocytes (e.g., T cells, NK-cells, and/or B-cells) to be identified. One or more detectable labels may be added to the matter collected on a surface of the microsieve. For example, detectable labels may allow the detection of anti-CD3, anti-CD4, anti-CD8, anti-CD16, anti-CD56 and anti-CD19 antibodies bound to their respective CD markers on the surface of target cells. In some embodiments, anti-CD2, anti-CD4, and anti-CD19 antibodies may be coupled to the detectable label directly. In some embodiments, the detectable label may be coupled to a second macromolecule that specifically binds to and recognizes the antibody bound to the CD marker.

In some embodiments, a first detectable label may be coupled to CD4+ cells present in a mixed population of cells. Additional, distinct detectable labels may be coupled to the NK-cells, B-cells, and/or other T-cells in the mixed population. For example, a mixed population of cells in a sample may couple to anti-CD4, anti-CD3, anti-CD56, and anti-CD19 antibodies with detectable labels to allow detection of CD4+ T helper cells, total T-cells, NK-cells, and B-cells respectively.

In some embodiments, fluorescent dyes (e.g., ALEXAFLUOR® dyes) may be coupled to antibodies to form fluorophore-labeled antibodies. Use of fluorophore-labeled antibodies to visualize cells may facilitate assessment of the sample. One or more fluorescent dyes may be used to label one or more cell surface markers to facilitate assessment of a desired marker percentage relative to other markers (e.g., a percentage of $CD4^+$ lymphocytes relative to other lymphocytes). In certain embodiments, antibodies may be coupled to fluorescent microparticles to form binding agent/detectable label complexes. Fluorescent microparticles may advantageously provide more fluorescent signal per antibody than fluorophore-labeled antibodies. An image of the cells stained by the first detectable label may be provided and one or more additional images of cells stained by the additional detectable labels may be provided. The images may be compared and/or combined to determine the total number of lymphocytes and/or a number of a specific type of lymphocyte in or on the microsieve. A detector optically coupled to at least a portion of the microsieve may provide the images. An analyzer may automatically compare the images during use. For example, ALEXAFLUOR® 488, which fluoresces green when exposed to light having a wavelength of 488 nm, may be used to visualize anti-CD3 antibodies bound to the surface of all T cells present in a sample. ALEXAFLUOR® 647, which fluoresces red when exposed to light having a wavelength of 647 nm, may be used to visualize anti-CD4 bound to the surface of T helper cells and monocytes. In this way, at least three populations of cells (all T cells stain red, T helper cells stain red and green, the overlap of which shows as yellow, and monocytes which stain green) may be readily and simultaneously identified in a single sample.

Figure 3:
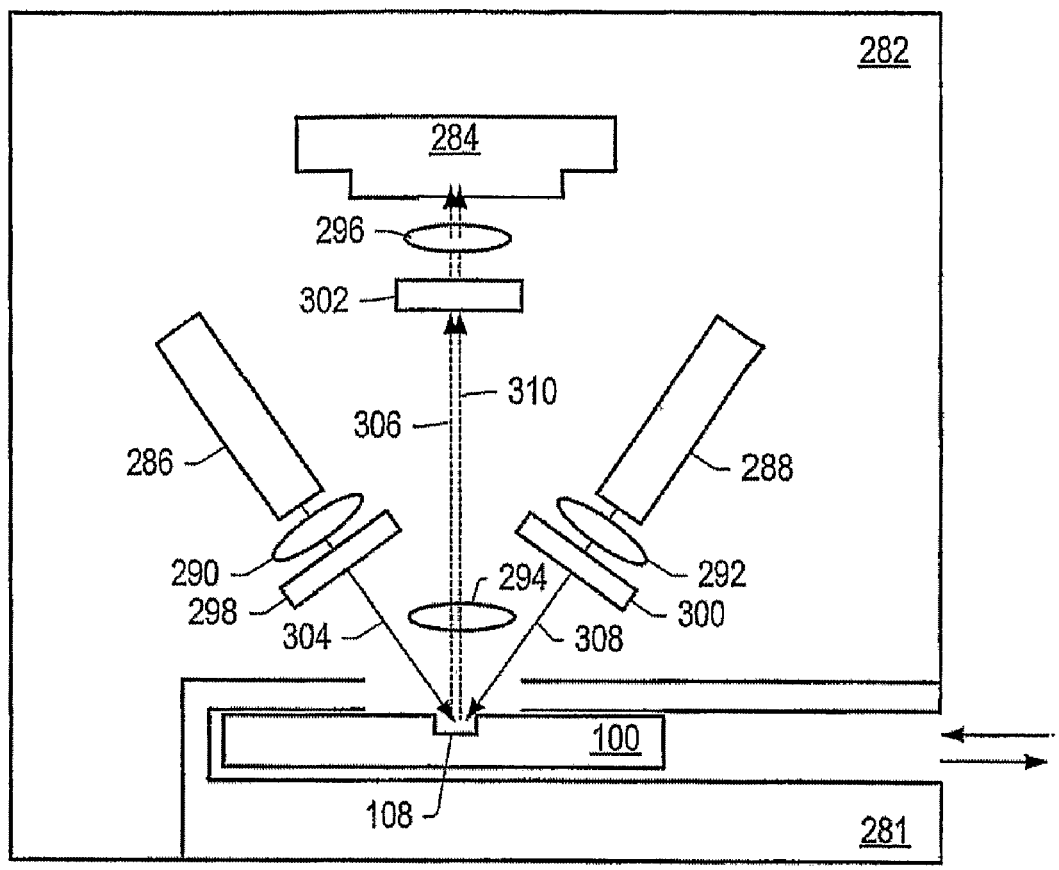
FIG. 3 depicts a schematic diagram of a cartridge positioned in an optical platform with two light sources.
Figure 4A:
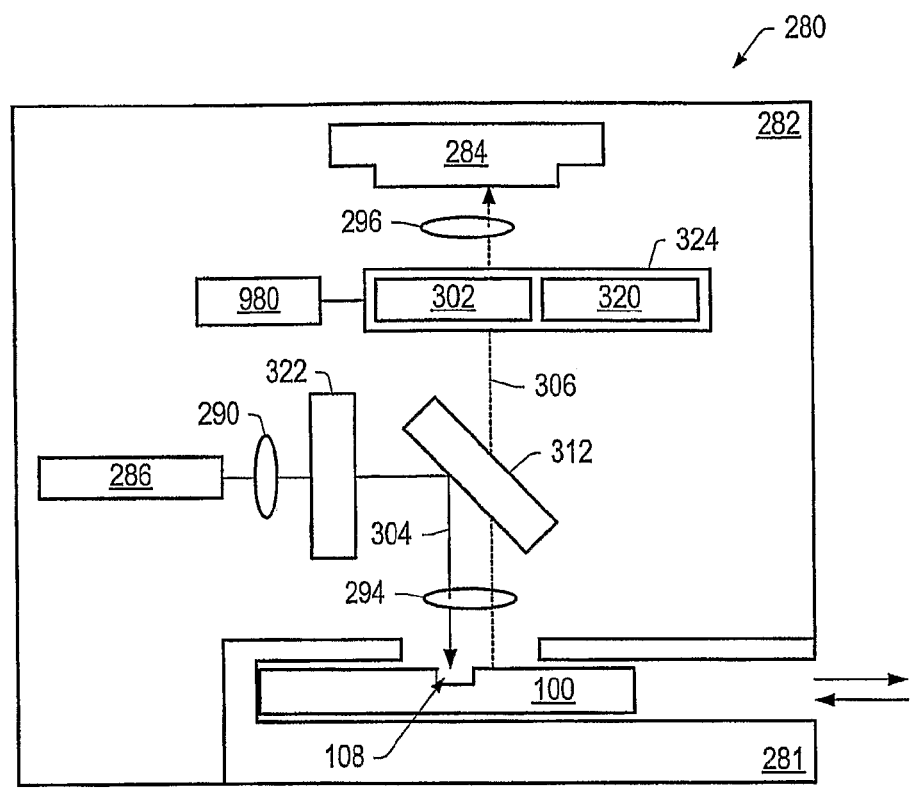
FIG. 4A depicts a schematic diagram of a cartridge positioned in an optical platform that includes movable filters.
Figure 4B:
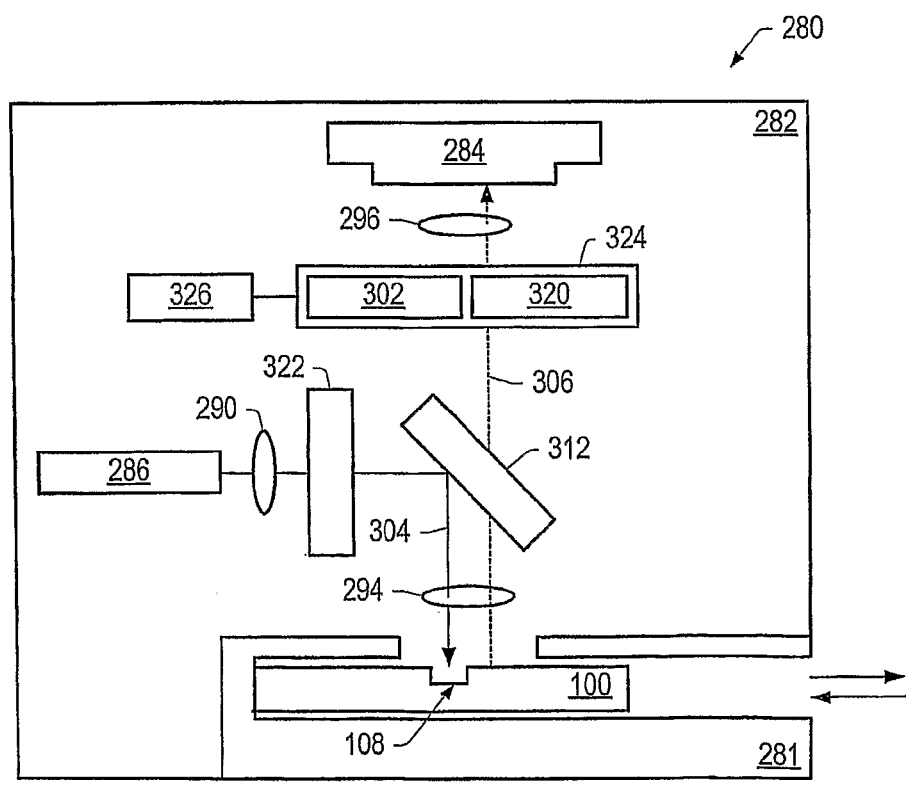
FIG. 4B depicts a schematic diagram of another embodiment of a cartridge positioned in an optical platform that includes movable filters.
Figure 5A:
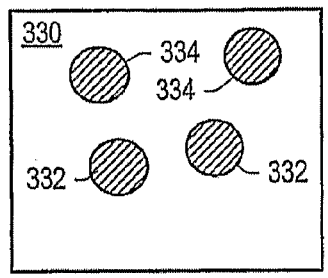
FIGS. 5A-C depict representations of images of cells obtained using an analyte-detection system.
Figure 5B:
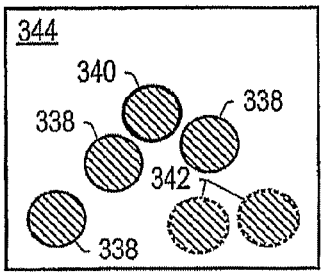
Figure 5C:
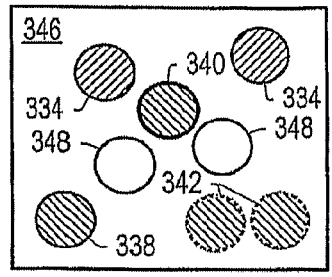

In some embodiments, two fluorophores and two light sources are used to assess lymphocyte populations. The analyte detection system depicted in FIGS. 3, 39 may be used, for example, to determine types of lymphocytes. FIGS. 5A-C depict representations of images collected using two fluorophores and two light sources. For example, a green fluorophore (e.g., ALEXAFLUOR® 488) may be coupled to anti-CD4 antibodies of a sample. A red fluorophore (e.g., ALEXAFLUOR® 647) may be coupled to the anti-CD2 antibodies, anti-CD3 antibodies, and anti-CD19 antibodies added to the sample. As discussed above and shown in Tables I and II, CD4 is expressed on the surface of T helper cells and monocytes, CD19 is expressed on the surface of B cells, CD56 is expressed on the surface of NK cells, and CD3 is expressed on T cells. Analysis of the samples captured on a microsieve using two wavelengths of light may allow differentiation of the types of WBCs captured.

In some embodiments, a green fluorophore (e.g., ALEXAFLUOR® 488) may be coupled to anti-CD4 antibodies of a sample. A red fluorophore (e.g., ALEXAFLUOR® 647) may be coupled to the anti-CD2 antibodies and anti-CD19 antibodies. CD2 is expressed on the surface of T-cells and NK cells. CD19 is expressed on the surface of B cells. Analysis of the samples captured on a microsieve using two wavelengths of light may allow differentiation of CD4+ lymphocytes from other lymphocytes.

FIG. 5A depicts a representation of image 330 of cells 332, 334 obtained by exciting the green fluorophore detectable label with a light source, analyzing the signal generated by the excitation, and producing an image of the cells. These cells 332, 334 represent $CD4^+$ cells.

FIG. 5B depicts a representation of an image of cells obtained by exciting the red fluorophore, analyzing the signal produced from excitation, and producing an image of these cells. These cells 338, 340, and 342, visible in image 344, represent cells expressing CD2 and/or CD19.

In digital detector images, double labeled cells may be identified. Thus, monocytes (e.g., cells that only emit green light) may be distinguished from CD4+ lymphocytes. Combining image 330 and image 344 creates image 346 that includes single labeled "green" cells 334, single labeled "red" cells 338,340,342, and double labeled cells 348, as shown in FIG. 5C. Single labeled green cells 334 are representative of $CD4^+CD2^-CD19^-$ monocytes. Double labeled cells 348 are representative of $CD4^+CD2^+$ T helper cells.

A total number of T-helper cells (cells that express CD4 and CD2), a total number of lymphocytes (cells that express CD2 or CD19), a total number of CD4 cells, and a ratio of CD4 lymphocytes to a total number of lymphocytes may all be determined from the combination of images 330, 344, 346. A total number of lymphocytes may be obtained from the combined image, as depicted in image 346, since the cells may be identified and isolated (e.g., cells that only emit green light or only emit red light).

An absolute number of CD4+ T helper cells is the total number of double labeled cells 348. A ratio of CD4+ T helper lymphocytes to the total number of lymphocytes may be calculated by dividing the total number of double labeled cells 348 (CD4+CD2+) by the total number of red cells 338, 340, 342 (CD2+, CD19+).

The ratio of T-helper cells to total lymphocytes may be important in determining the progression of diseases, such as HIV, and in the treatment and monitoring of other diseases. Although green and red fluorophores were described, fluorophores of any color may be used without limitation. In some embodiments, a monochrome detector may not allow colors of fluorophores to be distinguished.

In some embodiments, use of one or more detectable labels allows identification of lymphocytes retained on a microsieve of a microsieve-based detection system. In some embodiments, the lymphocytes may contain cell surface markers CD4, CD3, and CD19. Identification of CD4 and CD3 and on the surface of cells identifies T-helper cells. FIGS. 6A through 6D represent images of cells expressing CD4, CD3, and CD19 markers in the presence of two excitation sources.

Figure 6A:
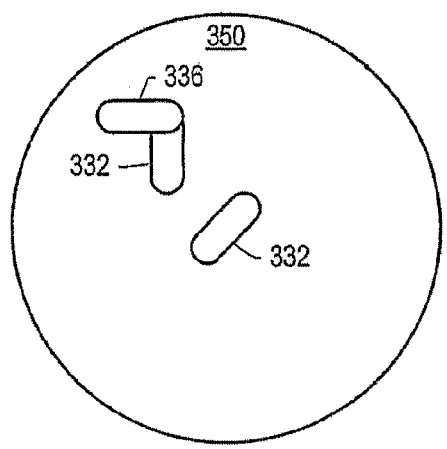
FIGS. 6A-D depict representations of images of cells obtained using an analyte-detection system.

FIG. 6A depicts an image of cells obtained by excitation of a green fluorophore bound to cells expressing CD4. An excitation source may excite green fluorophores and a detector may analyze the signal produced during excitation and produce image 350 of green cells 332, 336.

Figure 6B:
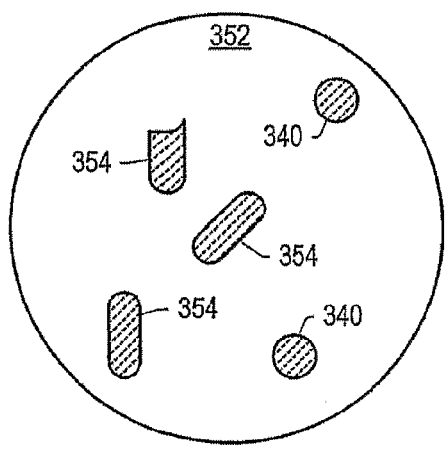

FIG. 6B depicts an image of cells obtained by excitation of a red fluorophore attached to cells expressing CD3 or CD19. An excitation source excites red fluorophores bound to the cells and a detector analyzes the signal produced during excitation and produces image 352 of cells 340 containing CD19 and cells 354 containing CD3.

Figure 6C:
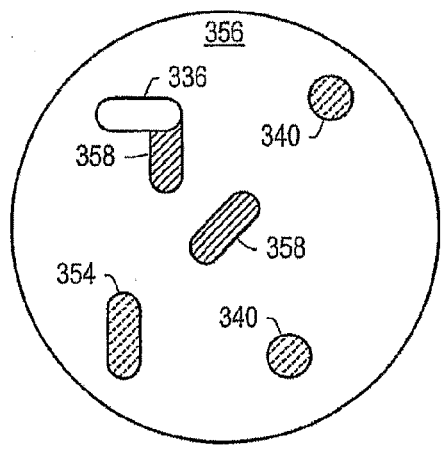

Image 350 may be combined with image 352 to produce image 356 in which green cells 336, red cells 354, 340 and yellow cells 358 are visible. The total number of lymphocytes may be obtained from the image of red cells, as depicted in FIG. 6C. The total number of T helper cells present on the microsieve is identifiable by determining the number of cells that are double labeled (e.g., those cells expressing both CD3 and CD4).

Figure 6D:
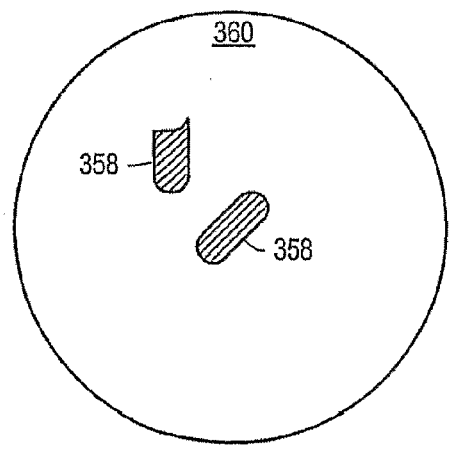

In some embodiments, a filter allows a desired wavelength of light to pass from the detection system to the detector. For example, a filter only allows green light to pass, as depicted in FIG. 6D. Thus, T cells 358 may be identified from image 360 collected by the detector. Using a filter may facilitate identification of one or more types of lymphocytes and/or other types of matter.

While a system to identify T cell populations based on differential staining of CD3, CD4, CD19, and/or CD56 markers on cells is described above, it is understood that any combination of CD markers may be used to identify one or more types of lymphocytes and/or total lymphocytes in a sample.

In some embodiments, all cells except a lymphocyte of interest may be stained. A white light image of the microsieve may be provided. One or more additional images may be provided in which cells stained with one or more detectable labels are visible. The number of a specific lymphocyte population may be obtained by assessing the number of cells appearing in the first image (e.g., the white light image) but not appearing in the additional images (e.g., images in which only stained cells appear). For example, a sample containing lymphocytes may be retained on a microsieve of an analyte detection system. A first image at a selected wavelength of light of the retained cells is taken. One or more detectable labels may be applied to the retained cells. At least one of the detectable labels stains part of the retained cells, but does not stain CD4+ cells. A second image at one or more wavelengths different than the wavelength for the first image is taken. Such "negative selection" strategies may be employed to determine the number of cells that are depicted in the first image but are not depicted in the second image, to give the number of CD4+ lymphocytes. Such strategies may be particularly suited to applications where additional functional analyses are performed on the cell of interest. For example, it is known in the art that contacting certain CD markers (e.g., CD3, CD19) with certain antibodies (commonly referred to as "cross-linking antibodies") causes profound changes in cellular physiology. Therefore, the negative selection strategy outlined above may be useful when additional biological/functional analyses are to be performed on a particular cell type.

In some embodiments, cells expressing CD4 may be stained red and cells expressing CD45 may be stained green. In certain embodiments, cells with certain surface markers may stain brighter than cells without the surface markers. For example, stained CD45 cells may appear brighter than stained CD4+ cells. A percentage of CD4 to total lymphocytes may be determined from the ratio of CD4+ cells to brighter stained CD45 cells.

It may be desirable to stain various cell subtypes differentially to allow discrimination between various cell types even when the cells are stained with antibodies with the same color tag. For example, CD4+ monocyte population may be differentiated from the CD4+ lymphocyte population. Low and high intensity CD4+ cells may be extracted from images of the detection system obtained by a detector. Weakly stained CD4+ cells may then be stained with a CD14 stain that identifies weakly stained CD4+ cells as monocytes.

Similar principles may be applied to other subsets of the lymphocyte population. A difference in the staining of NK-cells, B cells, and T cells due to the number of surface markers, antibody affinity, or antibody performance may identify a CD8 population. CD8 monitoring and/or a ratio of CD4 to CD8 cells may be important in providing information about the progression of certain diseases, such as, for example, HIV progression and AIDS.

It may be desirable to obtain a CD8 percentage and monocyte count from a sample. Monocytes may exhibit a weaker stain with CD4 antibodies, which allows monocytes to be distinguished from CD4 T-cells, which are characterized by a strong stain with CD antibodies.

Differences in surface marker concentrations on cells may provide a tool for discrimination between cells. In some diseases, cell morphology may be correlated with disease states. Images from assay screening may provide information about the assay and cell morphology and may provide additional information about the disease. For example, the malaria antibody may be localized on a part of the cell to allow a difference in intensity across a cell to be observed. This difference in intensity may provide information about the health of the patient.

Different subpopulations of cells may accept the same stain but emit light at different intensities and so the subpopulations may be differentiated. The antibody binding capacity for various surface antigens may be measured using methods generally known to ordinary practitioners of the art. For example, CD4+ T-cells bind about 50,000 antibody molecules. Protocols for assay development and image analysis can be defined based on the relative amount of antibodies molecules that various cells can bind. Often exposure times may be adjusted to further separate populations. For example, a total T-cell population may be identified with an anti-CD3 antibody. Even though CD3 cells are stained with the same color as NK-cells and B-cells, the populations can be determined based on the differential staining characterizing these cells. As the CD3 population becomes separated from the rest of the cell count (e.g., by increasing exposure time when taking the image), the percentage of CD8 cells may be determined by subtracting the number of CD4+ cells and CD3+ cells from the total CD3 cell count. In some embodiments, when cells are stained with anti-CD8 antibody, there exists a strong intensity differential to discriminate CD8 cells from other cells such as NK-cells and B-cells. The strong intensity may accentuate the differential seen in a single color containing $CD8^+$ cytotoxic T cells, NK-cells, and B-cells. A ratio of $CD8^+$ cells may be calculated by dividing the total number of $CD3^+$ cells minus the total number of $CD4^+$ cells and $CD3^+$ cells by the total number of $CD3^+$ cells.

An analyte-detection kit including at least one cartridge designed for performing a pre-determined analysis, a sample collection device and disinfectant wipes may be opened. In some embodiments, the cartridge, wipes, sample collection devices are individually obtained. In certain embodiments, the cartridge is checked for viability prior to use. In some embodiments, a portion of a human may be wiped with one of the disinfectant wipes and a blood sample may be obtained with the sample collection device. A portion of the collected sample may be deposited on or in a collection region of the cartridge. For example, a finger may be pricked with a lancet and a drop of blood transferred to the cartridge using disposable tubing, a pipette, or a fluid bulb. In some embodiments, the sample may be deposited directly onto a microsieve of a microsieve-detection system. After the sample is introduced into a collection region of a cartridge, the collection region may be capped or sealed with, for example, an adhesive strip, a rubber plug, or a cover.

In some embodiments, one or more reagents may be provided to the sample. For example, anti-coagulant and/or fixative may be added to the blood sample. Fixatives include, but are not limited to, paraformaldehyde, ethanol, sodium azide, colchicine, CYTO-CHEX® (Streck, Inc., Omaha, Nebr.), and CYTO-CHEX® BCT. In some embodiments, a reagent may be provided to the sample. The reagent may be mixed with the sample during or after collection of the sample. Alternatively, a reagent may be added to a sample after the sample is introduced into a cartridge. In certain embodiments, a reagent may be provided to the sample by, for example, one or more pumps, fluid packages, and/or reagent regions coupled to, positioned in, and/or positioned on a cartridge.

The cartridge may be positioned, automatically or manually, in a housing of the analyte detection system. The cartridge may substantially contain all fluids used for the analysis.

In some embodiments, a check of the cartridge may be performed. For example, the cartridge includes one or more detectable labels to be determined. An image of the label may be obtained by one of the detectors. Analysis of the image is performed to determine if the known analyte can be detected. If the known analyte is detected, the cartridge is deemed suitable for use. If the known analyte is not detected, the cartridge may be disposed of and a new cartridge obtained. In some embodiments, the new cartridge is obtained from the kit or a supply of cartridges.

At least a portion of the sample may be provided to a metered volume portion of the cartridge. In some embodiments, the sample may be drawn by capillary action into the metered volume portion. In certain embodiments, the sample may be delivered by a fluid delivery system disposed in or coupled to the cartridge. After the sample has filled the metered volume portion, a portion of the sample may travel toward an overflow reservoir. In some embodiments, the sample may not be measured.

A fluid delivery system that includes a reagent may be actuated. Flow of fluid from the fluid delivery system may push a metered volume of sample from the metered volume portion towards a detection region that includes a microsieve-based detection system. The reagent and sample may combine during passage of the sample toward the one or more detection regions to form a sample/reagent mixture. A portion of the sample/reagent mixture flows through or is collected in the detection region. The remaining portion of sample/reagent mixture may flow over or through the detection region to a waste region of the cartridge.

In some embodiments, the fluid delivery system is not necessary to push the sample towards the detection region. Capillary forces may transport the sample towards the detection region. In some embodiments, capillary forces that transport the sample are enhanced with hydrophilic materials (e.g., plastic or glass) to coat a channel for aqueous samples. Certain portion of channels may include hydrophilic materials positioned proximate the collection region, in the metered volume chamber, and/or proximate the overflow reservoir to direct flow of aqueous samples through a cartridge.

In some embodiments, the sample may be drawn into a channel via negative pressure in the channel. For example, suction created by a passive valve or a negative pressure source may create negative pressure in a portion of a channel and draw fluids towards the detection region. In some embodiments, valves may be used to direct the flow of fluid and/or sample through the cartridge.

One or more additional fluid delivery systems may be actuated to release one or more additional fluids (e.g., additional PBS, water, or other buffers). One or more of the additional fluids may flow over or through one or more reagent regions (e.g., a reagent pad or through a channel containing reagents). One or more reagents (e.g., one or more antibodies or a detectable label) in or on the reagent regions may be reconstituted by the additional fluids. The reconstituted reagents may be transported to the detection region of the cartridge. Transport of the reconstituted reagents may be accomplished by continued actuation of the fluid delivery systems or through other methods described herein. The reconstituted reagents may label and wash a portion of the sample collected in one or more detection regions of the cartridge (e.g., wash WBCs retained on a microsieve).

Portions of a sample and/or fluids may be provided to a detection region in a cartridge sequentially, successively, or substantially simultaneously. In some embodiments, a portion of the sample moves towards a detection region as a portion of the fluid from the second fluid delivery system flows towards a reagent region. Fluid from the second fluid delivery system may reconstitute and/or collect one or more reagents from the reagent region and deliver the reagents to the detection region after the sample has passed through the detection region. The collected reagents may then be added to an analytes that have been collected by the detection region.

Valves (e.g., pinch valves, active valves, passive valves) and/or vents may be use to regulate flow of the sample. For example, a valve proximate the collection region may inhibit additional sample from flowing towards the detection region. In some embodiments, one or more changes in elevation of a channel may inhibit the sample form entering other channels.

In some embodiments, a reagent (e.g., a detectable label or one or more antibodies) may be directly added to the matter on a microsieve of a microsieve-based detection system. The sample may then be washed with fluid remaining in the first fluid delivery system or with the fluid from one or more of the fluid delivery systems.

In some embodiments, only one fluid delivery system is used. For example, one or more syringes may be at least partially coupled to, positioned in, or positioned on the cartridge. Each syringe may contain one or more fluids to be used during the analysis. The syringes may be actuated and the fluids delivered sequentially, successively, or substantially simultaneously to the collection region, the reagent regions and/or the detection region.

In some embodiments, analytes collected on a microsieve of a microsieve-detection system may be viewed through a viewing chamber of the microsieve-detection system. Light sources may be activated and light may be directed towards the microsieve-based detection system. Light may enter the microsieve-detection system through a viewing chamber and/or a top layer of the microsieve-detection system. A detector may collect a signal produced from interaction of light with one or more analytes in the detection region. In some embodiments, the detector may be optically aligned with the viewing chamber of the microsieve to allow the microsieve and/or detection region to be viewed by detector.

The detector processes the produced signal to produce images representative of the analytes collected by the detection system. Images may be obtained concurrently or simultaneously. Images may be analyzed and the analytes in the sample assessed.

The cartridge may then be removed from the analyzer and discarded. The above-described method may then be repeated for the next sample. In certain embodiments, portions of the analyzer may be disinfected between samples. In some embodiments, the cartridge is self-contained such that all fluids remain in the cartridge and the analyzer may not need to be disinfected.

Interaction of a sample with light produces a signal that is received by the detector. The detector may produce images from the signal. Images may be analyzed by an analyzer (e.g., automatically with a computer or manually by a human) to determine the analytes present in the sample.

A third fluid delivery system may be activated to allow a wash solution to flow through or over the detection region. The detection region may be washed repeatedly to clear the detection region and prepare for additional use.

The first fluid delivery system may be actuated, or a fourth fluid delivery system may be used, to push a second portion of sample towards the microsieve. The analysis may be repeated to determine different and/or duplicate sample analysis.

The procedure may be repeated as necessary to obtain the needed data. Additional samples may also be obtained and used. In some embodiments, one or more microsieves may be used in a microsieve-based detection system. After all analyses have been completed, the cartridge may be properly discarded.

An optical analysis instrument for microsieve-based measurements may be used to determine the presence of analytes. A schematic diagram of an embodiment of an instrument is depicted in FIG. 2. In one embodiment, an instrument may include a sample collection device 700, an off-line sample processing unit 710, a fluid delivery system 720, a disposable cartridge 730, a cartridge self-positioning system 740, an optical platform 750, electronics 760, power supplies 770, one or more computer processors 780, and/or software 790 and/or firmware.

In some embodiments, the instrument may include one or more disposable cartridges. A disposable sample cartridge may be the chemical and biochemical-sensing component of the analysis instrument. A cartridge may include index-matching, molded or machined plastics, metals, glass or a combination thereof. A cartridge may also include one or more reservoirs for holding reagents, samples, and/or waste. Reservoirs may be coupled to a cartridge via one or more microfluidic channels.

A cartridge may include one or more detection systems. As used herein the term "detection system" refers to a system having an analyte detection platform (e.g., a microsieve-based analyte detection platform). In some embodiments, a cartridge may be designed such that the cartridge is removably positionable in an instrument. Cartridge alignment may be performed manually or automatically using the cartridge positioning system. A cartridge positioning system may automatically or manually position the disposable cartridge in the instrument. In certain embodiments, the disposable cartridge may be placed in the cartridge self-positioning system prior to sample introduction. In one embodiment, a fluid delivery system may deliver reagents to a disposable cartridge. Once the disposable cartridge is placed inside the instrument, the cartridge positioning system may be used to align the one or more areas of the cartridge containing the sample to be analyzed with the instrument's optical platform. The optical platform may acquire images (e.g., visual or fluorescent) of the sample. The images may be processed and analyzed using software, algorithms, and/or neural networks.

An instrument may be used to analyze one or more samples. A sample may include one or more analytes, cells, and/or bacteria. A sample may be collected for analysis with a sample collection device. The sample collection device may be external or internal to the instrument and may be interfaced with the analysis instrument. Depending on the type of measurement to be performed, a sample may be transported through one of two pathways by the sample collection device. In one application, a sample may be transported to an off-line sample-processing unit where the sample may be manipulated. The sample may then be transported to a disposable cartridge via a fluid delivery system. In another embodiment, a sample may be transported directly to a disposable cartridge by a sample collection device. The disposable cartridge, including the sample, may then be inserted into the instrument.

In an embodiment, a sample collection device may include a disposable pipette or capillary tube. A disposable pipette may contain, or may be coated with, one or more appropriate reagents to aid in visualization. For example, a stain may aid in visualization of particles and/or cells in a sample. A disposable pipette may also collect a precise sample volume. It may be desirable to incubate a sample prior to analysis. A sample may be incubated in a disposable tip before being drawn into an instrument. In one embodiment, after incubation, the sample may be delivered to the cartridge manually using the disposable pipette. In another embodiment, a sample cartridge may include one or more appropriate reagents for incubation in the sample or reagent reservoir. In some embodiments, incubation may be performed within the sample cartridge using reagents from a sample or reagent reservoir. After the sample is incubated with one or more reagents, the fluid delivery system may deliver a buffer solution to the sample/reagent reservoir. Delivering a buffer solution to the sample/reagent reservoir may push the labeled sample to a microsieve in the cartridge for subsequent rinsing and sample analysis. After analysis of the sample is completed, the sample may be delivered to a waste reservoir. A waste reservoir may be positioned in the sample cartridge, internal or external to the instrument.

In an embodiment, a portion of a human body, such as a finger, may be positioned proximate a sample reservoir of a cartridge. A portion of a human body may contact a portion of the sample reservoir. A sample reservoir may have a size that allows a predetermined volume of sample to be collected. A cartridge sample reservoir may include a sample pick-up pad. A sample pick-up pad may be a pad that absorbs and/or collects samples deposited on a surface of the sample pick-up pad. A sample pick-up pad may be made of an absorbent material. A sample pick-up pad may draw a sample from a portion of a human body in contact with the sample pick-up pad to a sample reservoir. For example, a sample collection device may make a small incision in a portion of a human body. The portion of the human body may be brought proximate a sample pick-up pad. Blood from the small incision may flow onto the sample pick-up pad. Blood from the sample pick-up pad may then be delivered to the cartridge via a fluid delivery system. In an embodiment, a sample pick-up pad may include one or more anti-coagulants and/or reagents for sample labeling. A sample reservoir may include one or more anti-coagulants and/or reagents for sample labeling.

In certain embodiments, a fluid delivery system may include metered pumps (e.g., syringe, rotary, and/or peristaltic), valves, connectors, and/or pressure-driven actuation (e.g., roller with motorized translation). A fluid delivery system may be vacuum-driven (e.g., a cartridge may be under vacuum). A fluid delivery system may draw one or more samples into an instrument, deliver one or more samples to a sample cartridge, and/or move fluids such as sample, reagents and/or buffers through the cartridge and other channels or fluid lines. A fluid delivery system may deliver samples and/or other fluids to a waste reservoir after analysis. In one embodiment, a fluid delivery system may be used to wash a cartridge after sample analysis. Fluid may be driven through a cartridge after a sample is analyzed by the fluid delivery system. The fluid may then flow from the cartridge to a waste reservoir.

Figure 7A:
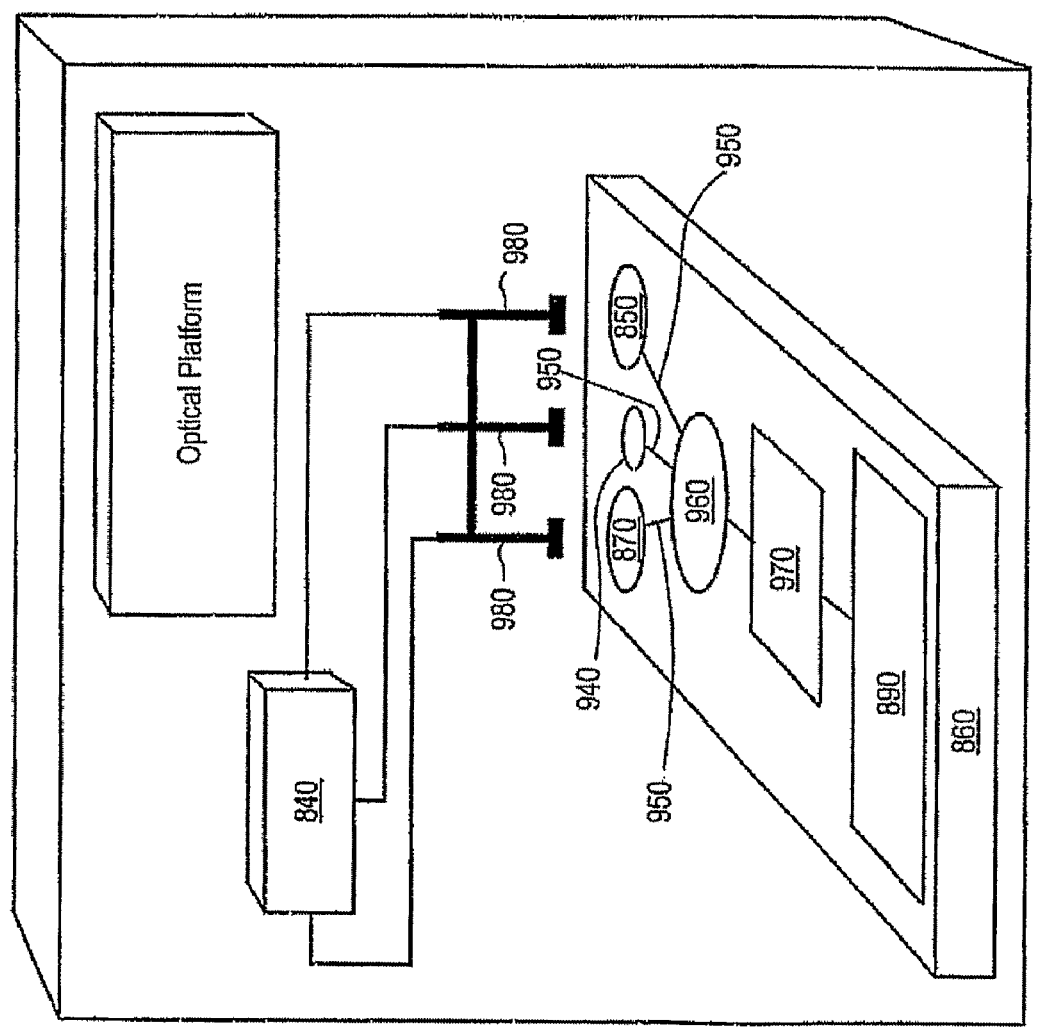
FIG. 7A depicts a schematic diagram of a detection system with actuator.
Figure 7B:
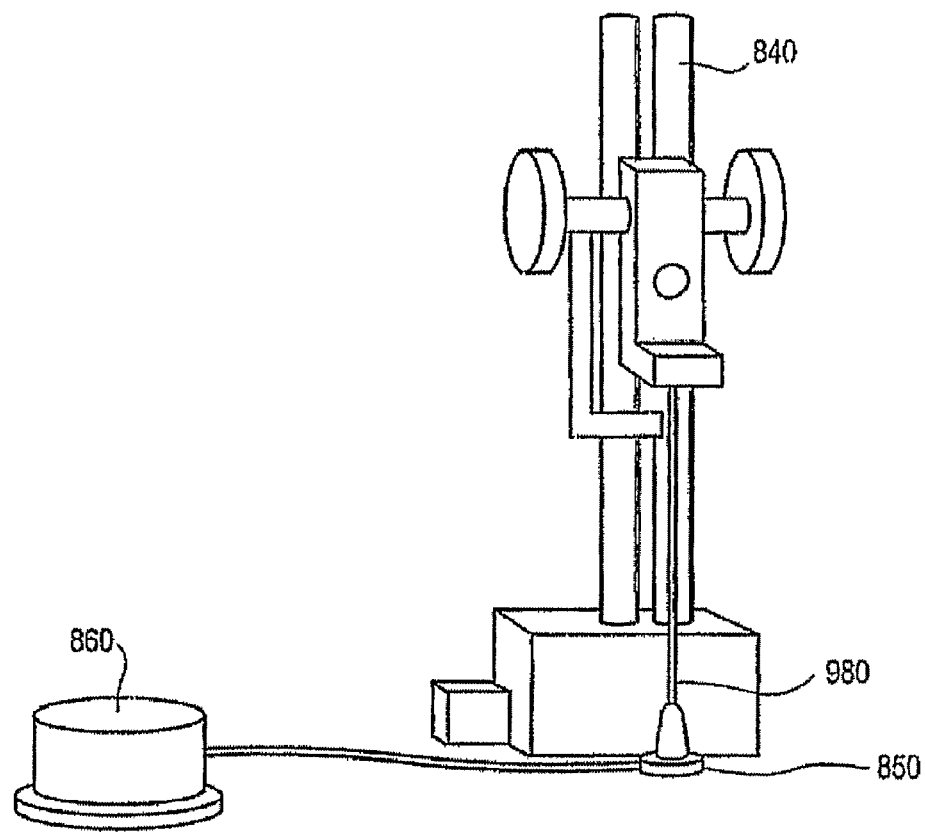
FIG. 7B depicts an embodiment of an actuator.
Figure 7C:
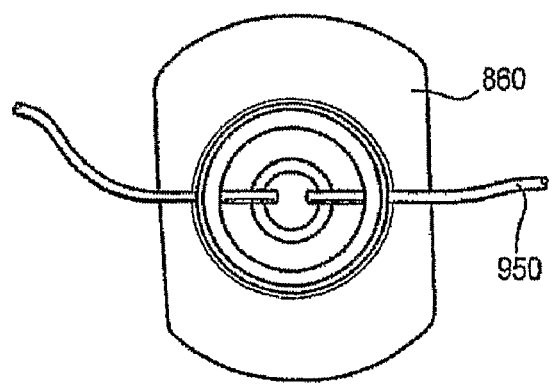
FIG. 7C depicts an embodiment of a channel coupled to a sample cartridge.

FIG. 7A depicts one embodiment of a sample cartridge and its interface with an actuated fluid delivery system. In this example, the buffer 870, reagents 850, and/or sample 940 are contained in reservoirs. Reservoirs may be substantially sealed reservoirs positioned in a cartridge. In an embodiment, applying pressure to a reservoir may release the contents of the reservoir into channels 950. Actuators 840 may press down on the fluid containing reservoirs, delivering the contents to the microsieve 960 or other detection platform 970. FIG. 7B depicts an embodiment of an actuator 840. Actuator 840 may include a mechanism for applying pressure to one or more reagent packs 850, either individually or simultaneously. In one embodiment, actuator 840 includes an elongated member 980 that is moved by the actuator 840 to apply pressure on one or more reagent packs 850, causing the reagent packs to release one or more reagents to a cartridge 860. During use, an actuator 840 may apply pressure to a reagent pack 850, forcing one or more reagents in the reagent pack through a channel 950, as depicted in FIG. 7A. Channels 950 may couple a reagent pack 850 to a microsieve 960 and/or other detection platform 970 in a sample cartridge 860. As pressure on a reagent pack 850 increases, more reagent may be released from the reagent pack and into a channel 950. As depicted in FIG. 7C, reagents may flow through a channel 950 and into a sample cartridge 860. Sample and reagent may flow out the sample cartridge 860 via a channel due to actuation. Increased pressure from actuators on buffer 870, sample 940, and/or reagent packs 850 may drive fluid from the microsieve 960 and/or other detection platforms 970 and into a waste reservoir 890, see FIG. 7A. A waste reservoir 890 may be positioned in the cartridge 860.

Figure 8A:
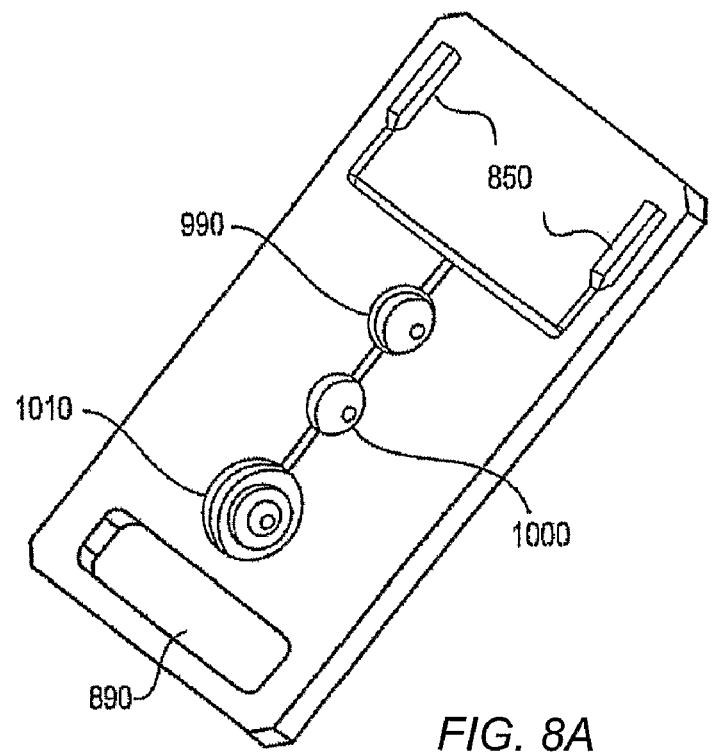
FIGS. 8A-C depict schematic diagrams of disposable sample cartridges.

FIG. 8A depicts an embodiment of a disposable cartridge including reagent packs. During use, a sample (e.g., blood obtained from a fingerstick) may be delivered to a sample reservoir 990. A reagent pack 850 may deliver one or more reagents to a sample reservoir 990 by actuation. In an embodiment, an actuator may apply pressure on a reagent pack 850 and force reagent from a reagent pack through channels 950 and into a sample reservoir 990. Reagents and a sample may react in the sample reservoir 990. In certain embodiments, further actuation may cause the modified sample, or sample reacted with reagents, into a trap 1000. Trap 1000 may be a bubble trap. Trap 1000 may be designed to release air from a fluid passing through it. Trap 1000 may substantially remove air from a sample flowing through a trap. Further actuation may then push a substantially air free sample from a trap 1000 into a microsieve 1010. In a microsieve 1010, a sample may be washed with a solution and/or analyzed. Residual reagents and/or discarded samples may be collected and/or contained in a waste reservoir 890 positioned in the cartridge 860. Collecting reagents and/or samples in a waste reservoir may facilitate hazard-free disposal of the cartridge.

Figure 8B:
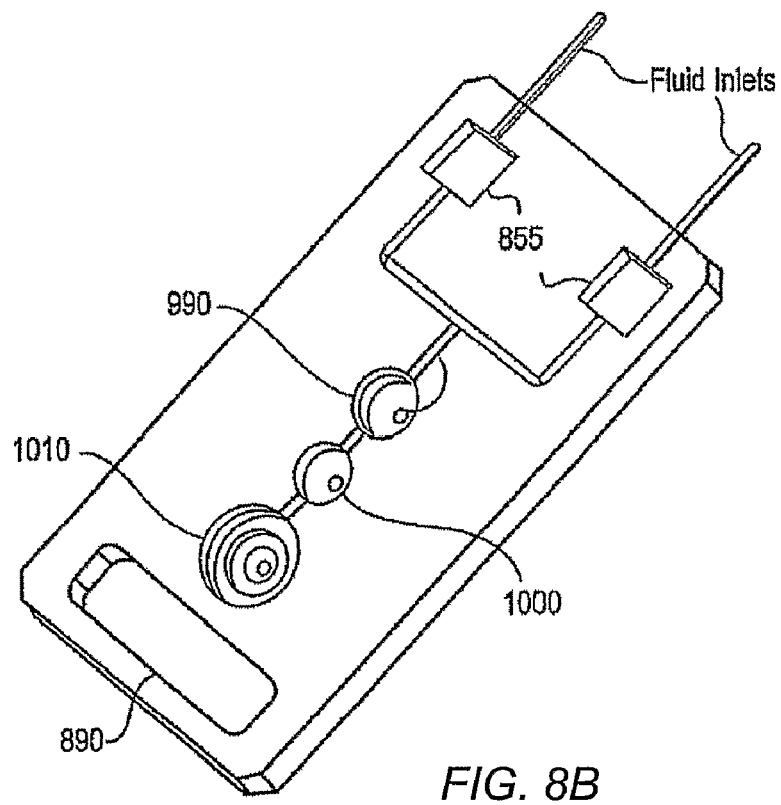

FIG. 8B depicts an embodiment of a cartridge including reagent packs. A reagent pack may be a pad 855 including one or more reagents that have been dried on a surface of the reagent pad. A reagent pack may include a pad with one or more reagents within the pad. In certain embodiments, reagents and/or a reagent pad may include one or more stabilizers. Stabilizers may increase reagent stability. During use, a sample may be deposited in a sample reservoir 990. Buffer may be delivered through fluid inlets and flow over reagent pads 855. When a buffer passes over reagent pads 855, one or more reagents may be reconstituted and delivered to a sample reservoir 990. In one embodiment, a buffer may reconstitute a desired reagent on a reagent pad 855. A buffer solution containing the reconstituted reagents may pass into a sample reservoir 990 and react with a sample. A fluid delivery system may then push the chemically modified sample (e.g., the sample reacted with one or more reagents) into a trap 1000. In the trap 1000, air may be released from the chemically modified sample. Further pressure or actuation may push the air free sample into a microsieve 1010 of a cartridge 860. In a microsieve 1010, a chemically modified sample may be washed and/or analyzed. Residual reagents and/or discarded samples may flow to a waste reservoir 890 to reduce hazards during disposal.

Figure 8C:
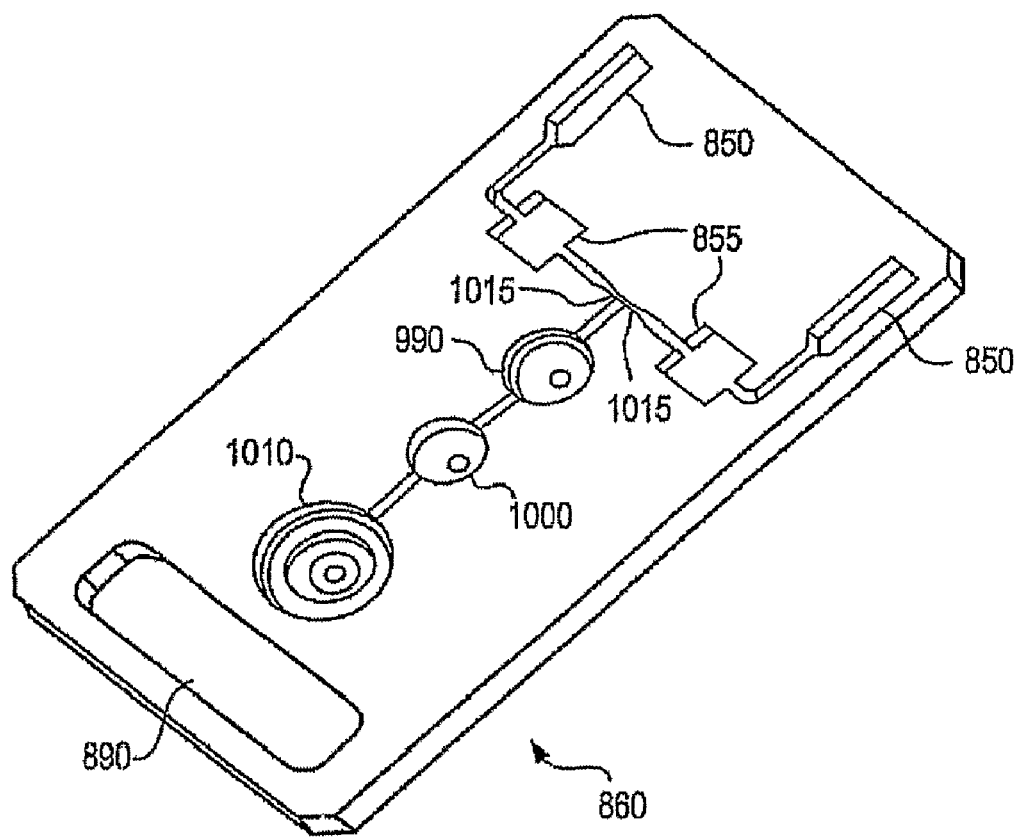

In some embodiments, a combination of reagent reservoirs, reagent packs, and/or reagent pads may be positioned in a cartridge, as depicted in FIG. 8C. Reagent packs and/or reservoirs 850 may be coupled to reagent pads 855 such that pressure on the reagent packs 850 may deliver one or more reagents to one or more reagent pads 855. Reagents from the reagent packs 850 may reconstitute one or more reagents on the reagent pads 855. Further actuation may force the reagents from the reagent pad to the sample reservoir 990. For example, an actuated lever may apply pressure to reagent packs and force reagent through one or more channels connecting one or more reagent packs and a sample reservoir. A channel may direct reagent from a reagent pack to flow over a reagent pad. In some embodiments, a cartridge 860 may include passive valves 1015, as depicted in FIG. 8C. Passive valves provide a path of least resistance to flow. Passive valves 1015 may be used to facilitate fluid flow towards a sample reservoir 990 and/or other areas of the cartridge 860. A fluid delivery system may then push the chemically modified sample (e.g., the sample reacted with one or more reagents) into a trap 1000. In the trap 1000, air may be released from the chemically modified sample. Further pressure or actuation may push the air free sample into a microsieve 1010 of a cartridge 860. In a microsieve 1010, a chemically modified sample may be washed and/or analyzed. Residual reagents and/or discarded samples may flow to a waste reservoir 890 to reduce hazards during disposal.

In some embodiments, disposable cartridges may include reagent pads. Reagent pads may store reagents in a self-contained manner that may provide increased stability, reduce and/or eliminate reagent aggregation and/or precipitation (e.g., clumping) and increase effective reagent concentrations. Increasing effective reagent concentrations may reduce response times for sample analysis. Disposable, self-contained cartridges may have important implications for point-of-care diagnostics, such as, not requiring refrigerated storage nor reagent preparation and/or not requiring handling of waste material. Cartridges may allow fast and inexpensive diagnostics to be transported to and performed in situations where time is critical.

Figure 8D:
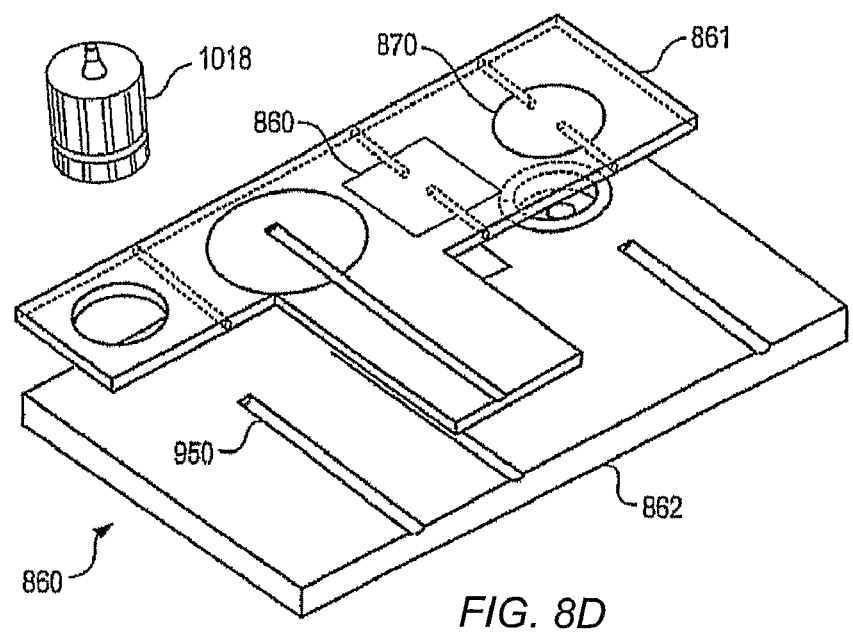
FIG. 8D depicts an exploded view of a cartridge with a reagent capsule.
Figure 8E:
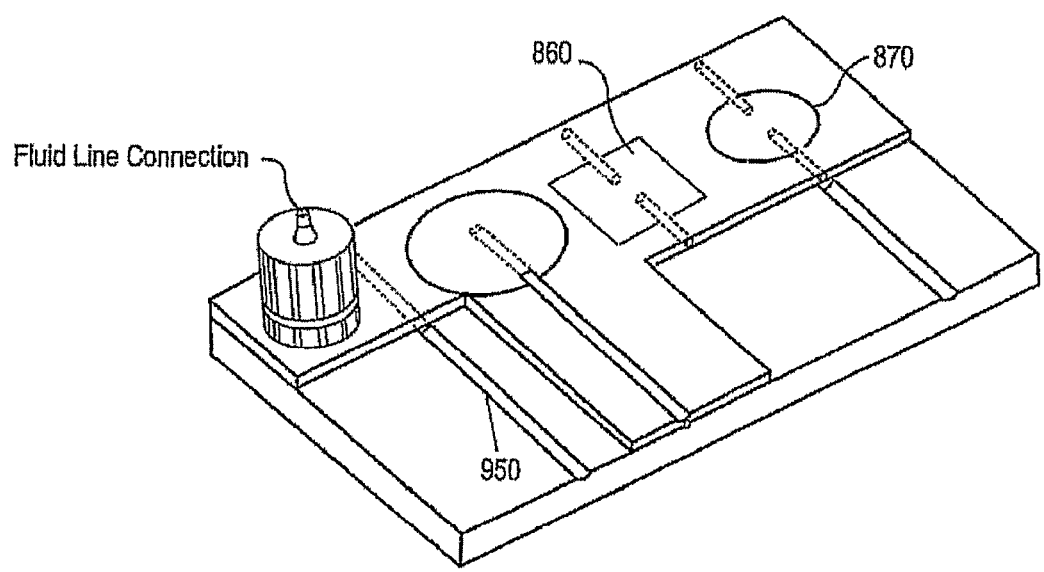
FIG. 8E depicts a schematic diagram of a cartridge with a reagent capsule.

In some embodiments, a reagent capsule including one or more reagents may be coupled to a cartridge. Reagent capsule may include liquid and/or dried (e.g., reagents in solid or powder form) reagents. In one embodiment, a reagent pad with dried reagent on the pad may be positioned in the reagent capsule. FIG. 8D depicts an exploded view of an embodiment of a reagent capsule 1018 coupled to a cartridge 860 including microsieve analysis regions. A cartridge 860 may include a top portion 861 and a bottom portion 862. A reagent capsule 1018 may be coupled to the cartridge 860 such that channels 950 coupled the reagent capsule to a trap and/or microsieve portion 870 of the cartridge. FIG. 8E depicts an embodiment of a reagent capsule 1018 coupled to a cartridge 860 including microsieve 870 analysis regions. A sample may enter a reagent capsule 1018 via a fluid connection line and flow via channels 950 in the cartridge 860 to the microsieve 870 analysis regions. In some embodiments, a cartridge may include reagent delivery systems, such as a reagent pack, a reservoir containing reagent, and/or a regent pad. In some embodiments, a cartridge includes a reagent delivery system that includes a reagent pack and reagent pad. During use, a sample may be deposited in a sample reservoir and reagents may be delivered to the sample reservoir by actuation. In one embodiment, an actuator may apply pressure to a reagent pack and force reagent through a channel, over a reagent pad and into the sample reservoir where the reconstituted reagents react with the sample. Further actuation may cause the chemically modified sample into a trap where substantially all of the air in a sample may be released. The chemically modified, air free sample may be forced by actuation onto a microsieve of a cartridge. In a microsieve of a cartridge, a sample may be washed and/or analyzed. Residual reagents and/or sample may flow into a waste reservoir after analysis to reduce the risk of hazard during disposal.

In some embodiments, a cartridge self-positioning system may perform two functions. First, the system may be used to align (manually or automatically) the area(s) of the cartridge containing the sample to be analyzed with the instrument's optical platform. Second, the self-positioning system may reposition the cartridge such that multiple areas of the sample may be analyzed in sequence.

Figure 9:
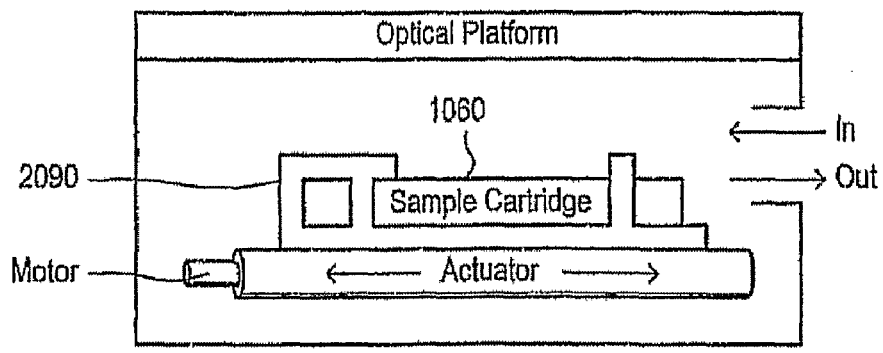
FIG. 9 depicts a schematic diagram of a cartridge self-positioning system.

A cartridge self-positioning system may include at least two components, as shown in the embodiment of a cartridge self position system depicted in FIG. 9. One component is an apparatus 2090 that may hold or secure the cartridge 1060 in place. An example of such is an apparatus that functions analogous to a computer disk mount. In operation, such a device would accept and/or eject a disposable cartridge into/out of the analysis instrument.

A second component of the cartridge self-positioning system may be hardware, software, and/or firmware capable of registering and verifying the position of the disposable cartridge in relation to the optical components of the analysis instrument. For example, position registration hardware may be comprised of an x- and/or y-motor-driven translation stage in which position is tracked by counting the motor's steps to or from a home position. Alternative embodiments of position registration hardware include, but are not limited to: a motorized micrometer or actuator, a piezo-electric actuator coupled to an optical positioning device, an encoder wheel gear monitored by a sensor, and/or a manual translation stage or micrometer.

An instrument may include one or more optical platforms. An instrument's optical platform may acquire images of a sample, and/or of sample-modulated detection regions. An optical platform may translate the acquired images into meaningful values. Images, in some embodiments, may include captured spectroscopic changes within the optical platform. In one embodiment, components of an optical platform may include one or more light sources, one or more lenses, one or more dichroic mirrors, one or more photodetectors, one or more emission filters, and/or one or more excitation filters.

The one or more light sources may include a collimated, monochromatic light source, such as a diode laser; a white light source, such as a tungsten-halogen lamp; and/or light emitting diodes (LEDs). Optionally, one or more light sources may be modulated using a transistor-transistor logic (TTL) pulse, an electronic shutter and/or an on/off switch. The one or more light sources may emit light suitable for the excitation of one or more reporter or encoding labels present in the sample and/or on particles contained within the device (e.g., fluorophores; chromophores; luminophores such as single dyes, tandem or conjugate dyes; particles; and/or a combination or multiplex thereof). The excitation of each species may cause one or more spectroscopic changes, such as intensity, lifetime, spectral characteristics, and/or polarization. An optical detector may include one or more detectors. Detectors (e.g., an array detector such as a charge-couple device camera) may measure the resulting properties of the excitation of each species. One or more processors equipped with software may translate each measured property to a meaningful value.

Figure 10A:
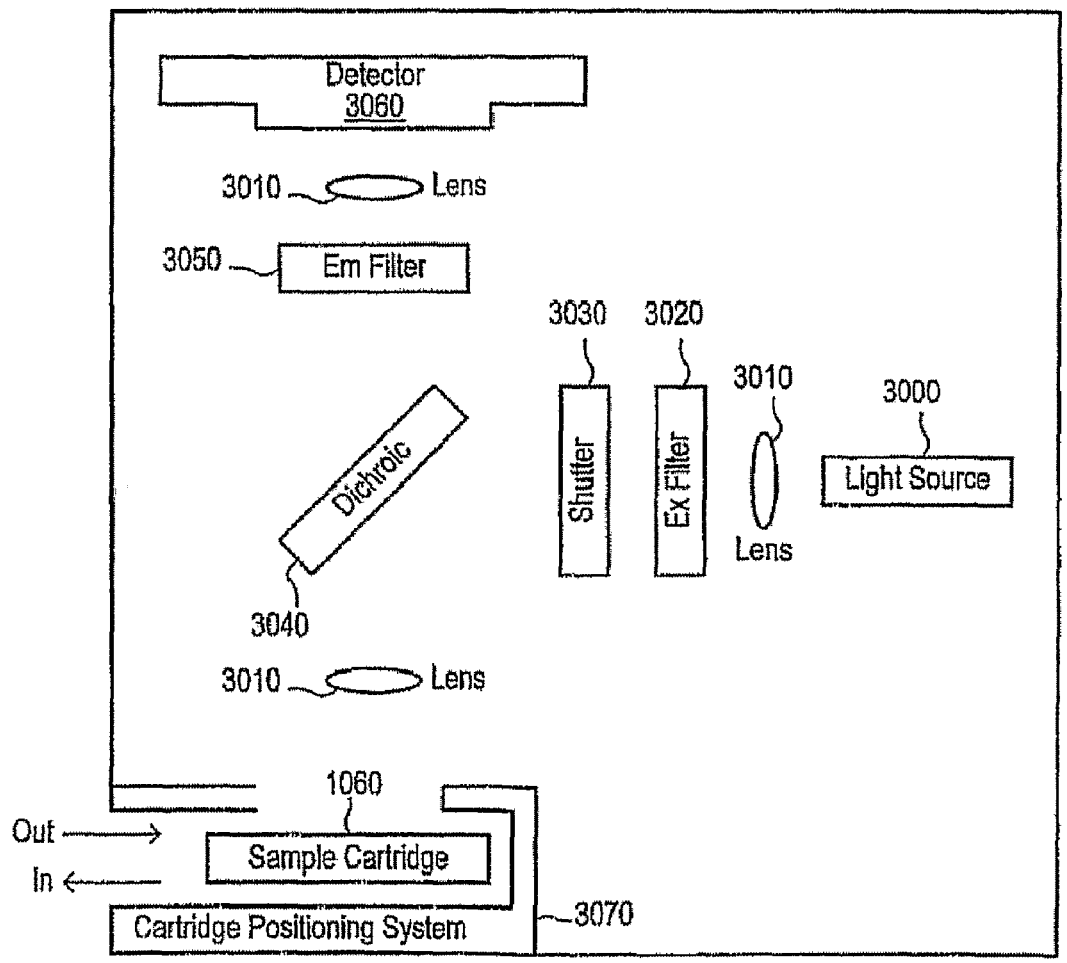
FIG. 10A depicts a schematic diagram of an optical platform.

In one embodiment, shown in FIG. 10A, an optical platform may include a light source 3000, focusing lenses 3010, at least one excitation filter 3020, an electronic shutter 3030, a dichroic mirror 3040, at least one emission filter 3050, and/or an array detector 3060. In one operation, the sample cartridge 1060 containing sample reacted with one or more fluorescent reporter labels, may be placed in a cartridge positioning system 3070. The positioning system 3070 aligns the sample area with the optical path. Light from the excitation source 3000 may be collimated with a lens 3010, filtered to the appropriate wavelength, passed through an open shutter 3030, reflected 90° by a (long pass or multi-bandpass) dichroic mirror 3040 and focused onto the sample using a lens 3010. The excitation light 3000 may excite one or more fluorophores present in the sample. The fluorescence emission from excited fluorophores may be collected by a 3010 lens and transmitted through the dichroic mirror 3040, filtered 3050 to the appropriate wavelength(s) and imaged with a detector 3060, such as a CCD camera. Fluorescence images may be processed and a meaningful value may be reported to an operator. While the above description is specific for fluorescent changes, it should be understood that the system may be modified to capture any kind of spectroscopic change.

Figure 10B:
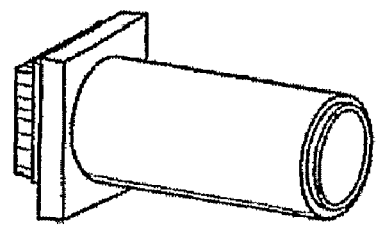
FIG. 10B depicts an embodiment of a light emitting diode assembly.
Figure 10C:
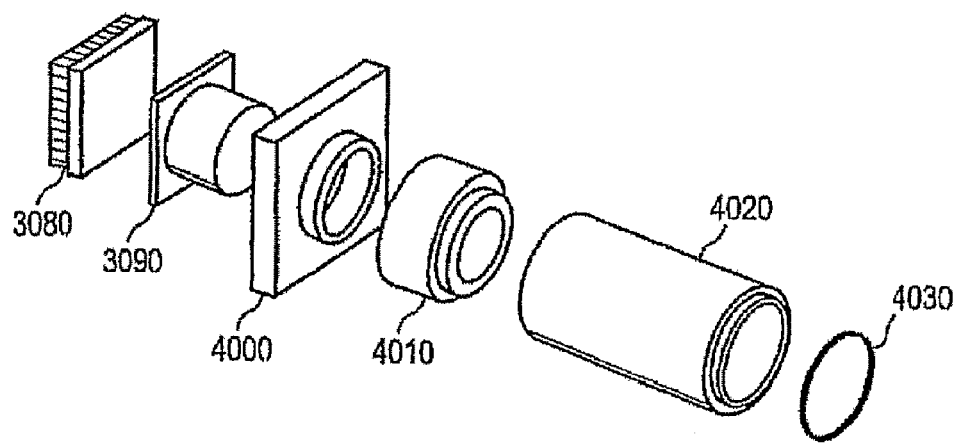
FIG. 10C depicts an exploded view of an embodiment of light emitting diode assembly.

In some embodiments, a light emitting diode (LED) assembly may be used in place of a light source in an optical system. An embodiment of an LED assembly is depicted in FIG. 1038B. An exploded view of the LED assembly depicted in FIG. 10B is depicted in FIG. 10C. The LED assembly 3000 may include a heat sink 3080, a LED 3090, a mount 4000, a filter 4010, a lens tube 4020, and a focusing lens 4030.

Figure 11:
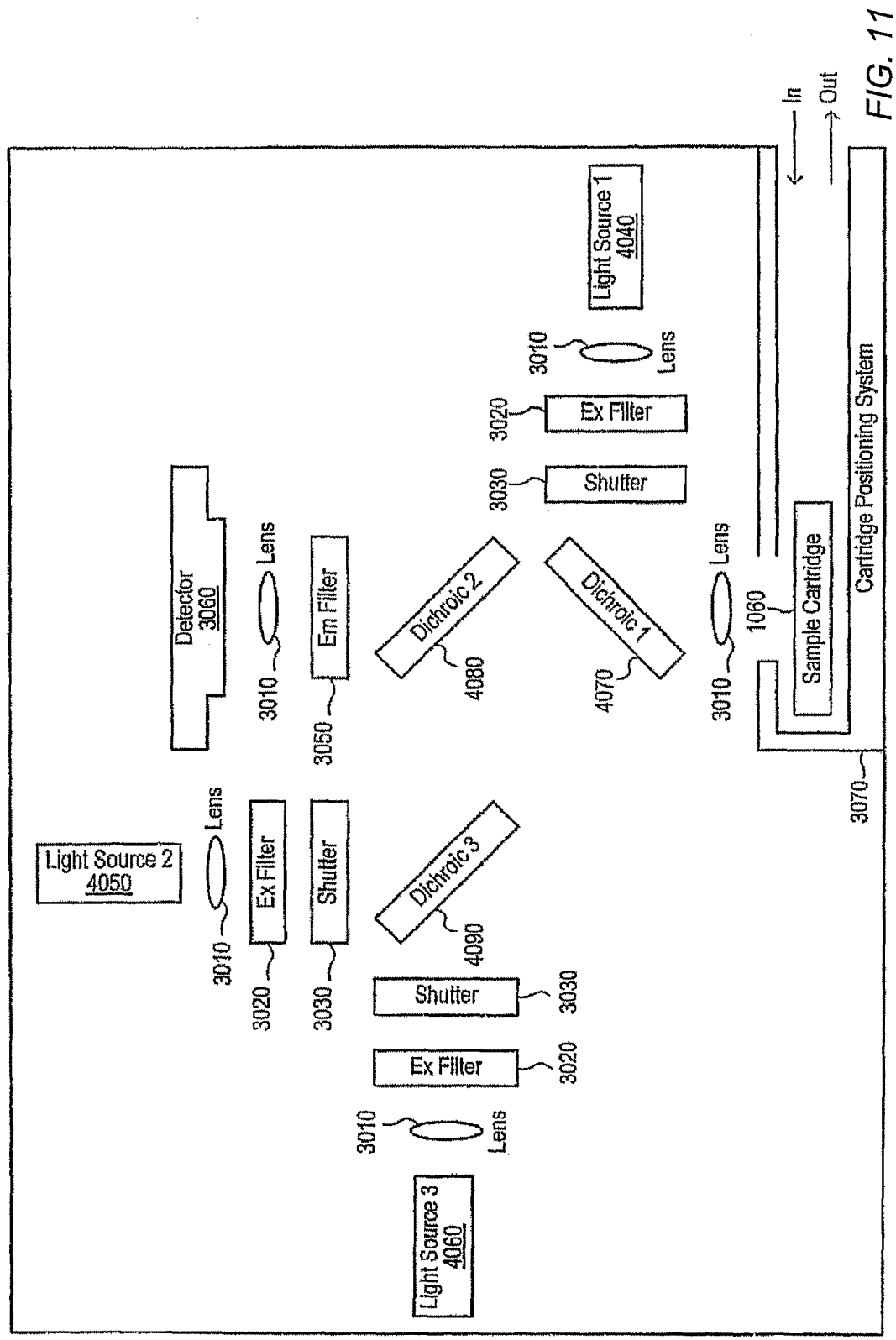
FIG. 11 depicts a schematic diagram of an optical platform that includes three light sources.

In a second embodiment, depicted in FIG. 11, the optical platform includes three LED light sources 4040, 4050, 4060 (e.g., blue, green and red); focusing lenses 3010 for each of the LED lights; three excitation filters 3020; three light source modulation units (e.g., electronic shutters) 3030; three dichroic mirrors 4070, 4080, 4090; at least one emission filter 3050; and an array detector 3060. In one embodiment, a sample cartridge 1060 containing sample reacted with one or more fluorescent reporter labels may be placed in a cartridge positioning system 3070. The cartridge positioning system 3070 aligns the sample area with the optical path. Blue light from excitation source 4040 may be collimated with a lens 3010, filtered to the appropriate wavelength, passed through an open shutter 3030, reflected 90° by a (long pass) dichroic mirror 4070 and focused onto the sample using a lens 3010. The blue excitation light may excite blue-excited fluorophores present in the sample. The fluorescence emission from the blue-excited fluorophores may be collected by a lens 3010, transmitted through dichroic mirrors 4070 and 4080 (multi-bandpass dichroic), filtered 3050 to the appropriate wavelength(s), and imaged with a detector 3060, such as a CCD camera. Next, green light from excitation source 4050 may be collimated with a lens 3010, filtered 3020 to the appropriate wavelength, passed through an open shutter 3030, reflected 90° by dichroic mirror 4090 (long pass), reflected 90° by dichroic mirror 4080 (multi-bandpass dichroic), transmitted through dichroic mirror 4070 (long pass) and focused onto the sample using a lens 3010. The green excitation light may excite green-excited fluorophores present in the sample. The fluorescence emission from the green-excited fluorophores may be collected by a lens 3010, transmitted through dichroic mirrors 4070 and 4080 (multi-bandpass dichroic), filtered to the appropriate wavelength(s), and imaged with detector 3060. Next, red light from excitation source 4060 may be collimated with a lens 3010, filtered to the appropriate wavelength, passed through an open shutter 3030, transmitted through dichroic mirror 4090 (long pass), reflected 90° by dichroic mirror 4080 (multi-bandpass dichroic), transmitted through dichroic mirror 4070 (long pass), and focused onto the sample using a lens 3010. The red excitation light may excite red-excited fluorophores present in the sample. The fluorescence emission from the red excited fluorophore may be collected by a lens 3010; transmitted through dichroic mirrors 4070 and 4080 (multi-bandpass dichroic); filtered 3050 to the appropriate wavelength(s); and imaged with a detector 3060. The three-color fluorescence images may then be processed and a meaningful value may be reported to the operator. While the above description is specific for fluorescent changes, it should be understood that the system may be modified to capture any kind of spectroscopic change.

Figure 12:
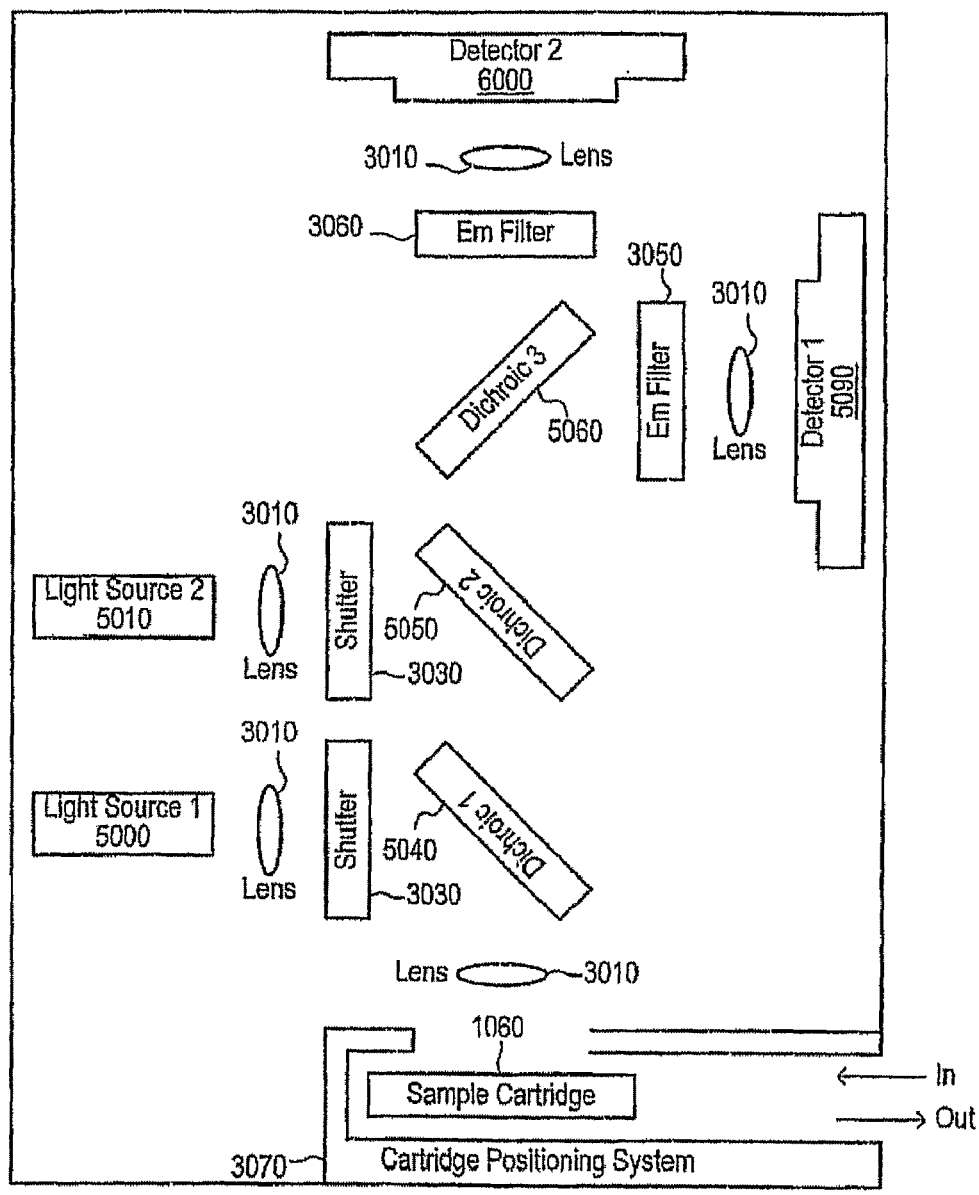
FIG. 12 depicts a schematic diagram of an optical platform that includes two light sources.

In an embodiment, shown in FIG. 12, images of multiple colors may be acquired simultaneously. In this embodiment, the optical platform includes two diode laser light sources (e.g., green and red) 5000, 5010; focusing lenses 3010; two light source modulation units (e.g., electronic shutters) 5020, 5030; three dichroic mirrors 5040, 5050, 5060; two emission filters 5070, 5080 and two array detectors 5090, 6000. A sample cartridge 1060 containing sample reacted with one or more fluorescent reporter labels may be placed into the cartridge positioning system 3070. The cartridge positioning system 3070 may align the sample area with the optical path. Green light from excitation source 5000 may be focused with a lens 3010, passed through an open shutter 3030, reflected 90° by (long pass) dichroic mirror 5040, and focused onto the sample using a lens 3010. The green excitation light may excite green-excited fluorophores present in the sample. The fluorescence emission from the green-excited fluorophores may be collected by a lens 3010, transmitted through dichroic mirrors 5040 (long pass), 5050 (dual-bandpass dichroic), reflected 90° by dichroic mirror 5060 (long pass), filtered 3050 to the appropriate wavelength and imaged with detector 5090. Simultaneously, red light from excitation source 5010 may be focused with a lens 3010, passed through an open shutter 3030, reflected 90° by dichroic mirror 5050 (dual-bandpass dichroic), transmitted through dichroic mirror 5040 (long pass), and focused onto the sample using a lens 3010. The red excitation light may excite red-excited fluorophores present in the sample. The fluorescence emission from the red-excited fluorophores may be collected by a lens 3010; transmitted through dichroic mirrors 5040 (long pass); 5050 (dual-bandpass dichroic) and 5060 (long pass); filtered 3060 to the appropriate wavelength; and imaged with detector 6000. The two-color fluorescence images may be processed simultaneously and a meaningful value may be reported to the operator. While the above description is specific for fluorescent changes, it should be understood that the system may be modified to capture any kind of spectroscopic change.

Figure 13:
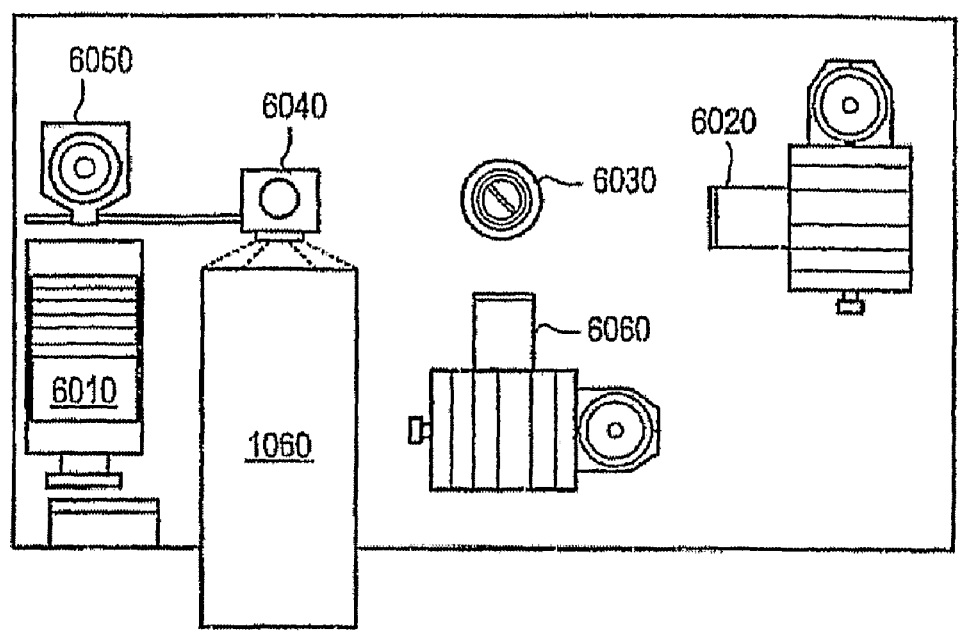
FIG. 13 depicts an optical platform that includes two laser light sources.

FIG. 13 is a schematic drawing of an embodiment of an optical system in which the light sources are laser diodes. A sample may be delivered to the sample cartridge 1060 using a syringe pump-based fluid delivery system 6010. Light from laser diode 6020 may be transmitted through dichroic mirror 6030, optionally filtered, reflected off dichroic mirror 6040, and focused onto the sample. Fluorescence from the sample is collected by the lens; reflected off dichroic mirror 6040; filtered to the appropriate wavelength; and imaged onto a detector 6050. Simultaneously, or in sequence, light from laser diode 6060 may be reflected off dichroic mirror 6030, optionally filtered, reflected off dichroic mirror 6040, and focused onto the sample. Fluorescence from the sample may be collected by a lens, reflected off dichroic 6040, filtered to the appropriate wavelength, and imaged onto a detector 6050. While the above description is specific for fluorescent changes, it should be understood that the system may be modified to capture any kind of spectroscopic change.

Optionally, an optical platform may include one or more optical fibers (e.g., single-core optical fibers, imaging fibers, bifurcated fibers, or a group thereof). Optical fibers may carry excitation light to the one or more labels present in the sample and may carry the emitted fluorescence properties to one or more detectors. Additionally, multiple fibers may be employed to image multiple regions of the sample area simultaneously, thus eliminating the need for sample cartridge actuation.

Figure 14:
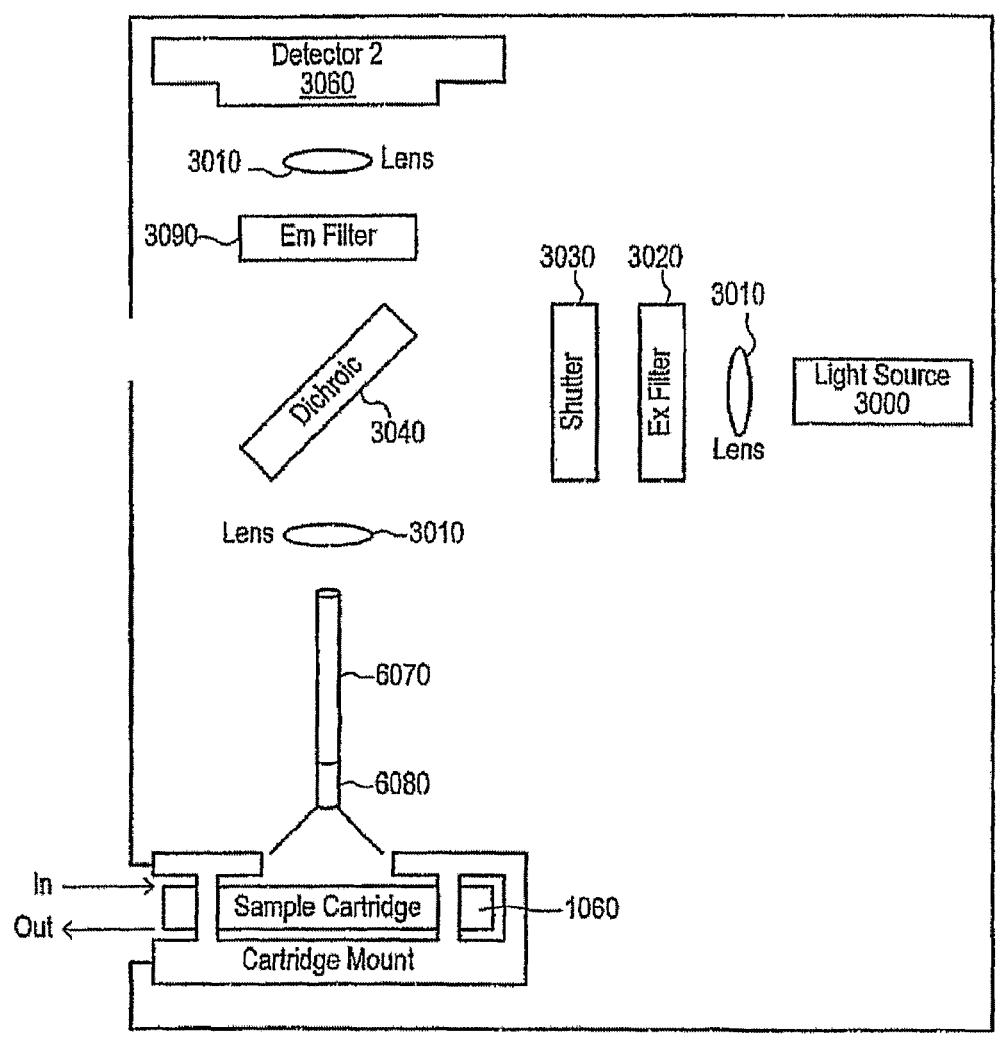
FIG. 14 depicts a schematic diagram of an optical platform that includes a single optical fiber microlens.

In one embodiment, shown in FIG. 14, an imaging fiber 6070 with a microlens 6080 (e.g., a GRIN lens) may be positioned in the optical pathway. Light from an excitation source 3000 may be collimated with a lens 3010, filtered 3020 to the appropriate wavelength, passed through an open shutter 3030, reflected 90° by a (long pass) dichroic mirror 3040, and focused onto the distal end of the fiber 6070 with a lens 3010. The excitation light may travel through the fiber 6070 and excite fluorophores present in the sample. The fluorescence emission from the excited fluorophores may be collected by the fiber's microlens 6080, transmitted through the fiber 6070, collected with a lens 3010, passed through a long pass dichroic mirror 3040, filtered 3050 to the appropriate wavelength(s), and imaged with a detector 3060. The fluorescence images may then be processed and a meaningful value may be reported to an operator. This optical platform may provide more uniform illumination and an increased field of view. While the above description is specific for fluorescent changes, it should be understood that the system may be modified to capture any kind of spectroscopic change.

Figure 15:
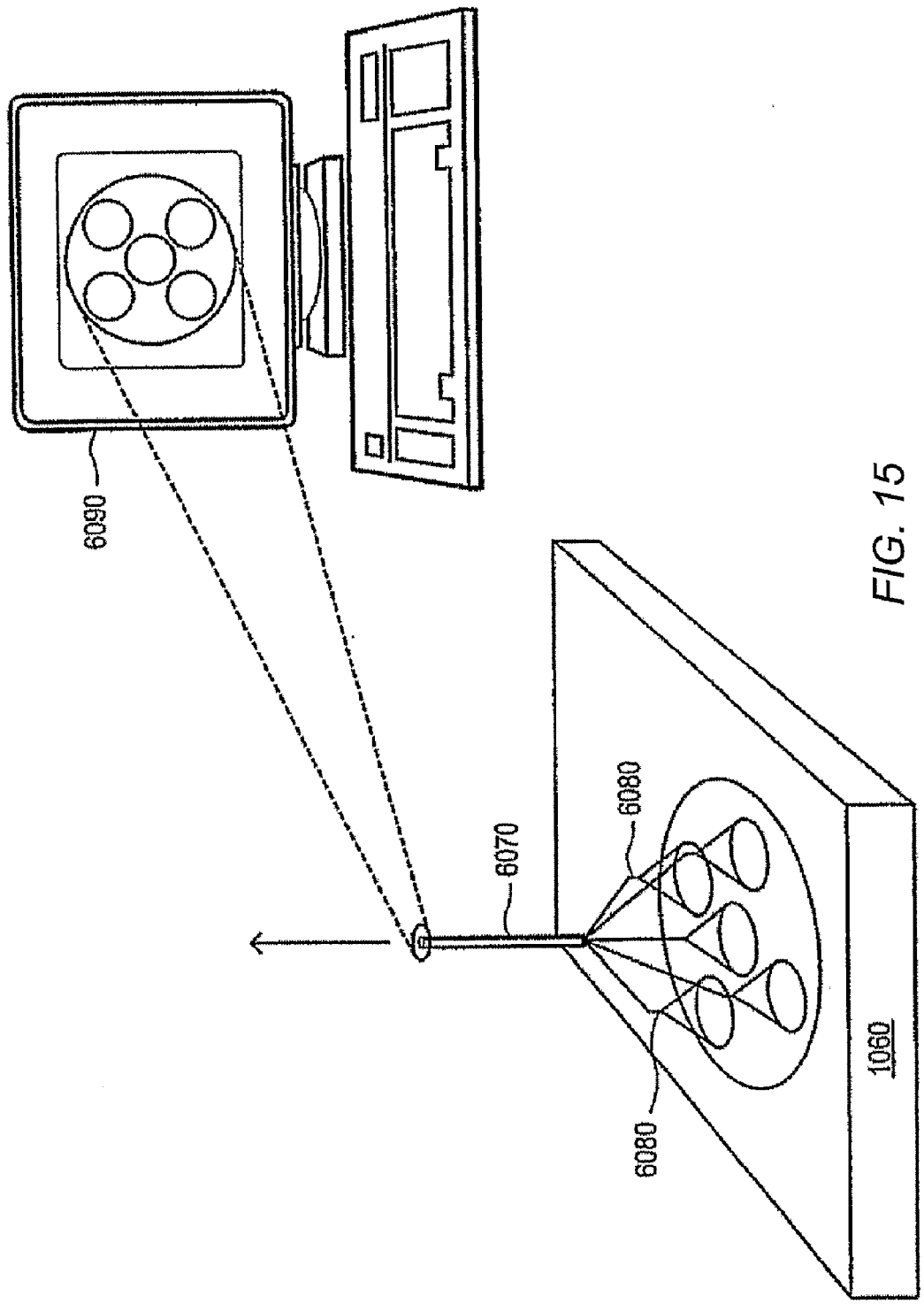
FIG. 15 depicts a schematic diagram of an optical platform that includes multiple optical fiber microlenses.

In another embodiment, shown in FIG. 15, multiple optical (imaging) fibers 6070 containing microlenses 6080, may be used to image simultaneously multiple regions of interest in the sample, eliminating the need to actuate the sample cartridge 1060. At the proximal end, the fibers may be separated at fixed positions, relative to the sample. At the distal end, the fibers may be bundled together. In operation, the light path is similar to previous examples, except that multiple areas of the sample are excited. The fluorescence emission from the multiple excited sample areas is collected by the fibers 6070 and imaged 6090 simultaneously with a CCD camera. The fluorescence image may be processed and a meaningful value may be reported to an operator. An advantage to using multiple optical fibers is that multiple areas can be imaged simultaneously with one image and without moving the sample and/or cartridge. While the above description is specific for fluorescent changes, it should be understood that the system may be modified to capture any kind of spectroscopic change.

An optical platform may display images detected by a detector on a computer. A computer coupled to the instrument may be a desktop, laptop, handheld or other computer equipped with commercial or custom software. The software may contain algorithms and/or neural networks for image analysis. Images may be analyzed by the computer for fluorescence properties, such as intensity, lifetime, spectral characteristics, polarization, absorption properties, luminescence properties, number of particles or some function thereof, size, shape or combination of any of these.

In another embodiment, an analyte detection device may include a cartridge that holds a microsieve-based detector. The cartridge may be a disposable cartridge and may act as the chemical and biochemical-sensing component of the analyte detection device. The cartridge, which shape may be adapted to various needs, may be composed of index-matching, molded or machined plastics, metals, glass or a combination thereof. In one embodiment, a cartridge may include one or more reservoirs for holding reagents, sample, buffer, fluids for analysis of samples, and waste that are connected via one or more microfluidic channels and/or valves. The cartridge may include one or more analysis and/or separation surfaces (e.g., microsieve or the like). A microsieve surface may trap and/or separate particulate matter of interest (e.g., cells, microbes, small pieces of tissue, polymer, glass or metal particles, or conjugates thereof).

Figure 16:
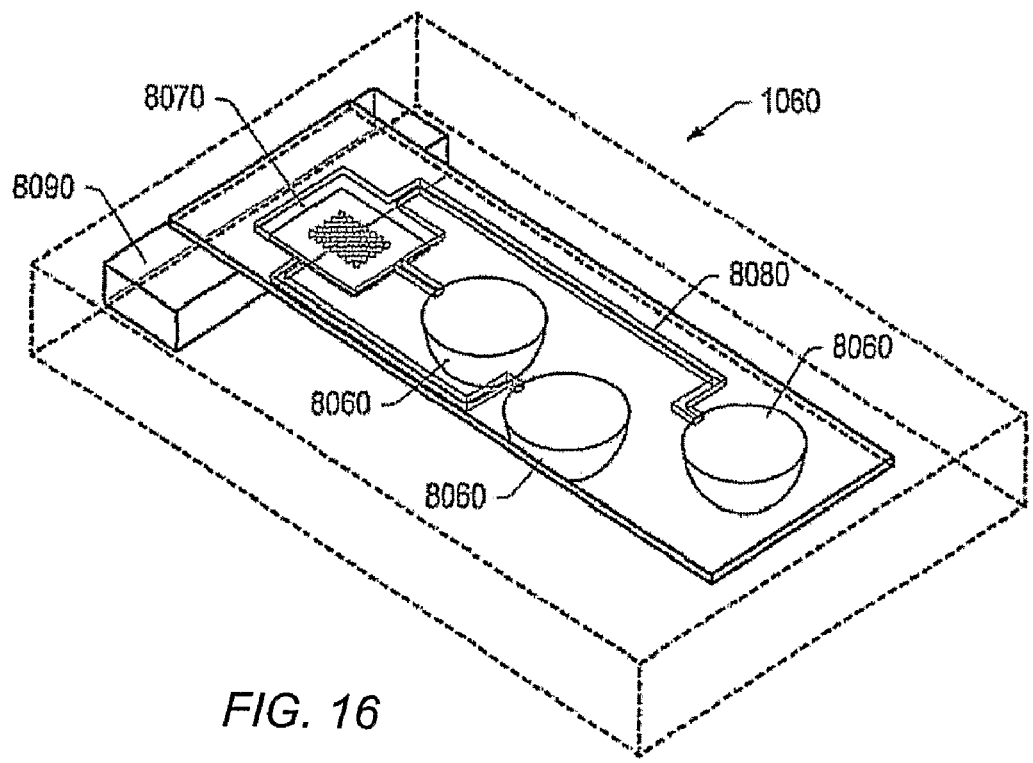
FIG. 16 depicts an embodiment of a disposable cartridge for use in the detection of analytes.

FIG. 16 depicts an embodiment of a single-use cartridge for use in the detection of analytes. Cartridge 1060 may be formed from a variety of materials, such as polymers, glasses, or metals. In one embodiment, a polydimethylsiloxane (PDMS) casting may be used. The cartridge 1060 may be designed to interface with a variety of peripheral fluidics systems. Alternatively, a pumpless design may be used by incorporating a customizable number of blister packs 8060, or substantially sealed reservoirs, into the cartridge 1060. Blister packs 8060 may include delivery fluids, reagents or other development fluids. Blister packs 8060 may be coupled to a detection system 8070 through microchannels 8080. Detection system 8070 may be a microsieve-based detection system. Reservoir 8090 may be used to collect the fluids from detection system 8070.

Figure 17:
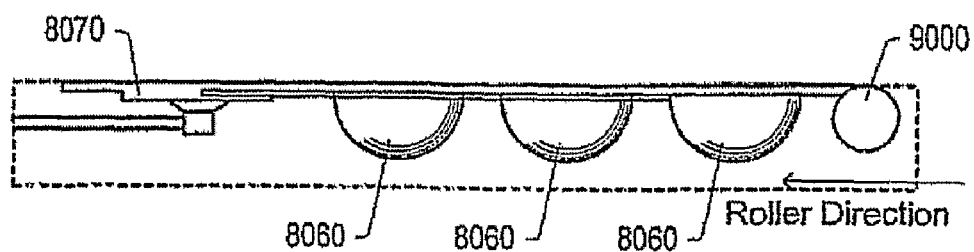
FIG. 17 depicts a roller system configured to force liquid from one or more blister packs disposed in a cartridge.

Blister packs 8060 may be used to deliver fluids to detection system 8070. Various activating systems may be used to force liquid from the blister through the microchannels 8080. Applying pressure to a blister pack may release delivery fluids, reagents, and/or other development fluids. Increasing pressure applied to blister pack may increase the amount of fluid delivered from the pack. In one embodiment, depicted in FIG. 17, liquid may be forced from blisters 8060 using a roller 9000. Contact of roller 9000 against blister 8060 may force liquid from blister toward detection system 8070.

Figure 18A:
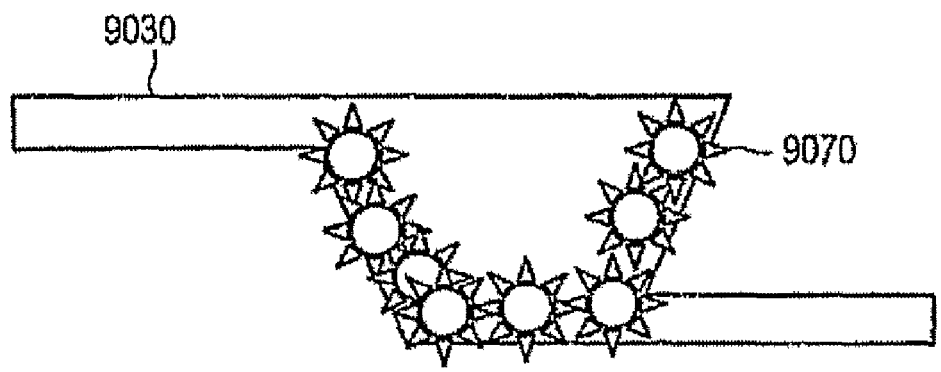
FIGS. 18A-C depict a sequence of steps for reacting a sample with a reagent in a mixing chamber.
Figure 18B:
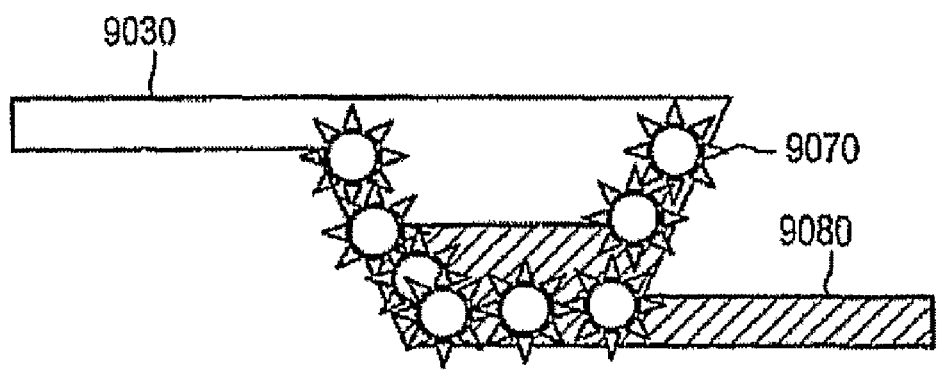
Figure 18C:
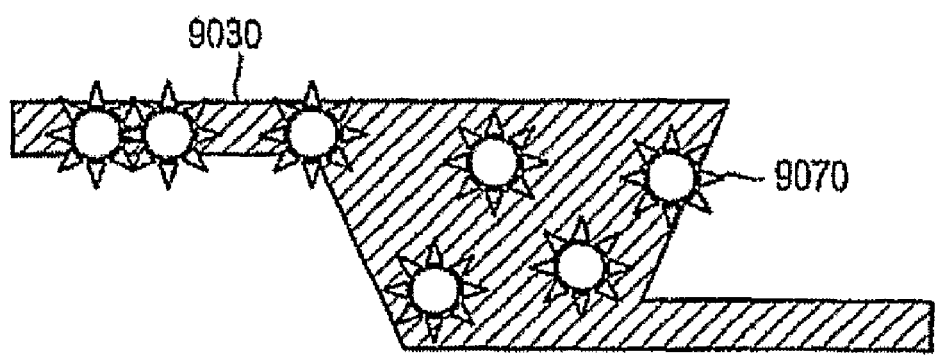

In one example, reagents may be stored in a lyophilized form. FIG. 18A depicts lyophilized reagents 9070 disposed in a mixing chamber 9030. Lyophilized reagents 9070 may be mixed with the sample 9080 upon introduction of the sample into mixing chamber 9030 of the cartridge, as depicted in FIG. 18B. Once the chamber 9030 is filled with the sample, the mixture of the sample and reagents 9070 will flow out of the chamber to other parts of the cartridge based on the positioning of microfluidic valves in the cartridge, as depicted in FIG. 18C.

Figure 19C:
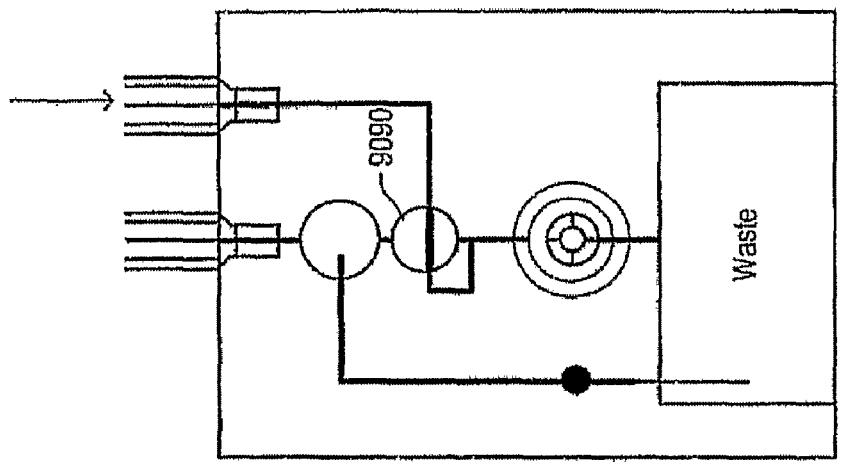
FIGS. 19A-C depict a series of schematic diagrams showing the operation of a cartridge.
Figure 19B:
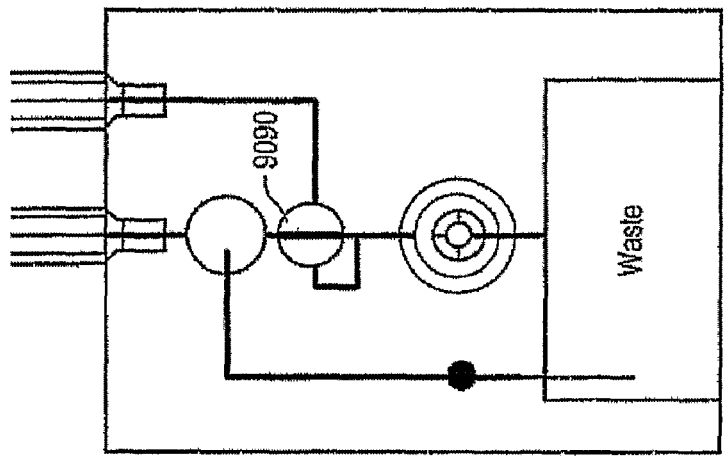
Figure 19A:
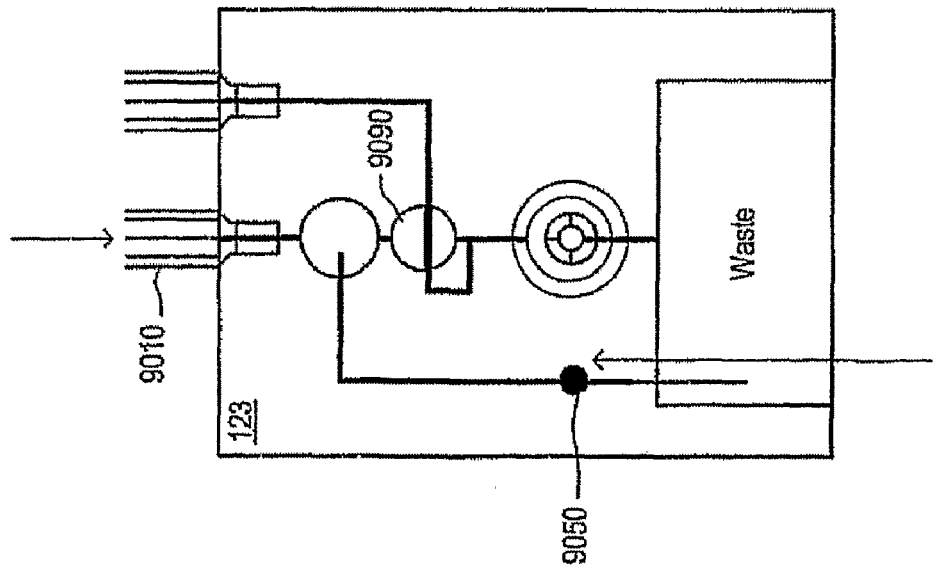

FIGS. 19A-C depict a series of schematic diagrams showing an embodiment of the operation of the cartridge. Valves may be actuated electro-mechanically and/or manually through a keypad of a reader enclosing the cartridge. Various combinations of valves and actuators may be used to build various fluidics circuitries depending on the number and nature of the reagents needed for each application. For example, as depicted in FIG. 19A, the sample is introduced through the sample introduction port 9010. The microfluidic valve 9090 may be placed in an orientation that blocks flow of the sample to the detection system, as depicted in FIG. 19A. Thus, as the sample exceeds the customizable metered volume of the mixing chamber, the sample overflows and passes through a sample check 9050 channel and into a waste reservoir. The sample may be thus observed through an opening in the reader/cartridge assembly. After an incubation time typical of each application, delivery of the sample to the microsieve is actuated, after switching of one or more microvalves 9090, as depicted in FIG. 19B. Once the desired sample volume has been delivered to the flow cell, the microvalve systems 9090 are actuated to allow passage of rinsing reagents through the microsieve, as depicted in FIG. 19C.

Figure 20:
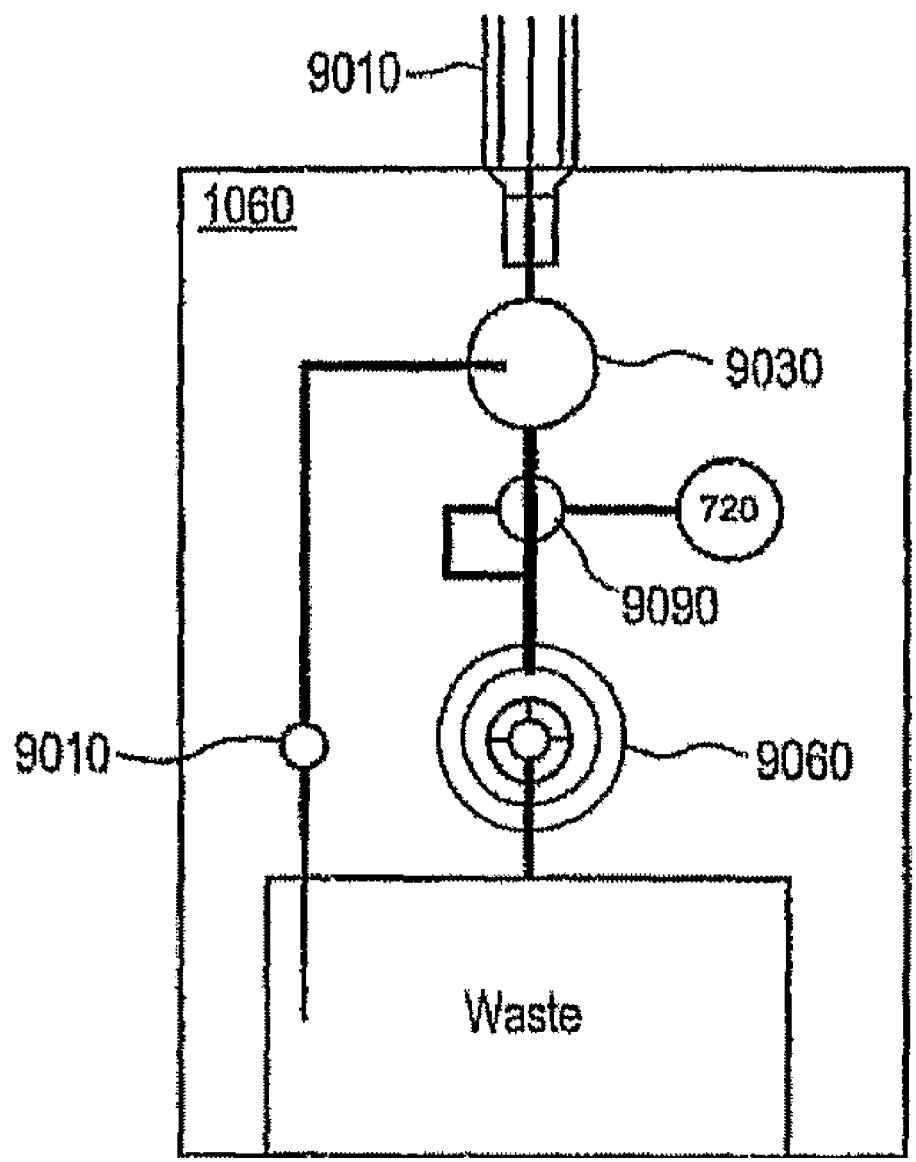
FIG. 20 depicts a schematic drawing of an alternate embodiment of a cartridge.

An alternate embodiment of a cartridge is depicted in FIG. 20. The cartridge 1060 includes a single input connector 9010 for sample introduction. The sample introduction port 9010 allows samples to be introduced into the cartridge 1060. Samples introduced into the cartridge 1060 may be conducted through channels into a mixing chamber 9030. In the mixing chamber, analytes in the sample may mix with reagents previously placed in the mixing chamber. The reagents may interact with the analytes in the sample to aid in visualization of the analytes. In one embodiment, cartridge 1060 may include a microfluidic valve 9090. Microfluidic valve 9090 may be used to control flow of the fluid through the cartridge 1060. Flow of the sample fluids may be directed through sample check window 9050 or to the microsieve 9060 for detection of the analytes. Fluids passing through the microsieve may be collected in waste reservoir. In one embodiment, fluids that pass through the sample check window 9050 may also be collected in the waste reservoir. The cartridge may include one or more blister packs 720. The blister packs 720 may be pressurized using either manual or automatic means to force liquid from the blister pack into the cartridge 1060. In an embodiment, the blister pack 720 may include a fluid for washing the microsieve-based detection system (e.g., a PBS buffer solution).

Figure 21A:
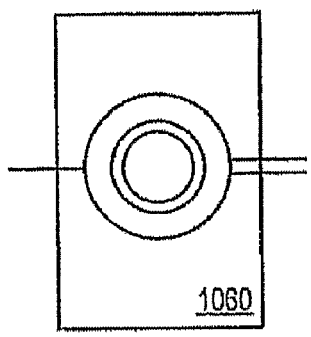
FIGS. 21A-C depict different embodiments of inlet and outlet channels in a cartridge.
Figure 21B:
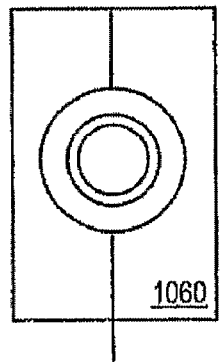
Figure 21C:
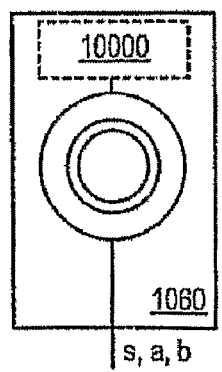

A cartridge may include a microsieve-based detection system and optionally, additional detection systems. A cartridge may be easily customized to accommodate various needs. A cartridge may include a combination of valves, channels, chambers, connectors to allow easy use and access. For example, cartridges 1060 shown in FIGS. 21A and 21B may be accommodated with an inlet, outlet, and lateral flow outlet that may be positioned in various configurations to accommodate various geometries of the fluid delivery. Additionally, a cartridge may be made with a built-in waste reservoir 10000 as depicted in FIG. 21C. The waste reservoir may be designed to handle bio-hazard materials. In an embodiment, a waste reservoir 10000 may be removable from a cartridge 1060 and safely replaceable.

Multiple channels may be created in a cartridge to allow the delivery to the detection system of a variety of reagents separately, as depicted in FIG. 22A. The reagents may be delivered to the microsieve-based platform 10010 of a cartridge 1060 through standard or customized connectors 10020. These connectors may allow delivery of reagents to the microsieve through syringes (e.g., using Luer fittings), or any standard or customized fittings to accommodate a variety of fluid delivery devices. Reagents may be pre-packaged within the cartridge and delivered to the detection system through capillary action or various actuation methods. FIG. 22B depicts an embodiment of a cartridge in which the sample may be deposited or introduced to a chamber 10030 where it is drawn to the microsieve-based platform 10010 of a cartridge 1060 through capillary action, actuation, or pump action. FIG. 22C depicts an embodiment of a cartridge 1060 that may include a combination of standard or customized connectors 10020, and reagent chambers 10030 that may be actuated. This cartridge also may include a "bull's eye" window where the sample is delivered to a metered chamber. Observation of sample through the "bull's eye" indicates overfilling of the chamber to a waste reservoir, and readiness of the metered volume of sample to be delivered to the microsieve. FIG. 22D depicts a diagram of an embodiment of a cartridge 1060 with one or more connectors and/or chambers 10030 modified to receive a capillary collection tube 10040 that includes an analyte. The capillary tube inner surface may be modified with a blood anti-coagulant. An inner surface of the capillary tube may be coated with an antibody mixture or other chemical or biological species used in the detection. The capillary 10040 is then introduced to the cartridge where the sample may be delivered to a microsieve-based platform 10010 in the detection system through capillary action, actuation, or pumps.

In some embodiments cartridges 1060 may include a trap 10050, which is used to inhibit air from flowing to the detection system, as depicted in FIG. 23A. Using a trap 10050 may release air from a sample flowing from a capillary 10040 or sample collection device to a microsieve-based platform 10010. A similar system including a built-in removable waste reservoir 10070 is shown in FIG. 23B. The cartridge depicted in FIG. 23B may also include a lateral flow outlet 10080 that may be directly coupled to the trap 10050 in order to remove bubbles from the cartridge.

In order to detect the presence of an labeled analyte, a means of visualizing detectably labeled analytes is required. This may include adding a detectable label to the analyte-bound particles.

In an embodiment, the analyte detection system may be coupled to an optical imaging station. The optical imaging station may include, for example, a microscope capable of visualizing the signals emitted from the particles or detectable label and/or capable of determining the size of the particles. A detector may be used to capture images of the microsieve-captured particles. A detector may include a detection device, such as a CCD digital imaging apparatus, and analytical software that is capable of analyzing digital images, such as, for example, Image Pro 4.0 or the like. Suitable optical instrumentation and imaging software platform for use in the embodiments presented herein have been described above. In some embodiments, the analyte detection system coupled to an optical imaging station may provide a means for efficient capture of populations of analyte-specific particles and the static imaging of the analytes captured thereon.

In an embodiment, digital images of particles captured on a field of the microsieve may be acquired and the signals emitting from the particles may be analyzed. For example, in an embodiment where particle populations are defined by red fluorescence intensity, and the detecting receptor is defined by green fluorescence, optical imaging using a red dichroic filter would allow the identification of the particle type and its location on the microsieve (which may be referred to as the "particle address"), and optical imaging using a green dichroic filter would identify particle populations that have bound to the analyte of interest. In an embodiment, acquired images may be processed digitally. In an embodiment, digital processing may be automated to facilitate the simultaneous detection and analysis of multiple populations of particles. Conversely, in alternate embodiments, a user may define areas of the microsieve to be processed further. Automated digital processing of acquired images may allow: the rapid identification of the location of particles and the identification of the corresponding population to which they belong; the identification of particle populations that are specifically bound to an analyte; and the quantitation of the analyte in the fluid sample. Quantitation of the analyte in the fluid sample may be determined by measuring the intensity of the fluorescent signal emitted from the detecting receptor.

Figure 24A:
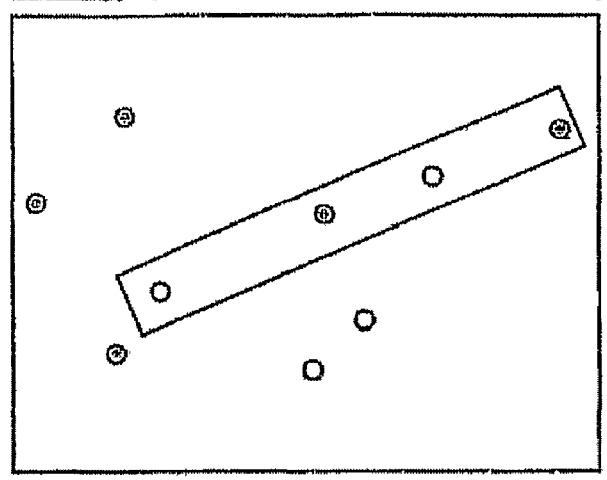
FIGS. 24A-B depict an embodiment of polystyrene particle types defined by size and by fluorescence signal intensity.
Figure 24B:
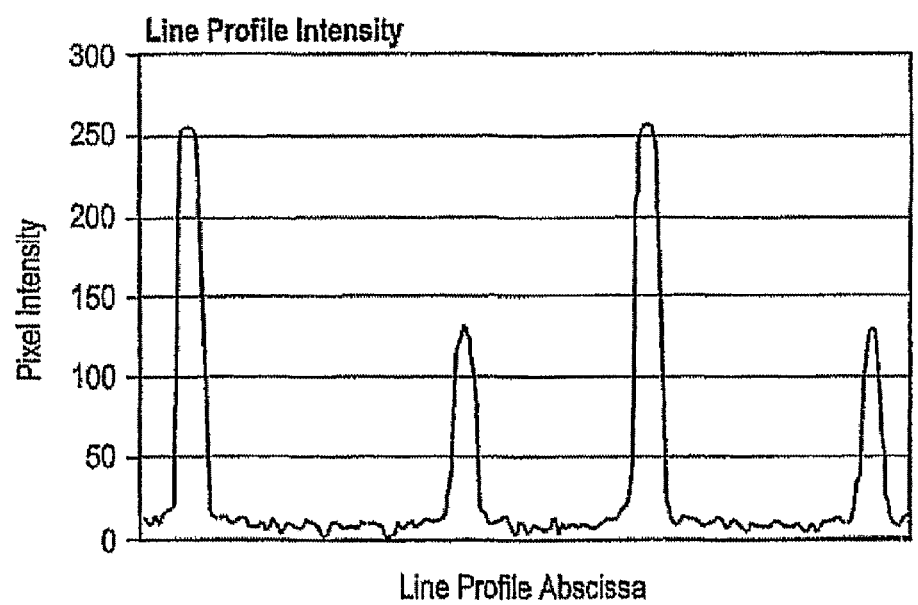

FIG. 24A-B depicts populations of polystyrene particles that are defined by size and by fluorescence signal intensity. FIG. 24A shows an image of particles captured on a microsieve according to an embodiment. In this case, two different populations of particles are shown. The particles in this image are of the same size, but each population of particles is coupled to different amounts of an internal red fluorescent dye. These two populations of particles were mixed together, captured on a microsieve in a flow cell and imaged optically using a red dichroic filter. FIG. 24A shows a view of an embodiment where polystyrene particles of the same size are distinguished on the basis of red fluorescence intensity. Particles of high fluorescence intensity are shown as open circles, and particles of lower fluorescence intensity are shown as shaded circles. FIG. 24B shows a line profile analysis of the particles in the boxed area of FIG. 24A. In this case, fluorescence intensity (measured as pixel intensity) is depicted as a function of the line profile. Confirmation that only one size of particles is present in the mixed population of particles may be achieved by determining the width of each peak at half the maximal pixel intensity. Conversely, the presence of two populations of particles distinguished on the basis of fluorescence signal intensity may be demonstrated by the presence of two peak pixel intensities.

In embodiments where both the capturing receptor and the detecting receptor are antibodies, the method of analyte detection may be referred to as a "sandwich immunoassay." The detecting receptor may be directed to the same epitope on the analyte as the capturing receptor. Conversely, the detecting receptor may be directed to a different epitope on the analyte than the capturing receptor. As used herein, the term "epitope" generally refers to a region on a molecule that is recognized by and that binds to the antigen binding sites of an antibody. In an embodiment, the detecting receptor may be coupled to a dye that distinguishes the detecting receptor from the size- and/or color-coded particle population. For example, in an embodiment, a detecting antibody that binds to an analyte captured by a capturing antibody on the surface of first color fluorescent particles may be coupled to a second colored fluorescent dye. In such an embodiment, a positive test for the presence of an analyte would occur when a population of particles or labels appears having the first color when imaged optically using a first color filter, and the second color when imaged using a second color filter. Conversely, particles or label that have the first color, but do not appear to have the second color would indicate that the analyte is not present in the solution. In an embodiment, the concentration of an analyte in a solution may also be determined by measuring the fluorescence intensity of the second dye. In an alternate embodiment, the fluorescent dye that defines the population of particles may be coupled to the capturing receptor rather than being coupled to the particles.

In some embodiments, an instrument may include one or more disposable cartridges. Such an instrument may portable. In some embodiments, a cartridge may be designed such that the cartridge is removably positionable in an instrument. A cartridge may include one or more detection systems. Light from an optical platform of the instrument may pass onto a detection region and a detector in the optical platform may acquire images (e.g., visual or fluorescent) of the sample, and/or of sample-modulated particles.

Figure 25:
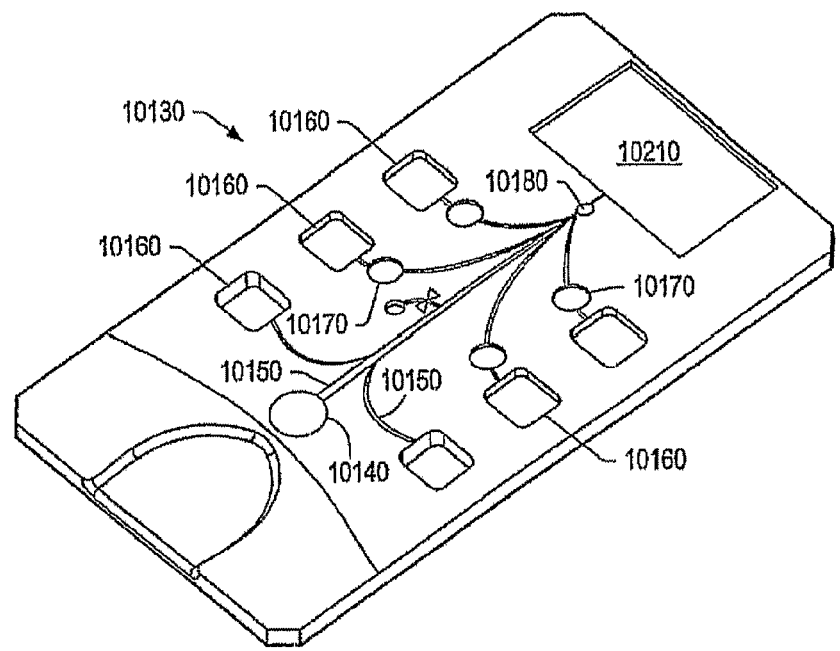
FIG. 25 depicts an embodiment of a cartridge that includes a sensor array.
Figure 26:
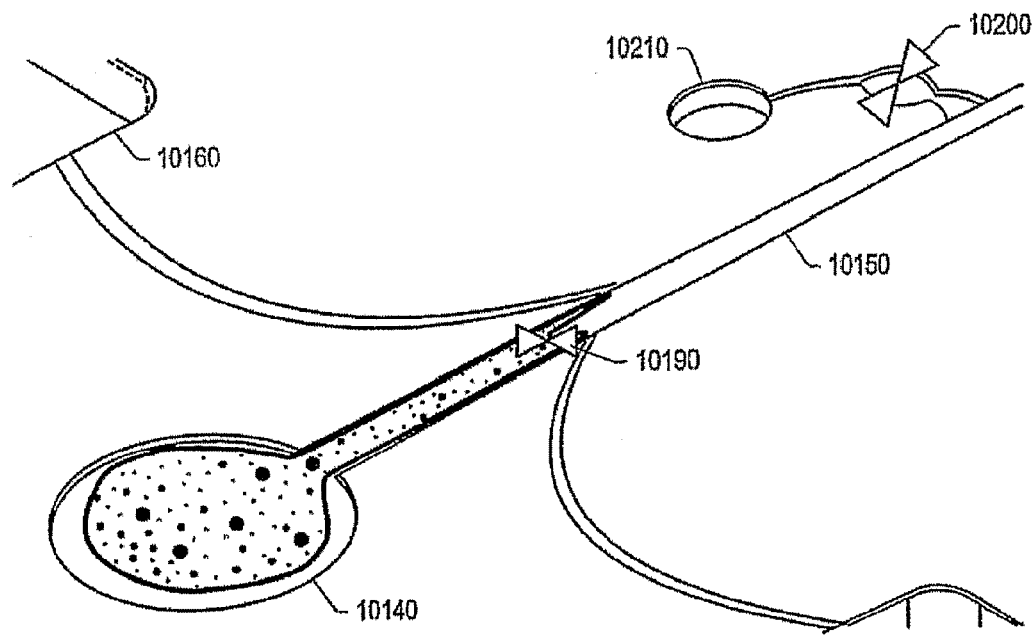
FIG. 26 depicts an embodiment of a portion of the cartridge depicted in FIG. 25.

FIG. 25 depicts an embodiment of a cartridge. FIG. 26 depicts an embodiment of a portion of the cartridge of FIG. 26. A cartridge 10130 may include a sample collection device 10140, as depicted in FIGS. 25 and 26. A sample may be delivered to the sample collection device 10140. In an embodiment, a sample collection device may include a sample pick-up pad. A sample may be introduced into the sample collection device. In one embodiment, a sample may be introduced into a sample collection device using a syringe or a pipette. Alternately, a sample may be introduced from a person directly to the sample collection device. For example, human blood may be introduced by forming a small incision in portion of a human body. The portion of the human body may be brought close to the sample pick-up pad such that blood flows from the incision in the human body to the sample pick-up pad.

Sample from the sample collection device 10140 may flow into one or more microfluidic channels 10150 coupled to the sample collection device. Capillary action may allow a sample to flow into a channel. A valve 10190 may restrict flow of sample from the sample collection device 10140. A valve 10190 proximate a sample collection device 10140 and a valve 10200 proximate an overflow reservoir 10210 in channel 10150 may be opened such that a predetermined amount of sample may be measured. During use the sample flows into channel 10150 until it fills the channel. The channel may hold a predetermined amount of fluid. An amount of sample greater than the predetermined amount may flow through valve 10200 into an overflow reservoir 10210. After a predetermined amount of sample is measured in channel 10150, valve 10190 and valve 10200 may be closed. Closing a valve 10190 proximate a sample reservoir may inhibit sample greater than a predetermined amount from flowing towards a detection region 10180. Closing a valve 10200 proximate an overflow reservoir 10210 may inhibit the predetermined amount of sample from flowing towards the overflow reservoir.

In some embodiments, a reservoir 10160 containing buffer and/or reagents may be coupled to a channel 10150. Fluid from the reservoir 10160 may push the predetermined sample towards a detection region. A buffer may be released from a buffer reservoir 10160 coupled by a channel to the channel containing the sample. In one embodiment, a buffer may be released from a reservoir 10160 by an actuator. Fluid from a reservoir may push the sample towards a mixing region or a detection region. A sample may mix and/or react with the fluid in a mixing region prior to flowing to a detection region. In certain embodiments, a reagent pick up pad 10170 may be positioned on a cartridge 10130 such that fluid from a reservoir 10160 may be able to flow over the reagent pick-up pad towards the detection region 10180. As depicted in FIG. 27, fluid from a reservoir 10160 may transfer reagents on a reagent pick-up pad 10170 into channel 10150. In some embodiments, reagents may be in a dehydrated or lyophilized state. Fluid from the reservoir may reconstitute and transfer the reagents as the fluid passes over the regent pick up pad 10170. Fluid from the reservoir 10160 containing reagents may be coupled to a detection region 10180 through a channel 10150. Detection region may include a microsieve-based system. Fluids in the cartridge 10130 may be collected in a waste reservoir 10190 after flowing past a detection region 10180, as depicted in FIG. 25. By containing all fluids within the cartridge, a user's exposure to reagents and sample may be substantially minimized.

In some embodiments, one or more reagents may be contained in a reservoir positioned on a cartridge. A reagent reservoir may include a blister pack, as depicted in FIG. 28A. FIG. 28B depicts a cross-sectional view of an embodiment of a blister pack. A blister pack may include one or more reagents in a sealed reservoir. A sealed reservoir may substantially contain reagents in the reservoir until needed. Pressure applied to a blister pack may break one or more surfaces of the blister pack such that reagent is released from the blister pack. In an embodiment, a blister of a blister pack may be formed of a first material 10220 and a second material 10230, where a second material is configured to rupture or break prior to the first material when pressure is applied to the blister. In an embodiment, a blister may include a first material configured not to break when pressure is applied to a blister and a second material configured to break when pressure is applied to a blister. A blister may be made of polyvinyl chloride (PVC); polyvinylidene chloride (PVDC); polyethylene (PE); polypropylene (PP); polyacrylonitrile (PAN); cyclic olefin copolymer (COC); fluoropolymer films; foil such as aluminum foil or plastic foil; and/or combinations thereof. A wall of a blister may be formed of layers of polypropylene, cyclic olefin copolymer. For example, a blister wall may be formed from a layer of cyclic olefin copolymer in between two layers of polypropylene. A wall of a blister may be formed of layers of polypropylene, cyclic olefin copolymer, and polyacrylonitrile. In an embodiment, a wall of a blister may be formed of layers of polyvinyl chloride, cyclic olefin copolymer, and polyvinylidene chloride.

In some embodiments, one or more valves may be coupled to channels in the cartridge. FIG. 29 depicts an embodiment of valve placement in channels on a cartridge. Valves may direct flow of a fluid through a channel. One or more valves coupled to microfluidic channels 10150 may allow a predetermined amount of sample from a sample reservoir 10140 to be analyzed. In one embodiment, a cartridge 10130 may include a first valve 10152 which may allow control of the introduction of sample into a portion of channel 10150. A first valve 10152 may be closed during sample collection to inhibit sample from flowing towards the detection region. A first valve 10152 may be opened to allow a predetermined amount of sample to flow into a microfluidic channel 10150 coupled to the detection region 10180. One or more other valves in the cartridge may be closed to direct a flow of sample in the cartridge.

In certain embodiments, a predetermined amount of sample may be measured into channel 10150. In one embodiment, sample is introduced into channel 10150 by opening of valve 10152. Sample is block from detection region 10180 by closing of valve 10156. As sample fills channel 10150, a predetermined amount of sample may be collected by allowing sample exceeding the predetermined amount to enter an overflow reservoir or region. A second valve 10154 proximate an overflow region may be opened as sample enters channel 10150 to allow sample exceeding the predetermined amount to flow into an overflow region and/or waste reservoir 10190. After a predetermined amount of sample is measured in a channel 10150, first valve 10152 and second valve 10154 are closed to prevent sample from the sample collection region and the overflow region from flowing to a detection region 10180. A third valve 10156 may be opened to allow a sample to flow towards a detection region 10180. A fourth valve 10158 may be opened to allow buffer from a buffer reservoir 10160 to push the measured sample towards the detection region 10180. One or more valves in a fifth set of valves 10159 may be opened to allow one or more reagents to flow towards a mixing chamber and/or detection region 10180. One or more reagent reservoirs 10160 may be actuated such that reagent may flow to the detection region. Reagents may mix with a sample in a mixing chamber and/or mixing region. Reagents from a reagent reservoir 10160 may flow over one or more reagent pick-up pads 10170 and reconstitute one or more reagents on the reagent pick-up pad. In one embodiment, a buffer solution may be passed over a reagent pick-up pad and flow towards a mixing region and/or detection region 10180. A sample may be analyzed in a detection region, such as a microsieve-based detection region and/or platform. A cartridge may be flushed during or after analysis by buffer from one or more reservoirs contained in the cartridge. Fluids may flow from a detection region to a waste reservoir.

Valves may include valves configured for microfluidic channels, such as gate valves, check valves, passive valves, active valves, and/or pinch valves. In one embodiment, pinch valves may be used in a cartridge to control flow in microfluidic channels. Fluids such as a sample, reagents, and/or buffers may flow through channels in a cartridge and valves may control the direction of the flow. A pinch valve may include an opening 10240 in a cartridge, as depicted in FIG. 30A. A channel 10150 may be accessed through the opening 10240. The opening may have a concave lower surface 10250. When a cartridge is loaded in an instrument, openings 10240 in the cartridge may be aligned with actuators 10260 coupled to the instrument.

In some embodiments, an actuator 10260 may be positioned in an opening 10240 of a cartridge above a channel 10150 after a cartridge is positioned in an instrument, as depicted in FIG. 30B. A lower surface 10250 of the opening 10240 may have a shape such that a bottom surface of an actuator 10260 fits in the lower surface of the opening. As depicted in FIG. 30C, an actuator 10260 may apply pressure on the channel 10150 such that fluid is inhibited from flowing through the channel. When pressure is applied to the channel 10150 to restrict flow through the channel, the valve is closed.

Figure 31:
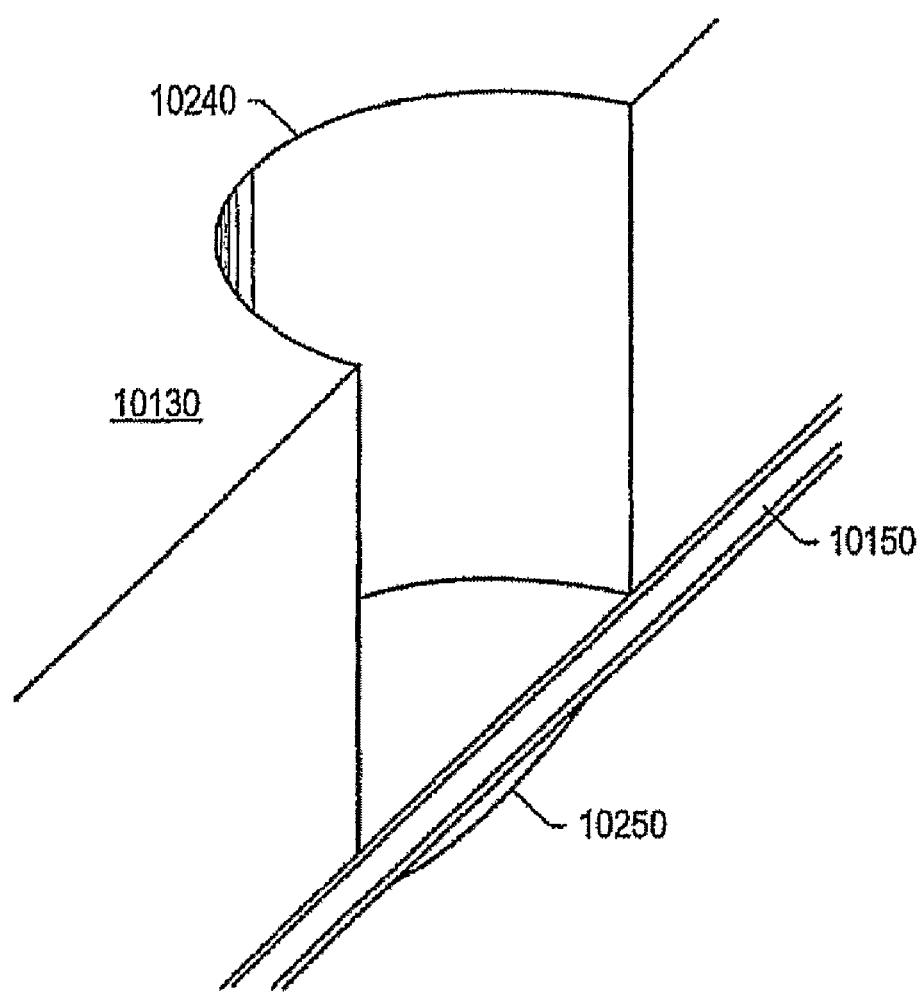
FIG. 31 depicts a cross-sectional view of a pinch valve.

In an embodiment, a lower surface 10250 of the opening may have a depth substantially equal to the diameter of the channel exposed in the opening. FIG. 31 depicts a cross-sectional view of an embodiment of a pinch valve in a cartridge. A pinch valve may include an opening 10240 in a cartridge 10130 that allows access to a channel 10150. A channel 10150 may be positioned above a lower surface 10250 of the opening 10240.

Figure 32B:
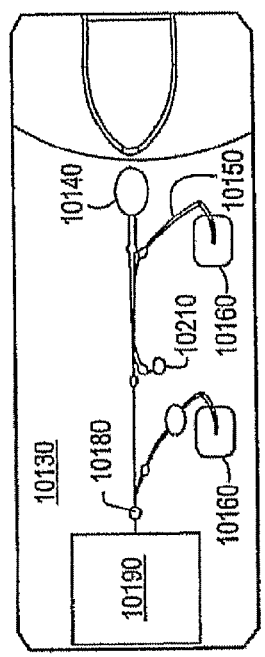
FIG. 32B depicts a top view of the cartridge of FIG. 32A.
Figure 32C:
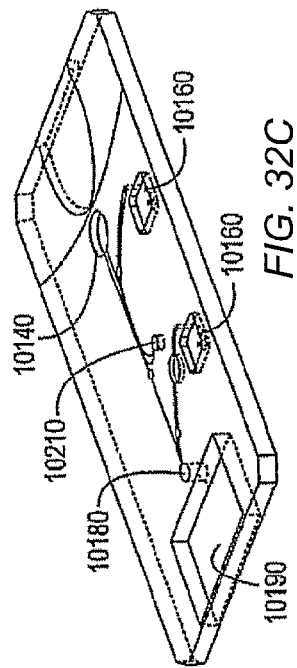
FIG. 32C depicts a perspective view of an embodiment of the cartridge of FIG. 32A.
Figure 32D:
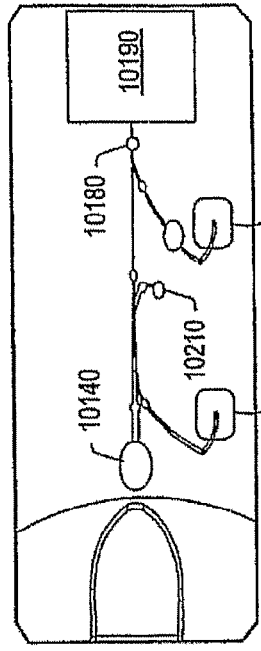
FIG. 32D depicts a bottom view of an embodiment of the cartridge of FIG. 32A.
Figure 32A:
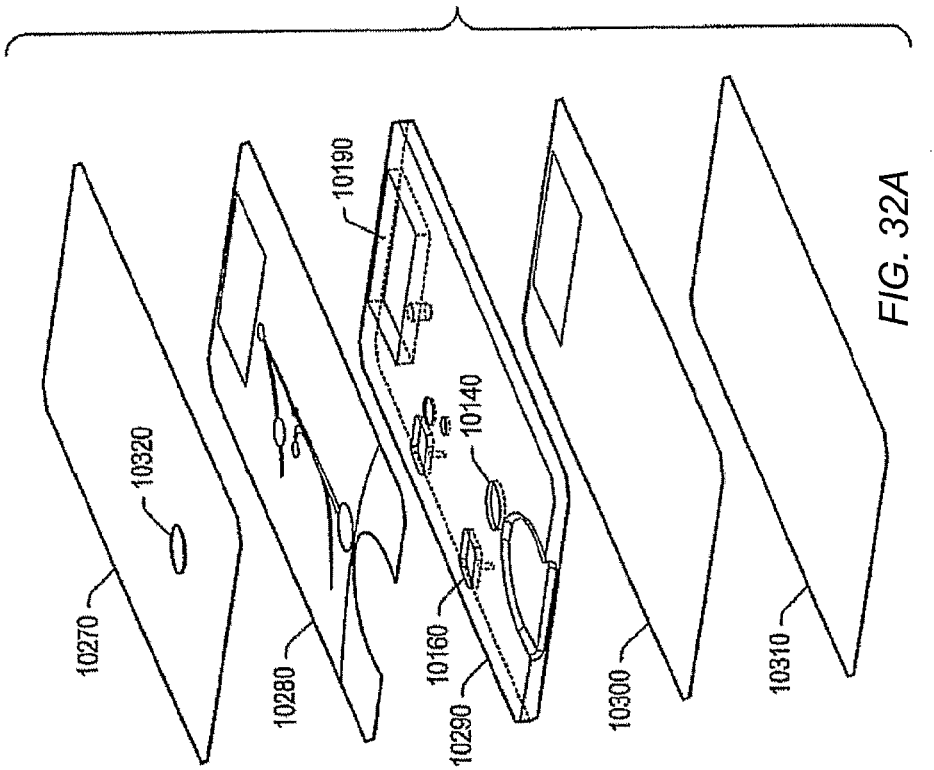
FIG. 32A depicts an exploded view of an embodiment of a cartridge that includes a sensor array.

FIG. 32A depicts an exploded view of an embodiment of a cartridge. A cartridge may include a top seal layer 10270, a top microchannel layer 10280, a center layer 10290, a bottom microchannel layer 10300, and/or a bottom seal layer 10310. Layers of a cartridge may be coupled together. Layers of a cartridge may be sealed together. Creating a cartridge from several layers may facilitate fabrication. A top seal layer 10270 may include access 10320 to a sample collection device 10140 or sample collection pick-up pad. Top 10280 and/or bottom 10300 microchannel layers may create a system of microchannels through the cartridge. A center layer 10290 may include reservoirs 10160 containing buffer and/or reagents, a portion of a sample collection device 10140, and/or a waste reservoir 10190. FIG. 32B depicts a top view of an embodiment of a cartridge. FIG. 32C depicts a perspective view of an embodiment of a cartridge. FIG. 32D depicts a bottom view of an embodiment of a cartridge.

Figure 33:
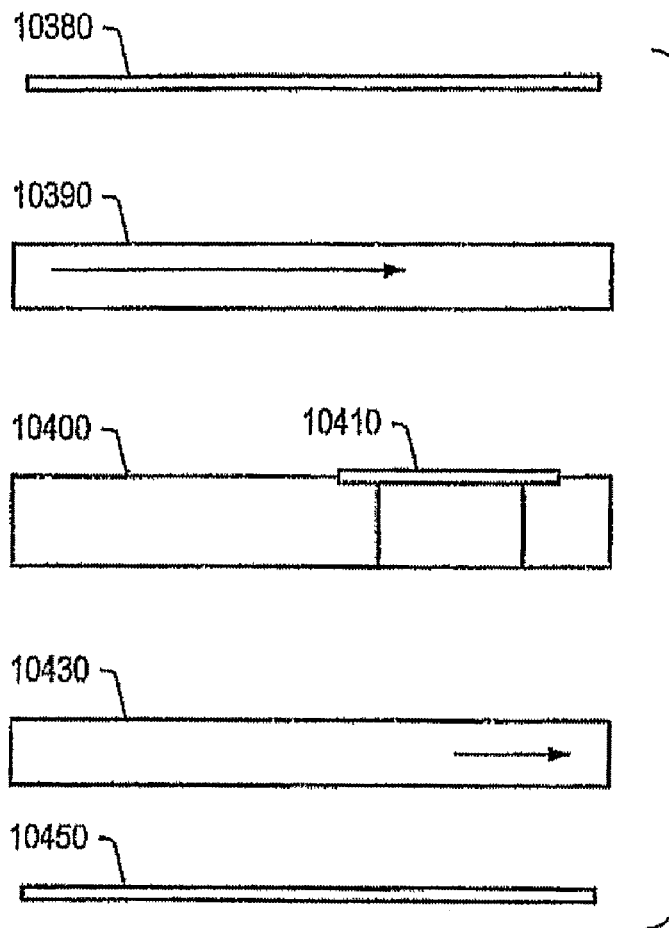
FIG. 33 depicts an exploded side view of an embodiment of a cartridge.

FIG. 33 depicts an exploded side view of an embodiment of a cartridge. Top 10380 and bottom 10450 seal layers may substantially contain fluid in the top 10390 and bottom 10430 microchannel layers. In an embodiment a fluid may flow from a top microchannel layer 10390 through a detection region 10410 in the center layer 10400 to a bottom microchannel layer 10430. Fluid may flow through the bottom microchannel layer 10430 to a waste reservoir.

Figure 34:
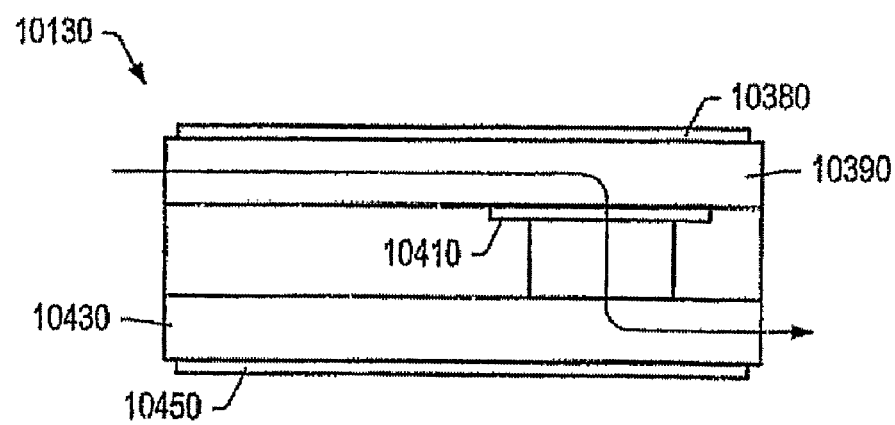
FIG. 34 depicts a side view of an embodiment of a cartridge.

FIG. 34 depicts a side view of an embodiment of a cartridge 10130. In some embodiments, fluid may flow from a top microchannel layer 10390 through a detection region 10410. Fluid may pass from the detection region 10410 through the bottom microchannel layer 10430 to a waste reservoir. Top 10380 and bottom 10450 seal layers may substantially retain fluid in microchannel layers.

FIG. 35A depicts an exploded view of another embodiment of a cartridge. An opening 10320 in the top seal layer 10270 may allow sample to be deposited in a sample collection device 10140 on the cartridge. When a sample is deposited in the cartridge one or more valves in a channel 10150 may inhibit a sample from flowing towards a detection region 10180. FIG. 35B depicts an embodiment of an arrangement of valves prior to and during deposition of a sample on the cartridge. During deposition of a sample, first 10330, second 10340, third 10350, and fourth 10360 valves may be closed to inhibit flow of sample through the cartridge.

In some embodiments, after a sample is deposited on the cartridge, an amount of sample may flow from the sample collection device 10140 through a channel 10150 via capillary action, as depicted in FIG. 36A. FIG. 36B depicts an arrangement of valves that allows sample to flow into a channel. A first valve 10330 may be open to allow a sample to flow into a microchannel. Second 10340 and third 10350 valves may be closed to control a flow of the sample. Closing a second valve 10340 may inhibit sample from flowing towards a buffer reservoir. Closing a third valve 10350 may allow a predetermined amount of sample to be measured. A fourth valve may be opened to allow sample in the channel to flow into an overflow reservoir.

FIG. 37A depicts an embodiment of sample flow in a cartridge. In some embodiments, it may be desirable to allow a portion of sample to flow over a detection region 10180. A predetermined amount of sample 10145 may be measured and allowed to flow towards the detection region 10180. A predetermined amount of sample may be measured by allowing sample in excess of a predetermined amount to flow into an overflow region 10210. An overflow region 10210 may be coupled to a waste reservoir 10190. Valves in the cartridge may inhibit sample in a main channel from flowing into channels coupled to reservoirs 10160. After a predetermined amount of sample is measured, valves may be closed to inhibit additional sample from flowing into the channel containing the predetermined amount of sample. For example, as depicted in FIG. 37B, a first valve 10330 may be closed to inhibit additional sample from a sample collection device 10140 from entering a channel. Second 10340 and third 10350 valves may remain closed. A fourth valve 10360 may be closed to prevent sample from the overflow region 10210 from flowing into the channel.

After a predetermined amount of sample is measured, a reservoir 10160 may be actuated, as depicted in FIG. 38A. A reservoir may contain buffer and/or reagents. An actuator may release buffer from a reservoir. A buffer reservoir may be similar to a blister pack. As depicted in FIG. 38B, a third valve 10350 may be opened to allow fluid to flow towards a detection region. Actuation a buffer reservoir 10160 may cause buffer to be released from a reservoir into a microchannel. A reservoir 10160 may be coupled to the cartridge so that fluid from the reservoir may flow from the reservoir towards the detection region 10180. A reservoir 10160 may be positioned in the cartridge so that buffer from a reservoir may push a predetermined amount of sample 10145 towards a detection region 10180. In an embodiment, a buffer may flow from a reservoir 10160 over a microsieve in a detection region 10180 to wash the microsieve after the sample flows over the microsieve. The buffer may then pass over the microsieve and into the waste reservoir 10190.

FIG. 38B depicts an arrangement of valves in an embodiment of a cartridge that may allow a buffer to push a sample through a microchannel and towards a detection region. A first valve 10330 may be closed so that a sample may be inhibited from reentering a sample collection device 10140 or sample pick-up pad. A second valve 10340 may be opened to allow fluid from a buffer reservoir to flow towards a detection region. A fourth valve 10360 may be closed such that fluid may be inhibited from flowing into the overflow reservoir 10210. A third valve 10350 may be open such that fluid may flow towards a detection region.

Figure 39:
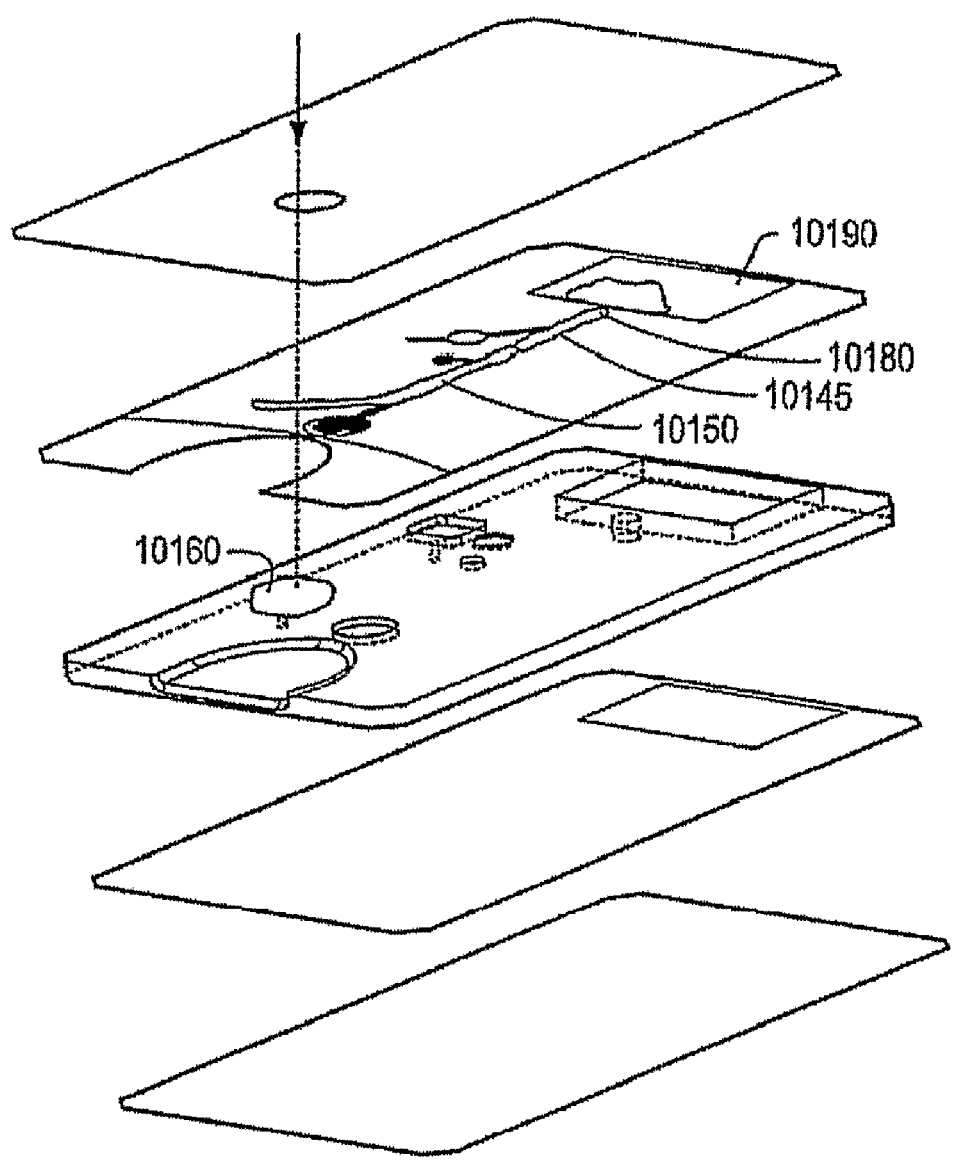
FIG. 39 depicts an embodiment of buffer pushing sample towards a detection region.
Figure 40:
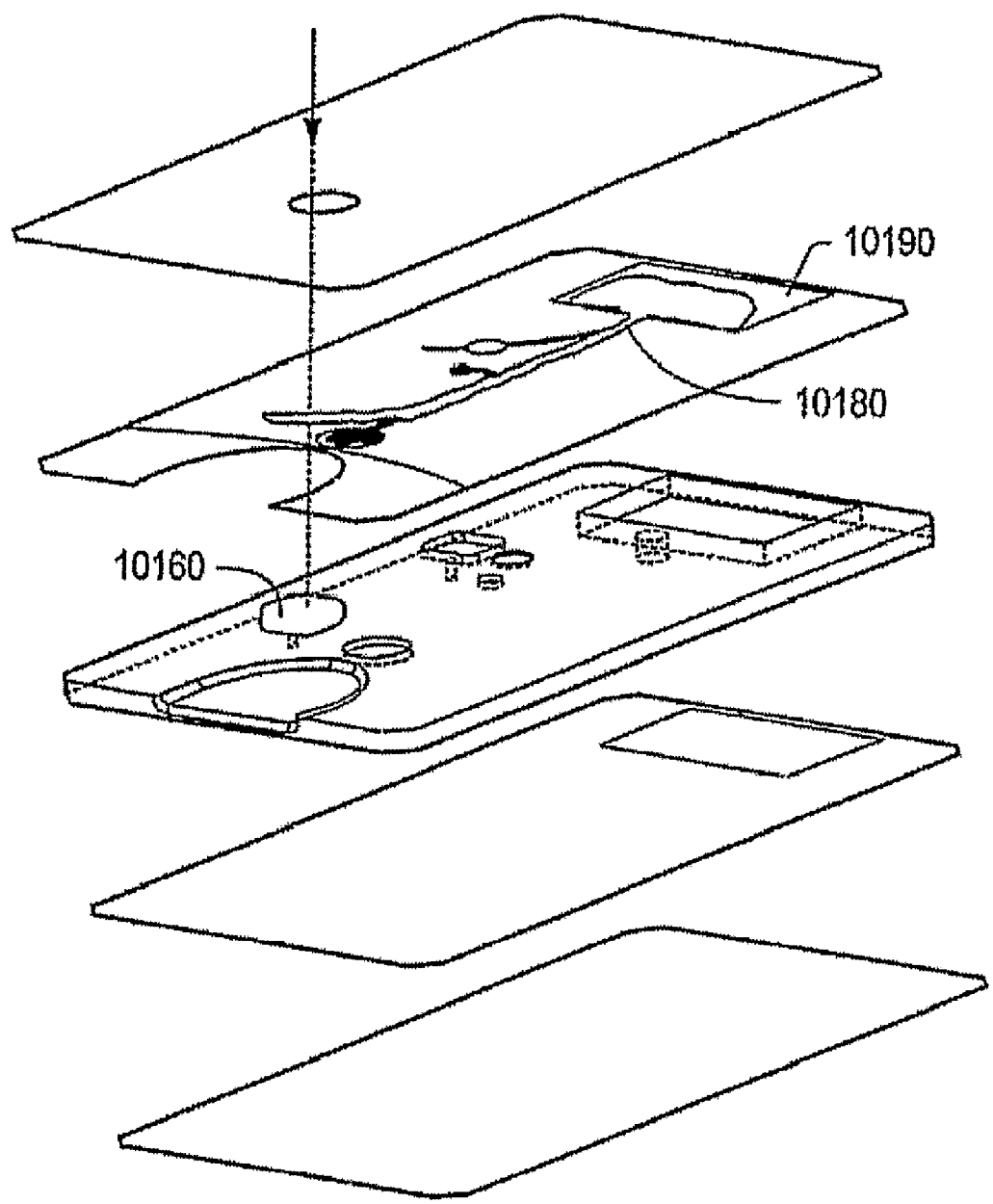
FIG. 40 depicts an embodiment of buffer pushing sample towards a detection region.

As the reservoir 10160 is actuated, buffer is released into a channel 10150 that couples the reservoir to a main channel containing the measured sample 10145. A main channel may couple a sample collection device 10140 to a detection region 10180 and/or waste reservoir 10190. The released buffer may push the predetermined amount or measured amount of sample 10145 towards a detection region 10180, as depicted in FIG. 39. Sample may pass over a detection region 10180, such as a microsieve, and into a waste reservoir 10190. As depicted in FIG. 40, a buffer reservoir 10160 may be activated and buffer may be released such that the substantially all of the measured amount of sample and/or buffer flows over the detection region 10180. Fluid (e.g., sample and/or buffer) that passes through the detection region 10180 may flow into a waste reservoir 10190.

A reservoir 10370 containing reagents and/or buffer may be actuated to release reagents and/or buffer into channels in the cartridge, as depicted in FIG. 41A. FIG. 41B depicts an embodiment of valves in a cartridge. A first valve 10330 may be closed to prevent fluids from entering a sample collection device 10140. A second valve 10340 may be closed after buffer is released from a reservoir to push sample towards a detection region. Third 10350 and fourth 10360 valves may be closed to substantially inhibit fluid from flowing into an overflow region 10210 and/or away from a detection region. A fifth valve 10360 proximate a reservoir 10160 containing buffer and/or reagents may be opened to allow buffer and/or reagents to flow over a detection region.

Actuating a reservoir 10370 may push fluids from a reservoir over a reagent pad towards a detection region 10180 and/or waste reservoir 10190. A reservoir 10370 may include buffer and/or reagents. Reagents on a reagent pack may be reconstituted as the fluid from the reservoir 10370 passes over the reagent pack. A reservoir 10370 may be coupled to a detection region 10180 and/or a waste reservoir 10190 via one or more channels. One or more reagents may react with the sample in the detection region. In some embodiments, reagents from one or more reagent reservoirs and/or reagent packs may mix with a sample in a mixing chamber. After a fluid containing reagents from a reagent pad and/or a reservoir 10370 pass over a detection region 10180. Reagents may react with a portion of the sample in the detection region 10180. Unreacted reagents, excess reagents, and/or buffer may flow from the detection region and into a waste reservoir 10190. A reservoir 10370 may be actuated until a predetermined amount of reagents and/or buffer pass over the detection region 10180 and into a waste reservoir 10190. In some embodiments, a reservoir may be actuated to push buffer from the reservoir over the detection region. In certain embodiments, after analysis of the detection region, a reservoir may be actuated to release buffer and wash the detection region. Analysis of the sample may be repeated after analysis of the detection region.

As used in the specification and the appended claims, the singular forms "a," "an" and "the" include plural referents unless the context clearly dictates otherwise. Thus, for example, reference to "binding agent" includes mixtures of two or more such agents, and the like.

"Optional" or "optionally" means that the subsequently described event or circumstance can, but may not occur, and that the description includes instances where said event or circumstance occurs and instances where it does not. "In some embodiments" means that a particular event or circumstances is present or occurs in at least some referents but may coexist with other events or circumstances present in other referents. Thus, an event or circumstance described "in some embodiments" may coexist with events or circumstances also described "in some embodiments."

In this patent, certain U.S. patents and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description to the invention. Changes can be made in the elements described herein without departing from the spirit and scope of the invention as described in the following claims. In addition, it is to be understood that features described herein independently may, in certain embodiments, be combined.

What is claimed is:

1. A cartridge for differential assay of white blood cell populations, the cartridge comprising:
    a chamber;
    a pad connected to the chamber via a fluid channel, wherein the pad is a reagent pad containing therein three binding agents each labeled with a different fluorophore;
    a microsieve positioned at least partially within the chamber, wherein pores of the microsieve are configured to retain white blood cells from a blood sample and to allow red blood cells to pass through the microsieve,
    wherein the fluorophore-labeled binding agents are flowed from the pad and over the microsieve and allowed to differentially bind to populations of white blood cells previously captured on the microsieve,
    wherein an image can be obtained from the microsieve, and
    wherein the fluorophore-labeled binding agents specifically bind to different populations of white blood cells so as to allow the different populations of cells to be distinguishably detectable by fluorescence.

2. The cartridge of claim 1, wherein a first one of the binding agents binds CD2+ white blood cells, a second one of the binding agents binds CD4+ white blood cells, and a third one of the binding agents binds CD19+ white blood cells.

3. The cartridge of claim 1, wherein at least one of the binding agents is an antibody to a white blood cell surface receptor.

4. The cartridge of claim 3, wherein the antibody binds a surface receptor selected from the group consisting of CD2, CD4, CD19, and CD56.

5. The cartridge of claim 1, wherein the microsieve is a polycarbonate track-etched microsieve.

6. The cartridge of claim 1, wherein the volume of the blood sample is a known volume.

7. The cartridge of claim 1, further comprising a support structure positioned beneath the microsieve and at least partially within the chamber, wherein the support structure maintains the microsieve in a relatively planar orientation and allows filtered material to pass through the microsieve.

* * * * *